US007399279B2

(12) United States Patent
Abend et al.

(10) Patent No.: US 7,399,279 B2
(45) Date of Patent: Jul. 15, 2008

(54) TRANSMITTER PATTERNS FOR MULTI BEAM RECEPTION

(75) Inventors: Kenneth Abend, Huntingdon Valley, PA (US); Elsayed H. Attia, Plymouth Meeting, PA (US)

(73) Assignee: Physiosonics, Inc, Seattle, WA (US)

( * ) Notice: Subject to any disclaimer, the term of this patent is extended or adjusted under 35 U.S.C. 154(b) by 534 days.

(21) Appl. No.: 10/831,547

(22) Filed: Apr. 23, 2004

(65) Prior Publication Data

US 2004/0267127 A1 Dec. 30, 2004

Related U.S. Application Data

(63) Continuation-in-part of application No. 10/327,265, filed on Dec. 20, 2002, which is a continuation-in-part of application No. 09/926,666, filed as application No. PCT/US00/14691 on May 26, 2000, now Pat. No. 6,682,483.

(60) Provisional application No. 60/136,364, filed on May 28, 1999, provisional application No. 60/138,793, filed on Jun. 14, 1999, provisional application No. 60/152,886, filed on Sep. 8, 1999, provisional application No. 60/343,061, filed on Dec. 20, 2001.

(51) Int. Cl.
*A61B 8/00* (2006.01)

(52) U.S. Cl. ........................................ 600/450; 600/459

(58) Field of Classification Search .......... 600/407–480
See application file for complete search history.

(56) References Cited

U.S. PATENT DOCUMENTS 4,503,861 A * 3/1985 Entrekin ..................... 600/454

(Continued)

FOREIGN PATENT DOCUMENTS

JP 01-145043 A2 6/1989

(Continued)

OTHER PUBLICATIONS

C. Kasai, K. Namekawa, A. Koyano and R. Omoto, "Real-Time Two Dimensional Blood Imaging Using An Autocorrelation Technique", IEEE Transactions On Sonics and Ultrasonics, vol. SU-32, No. 3, pp. 458-464, May 1985.

(Continued)

*Primary Examiner*—Brian Casler
*Assistant Examiner*—Nasir Shahrestani
(74) *Attorney, Agent, or Firm*—Ann W. Speckman; Speckman Law Group PLLC

(57) ABSTRACT

Provided herein is a method for use in medical applications that permits (1) affordable three-dimensional imaging of blood flow using a low-profile easily-attached transducer pad, (2) real-time blood-flow vector velocity, and (3) long-term unattended Doppler-ultrasound monitoring in spite of motion of the patient or pad. The pad and associated processor collects and Doppler processes ultrasound blood velocity data in a three dimensional region through the use of a planar phased array of piezoelectric elements. The invention locks onto and tracks the points in three-dimensional space that produce the locally maximum blood velocity signals. The integrated coordinates of points acquired by the accurate tracking process is used to form a three-dimensional map of blood vessels and provide a display that can be used to select multiple points of interest for expanded data collection and for long term continuous and unattended blood flow monitoring. The three dimensional map allows for the calculation of vector velocity from measured radial Doppler.

A thinned array (greater than half-wavelength element spacing of the transducer array) is used to make a device of the present invention inexpensive and allow the pad to have a low profile (fewer connecting cables for a given spatial resolution). The full aperture is used for transmit and receive so that there is no loss of sensitivity (signal-to-noise ratio) or dynamic range. Utilizing more elements (extending the physical array) without increasing the number of active elements increases the angular field of view. A further increase is obtained by utilizing a convex non-planar surface.

40 Claims, 36 Drawing Sheets

U.S. PATENT DOCUMENTS

| | | | |
|---|---|---|---|
| 4,644,795 A | | 2/1987 | Augustine |
| 5,027,821 A | * | 7/1991 | Hirama et al. .............. 600/447 |
| 5,148,810 A | * | 9/1992 | Maslak et al. ............... 600/447 |
| 5,184,135 A | | 2/1993 | Paradise |
| 5,261,408 A | | 11/1993 | Maslak et al. |
| 5,271,404 A | * | 12/1993 | Corl et al. .................... 600/454 |
| 5,278,757 A | | 1/1994 | Hoctor et al. |
| 5,291,892 A | | 3/1994 | O'Donnell |
| 5,305,756 A | * | 4/1994 | Entrekin et al. ............. 600/445 |
| 5,353,757 A | * | 10/1994 | Susa et al. ................ 123/41.29 |
| 5,365,929 A | | 11/1994 | Peterson |
| 5,390,677 A | | 2/1995 | Ferrera et al. |
| 5,406,163 A | | 4/1995 | Carson et al. |
| 5,409,010 A | | 4/1995 | Beach et al. |
| 5,460,180 A | | 10/1995 | Klepper et al. |
| 5,544,128 A | | 8/1996 | Kim et al. |
| 5,546,807 A | | 8/1996 | Oxaal et al. |
| 5,623,930 A | | 4/1997 | Wright et al. |
| 5,669,388 A | | 9/1997 | Vilkomerson |
| 5,675,554 A | * | 10/1997 | Cole et al. .................. 367/138 |
| 5,701,898 A | | 12/1997 | Adam et al. |
| 5,704,361 A | * | 1/1998 | Seward et al. ............... 600/459 |
| 5,722,412 A | | 3/1998 | Pflugrath et al. |
| 5,785,657 A | | 7/1998 | Breyer et al. |
| 5,787,049 A | | 7/1998 | Bates |
| 5,808,962 A | | 9/1998 | Steinberg et al. |
| 5,817,024 A | | 10/1998 | Ogle et al. |
| 5,840,033 A | | 11/1998 | Takeuchi |
| 5,911,692 A | * | 6/1999 | Hussain et al. .............. 600/447 |
| 5,922,962 A | | 7/1999 | Israk et al. |
| 5,928,151 A | | 7/1999 | Hossack et al. |
| 5,944,666 A | | 8/1999 | Hossack et al. |
| 5,971,927 A | | 10/1999 | Mine |
| 5,997,480 A | | 12/1999 | Sumanaweera et al. |
| 6,042,556 A | * | 3/2000 | Beach et al. .................... 601/3 |
| 6,066,096 A | | 5/2000 | Smith et al. |
| 6,080,107 A | | 6/2000 | Poland |
| 6,135,963 A | * | 10/2000 | Haider ....................... 600/447 |
| 6,135,971 A | | 10/2000 | Hutchinson et al. |
| 6,148,095 A | | 11/2000 | Prause et al. |
| 6,162,175 A | * | 12/2000 | Marian et al. ............... 600/447 |
| 6,186,949 B1 | | 2/2001 | Hatfield et al. |
| 6,228,031 B1 | | 5/2001 | Hwang et al. |
| 6,238,346 B1 | | 5/2001 | Mason |
| 6,368,277 B1 | | 4/2002 | Mao et al. |
| 6,390,984 B1 | * | 5/2002 | Pan et al. ..................... 600/453 |
| 6,423,006 B1 | | 7/2002 | Banjanin |
| 6,482,161 B1 | | 11/2002 | Sumanaweera et al. |
| 6,524,253 B1 | | 2/2003 | Abend |
| 6,544,181 B1 | | 4/2003 | Buck et al. |
| 6,610,014 B1 | | 8/2003 | Yamamoto et al. |
| 6,635,017 B1 | | 10/2003 | Moehring et al. |
| 6,682,483 B1 | | 1/2004 | Abend |
| 6,682,488 B2 | | 1/2004 | Abend |
| 6,685,645 B1 | * | 2/2004 | McLaughlin et al. ........ 600/447 |
| 6,689,064 B2 | | 2/2004 | Hager et al. |
| 6,725,076 B1 | | 4/2004 | Jenson |
| 2002/0151790 A1 | | 10/2002 | Abend |
| 2004/0019278 A1 | | 1/2004 | Abend et al. |
| 2004/0138563 A1 | | 7/2004 | Moehring et al. |
| 2004/0220474 A1 | | 11/2004 | Abend et al. |
| 2004/0254461 A1 | | 12/2004 | Ackerman |
| 2004/0254468 A1 | | 12/2004 | Herzog et al. |
| 2005/0004461 A1 | | 1/2005 | Abend |
| 2005/0004464 A1 | | 1/2005 | Miller |
| 2005/0004468 A1 | | 1/2005 | Abend et al. |
| 2005/0124885 A1 | | 6/2005 | Abend et al. |

FOREIGN PATENT DOCUMENTS

| | | |
|---|---|---|
| JP | 05-034446 A2 | 2/1993 |
| JP | 05-273336 A2 | 10/1993 |
| JP | 10-262969 A2 | 10/1998 |
| JP | 10-325843 A2 | 12/1998 |

OTHER PUBLICATIONS

K. Ferrara and G. De Angelis, "Color Flow Mapping", Ultrasound in Medicine and Biology, vol. 23, No. 2, pp. 321-345, Mar. 1997.

T. Buck, et al., "Flow Quantification in Valvular Heart Disease Based on the Integral of Backscattered Acousitc Power Using Doppler Ultrasound", PROC. IEEE, vol. 88, No. 3, pp. 307-330, Mar. 2000.

Gehlbach, Steve M., et al. "Digital Ultrasound Imaging Techniques Using Vector Sampling and Raster Line Reconstruction," Ultrasonic Imaging, vol. 3, pp. 83-107 (1981), Academic Press, Inc.

* cited by examiner

FIG. 2
FIG. 2A
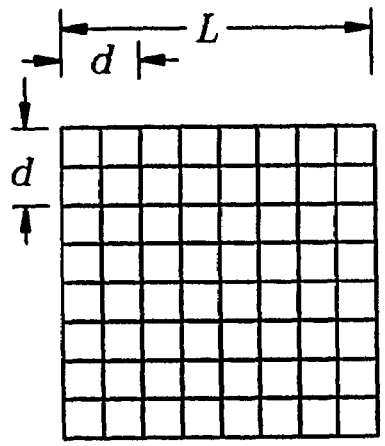
FIG. 2B
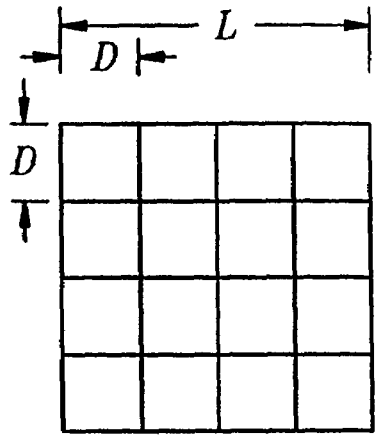
FIG. 3
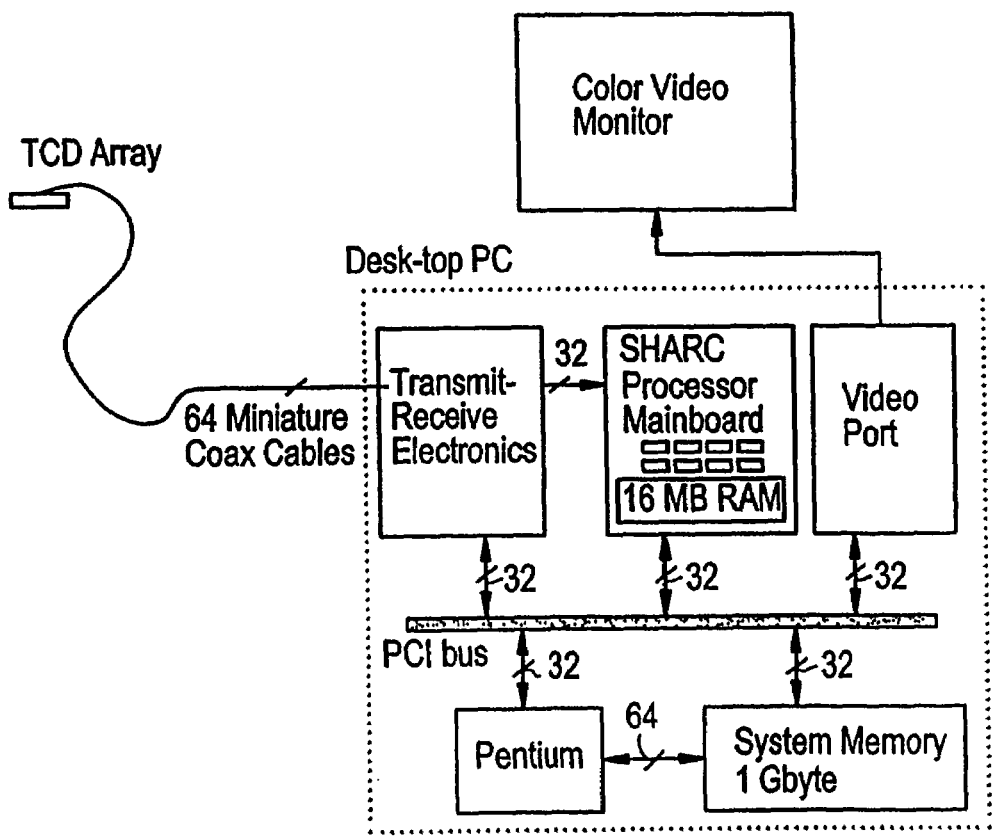

FIG. 4
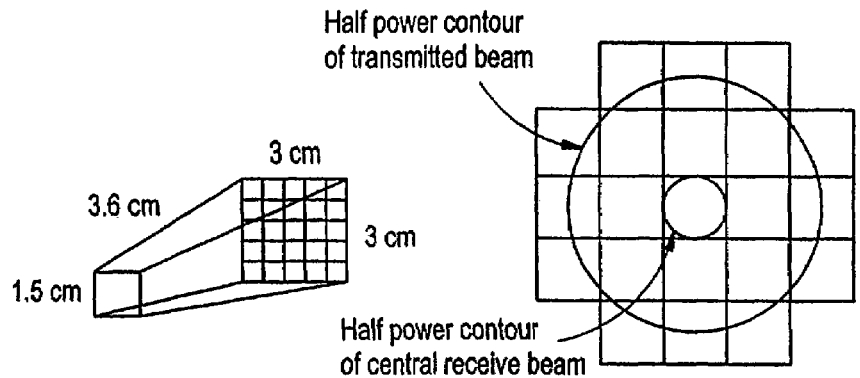
Half power contour of transmitted beam
Half power contour of central receive beam
3 cm
3.6 cm
3 cm
1.5 cm
FIG. 5
FIG. 5A
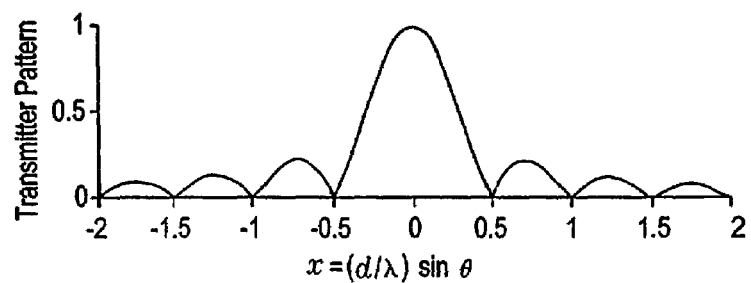
$x = (d/\lambda) \sin \theta$
FIG. 5B
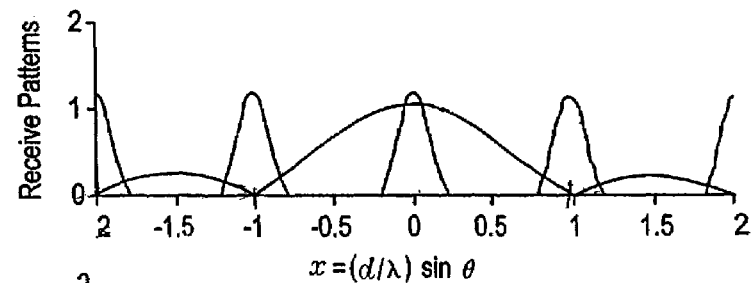
$x = (d/\lambda) \sin \theta$
FIG. 5C
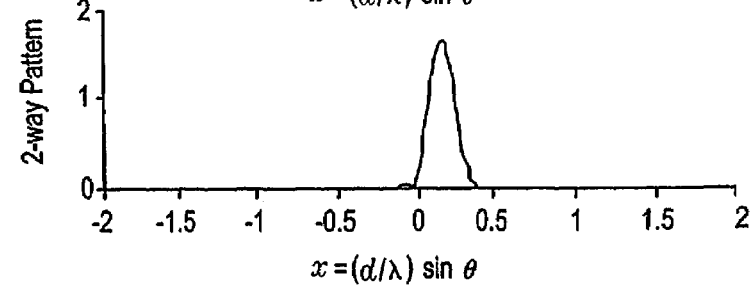
$x = (d/\lambda) \sin \theta$ FIG. 8
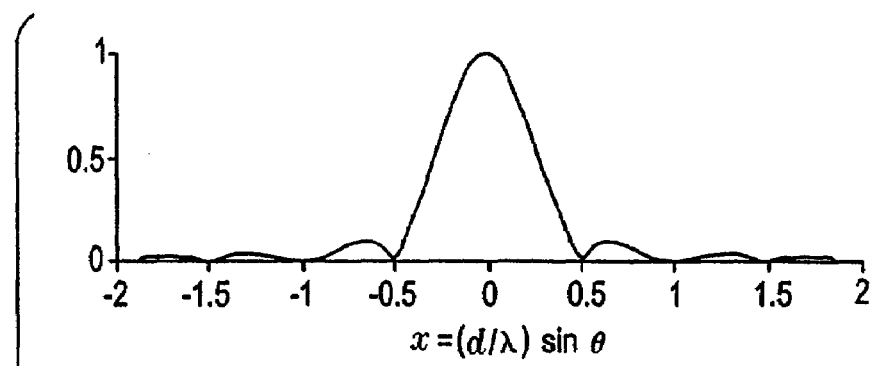
FIG. 8A
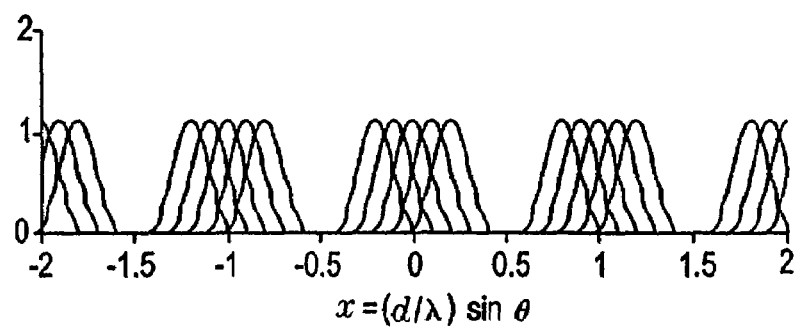
FIG. 8B
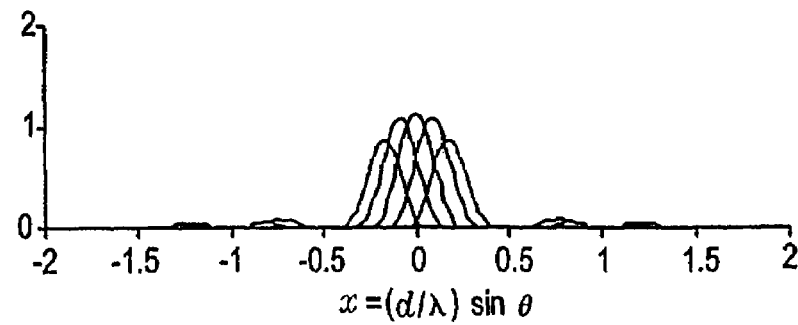
FIG. 8C

FIG. 10
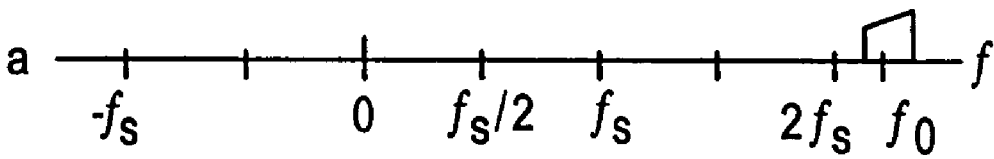
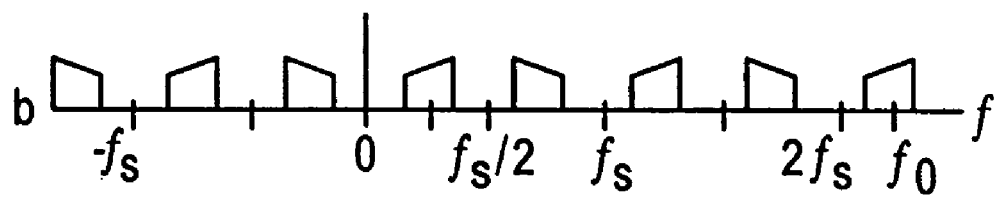
$f_0 = 2\text{ MHz} = 2f_s + f_s/2 \quad \Rightarrow \quad f_s = 888.9\text{ kHz}$
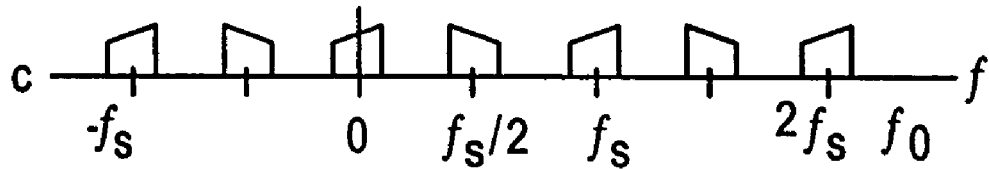
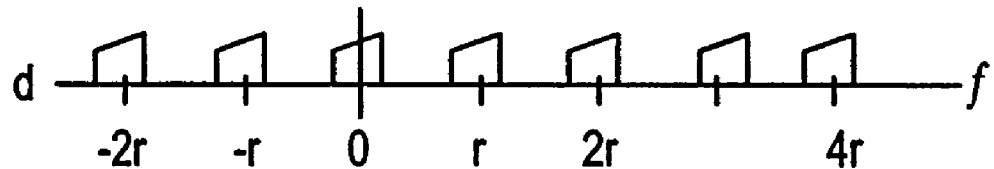

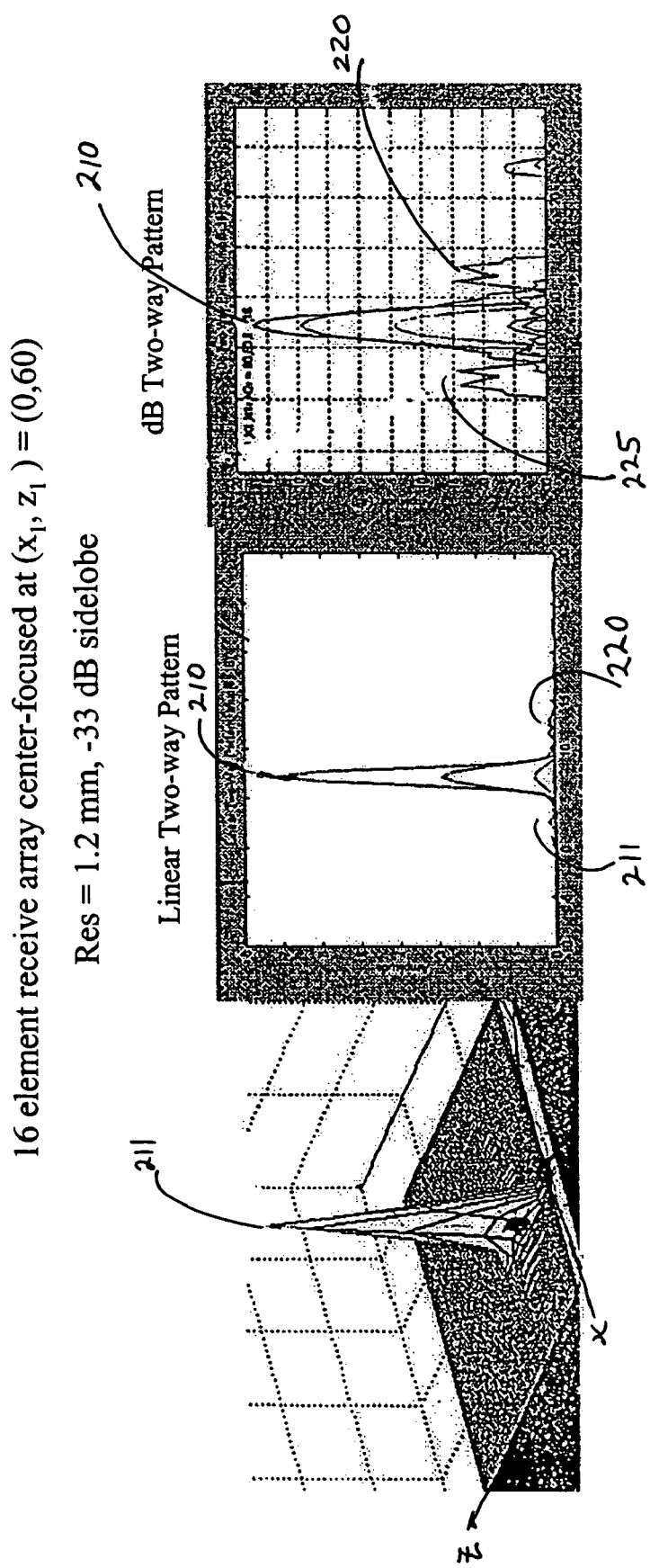

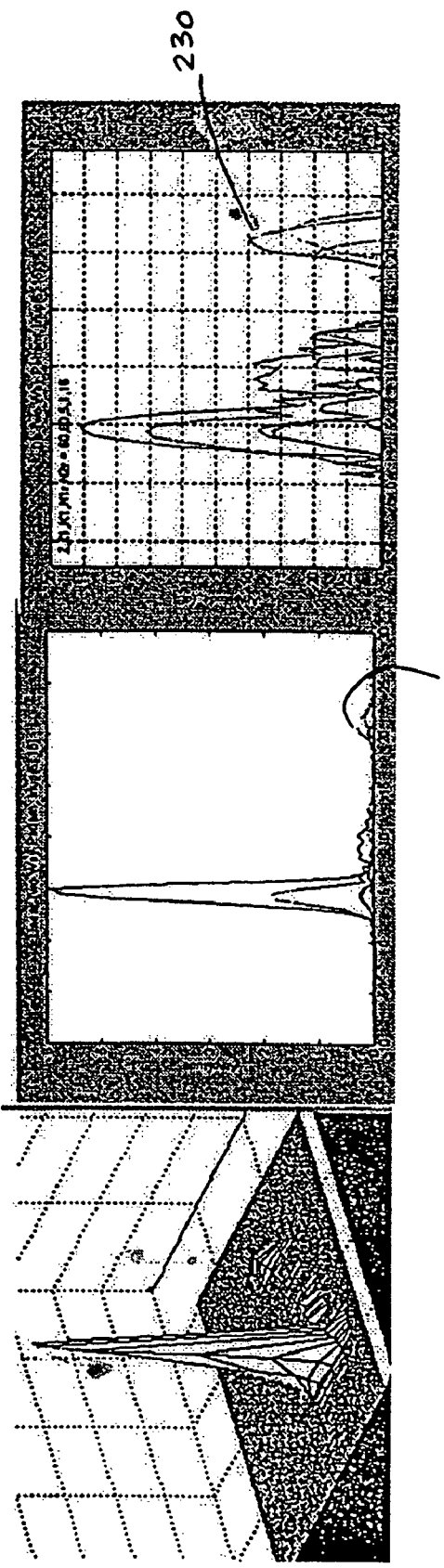

TRANSMITTER PATTERNS FOR MULTI BEAM RECEPTION

CROSS REFERENCE TO RELATED APPLICATIONS

This application is a continuation-in-part of U.S. application Ser. No. 10/327,265, entitled "Transmitter Patterns for Multi Beam Reception" and filed Dec. 20, 2002, which is a continuation-in-part of U.S. application Ser. No. 09/926,666, entitled "Device and Method for Mapping and Tracking Blood Flow and Determining Parameters of Blood Flow" and filed Mar. 20, 2002 (now U.S. Pat. No. 6,682,483), which is a national phase application of International Application No. PCT/US00/14691, filed May 26, 2000, which claims priority to U.S. provisional application Ser. No. 60/136,364, filed May 28, 1999; 60/138,793, filed Jun. 14, 1999; and 60/152,886, filed Sep. 8, 1999. The above-referenced U.S. application Ser. No. 10/327,265 claims priority to U.S. provisional application Ser. No. 60/343,061, entitled "Transmitter Patterns for Multi Beam Reception" and filed Dec. 20, 2001 (inventor Abend). The disclosure of each of the foregoing applications is hereby respectively incorporated by reference herein in its entirety.

FIELD OF THE INVENTION

The present invention involves an ultrasound Doppler method that permits non-invasive diagnosis and non-invasive unattended, continuous monitoring of vascular blood flow for medical applications. The invention also relates to a method and a system for the digital beam forming at the transmit and/or receive side of a phased array transducer.

BACKGROUND OF THE INVENTION

Blood velocity monitoring is not currently practical for intensive care unit (ICU) or surgical applications. For non-invasive brain blood velocity monitoring, for example, a transcranial Doppler (TCD) probe must be mounted in a ball joint that is attached to the head by a helmet. The probe must be carefully aimed and fastened in place by an experienced person who knows how to locate the middle cerebral artery. Slight movements cause the probe to lose the blood velocity signal. Moreover, conventional Doppler ultrasound probes used in these devices scan (either mechanically or by using an acoustic phased array) in only one angle (which we will call azimuth), and we will map only a single slice of the object being imaged.

Efforts have been made to modify such devices to provide real-time three dimensional (3-D) imaging. However, in order for a two dimensional (2-D) device to provide such imaging normally requires thousands of elements, and must form many thousands of pencil beams every $\frac{1}{30}$ second. Sensor cost grows with the number of elements in the array and the number of processing channels. Thus, such devices are cost prohibitive, as well as impractical.

Moreover, no automated procedure exists in current practice for precisely locating the optimum point at which to measure the Doppler signal. Conventional ultrasound Doppler-imaging devices can only measure radial velocity in blood vessels, and not the vector velocity or magnitude of the velocity of the blood.

Accordingly, what is needed is a new and useful Doppler ultrasound device and method that can automatically locate the optimum point at which to measure the Doppler signal, and thus provide medical providers with parameters such as vector velocity, the volume of blood passing through the blood vessel and the Doppler spectral distribution of the blood flow.

What is also needed is a new and useful Doppler ultrasound device and method that does not require it be placed on a patient with precision, and will enable a patient wearing the device to move freely.

The citation of any reference herein should not be construed as an admission that such reference is available as "Prior Art" to the instant application.

SUMMARY OF THE INVENTION

There is provided, in accordance with the present invention, a new, useful, and unobvious method of determining parameters of blood flow, such as vector velocity, blood flow volume, and Doppler spectral distribution, using sonic energy (ultrasound) and a novel thinned array. Also provided is a novel method of tracking blood flow and generating a three dimensional image of a blood vessel of interest that has much greater resolution than images produced using heretofore known ultrasound devices and methods.

Broadly, the present invention extends to a method for determining a parameter of blood flow in a blood vessel of interest, comprising the steps of:
a) providing an array of sonic transducer elements, wherein the element spacing in the array is greater than, equal or less than a half wavelength of the sonic energy produced by the elements, wherein at least one element transmits sonic energy, and a portion of the elements receive sonic energy;
b) directing sonic energy produced by the at least one element of the array into a volume of the subject's body having the blood vessel of interest,
c) receiving echoes of the sonic energy from the volume of the subject's body having the blood vessel of interest;
d) reporting the echoes to a processor programmed to
  i) Doppler process the echoes to determine radial velocity of the blood flowing in the blood vessel of interest;
  ii) calculate a three dimensional position of blood flow in the vessel of interest; and
  iii) calculate the parameter of blood flow in the blood vessel at the three dimensional position calculated in step (ii); and
(e) displaying the parameter on a display monitor that is electrically connected to the processor.

Moreover, a method of the present invention permits an operator examining a subject to obtain information on blood flow in a particular region of the blood vessel of interest.

As used herein, the phrases "element spacing" and "distance between the elements" can be used interchangeably and refer to the distance between the center of elements of an array.

Various methods can be used to determine the three dimensional position of blood flow. In a particular embodiment, the method comprises the steps of having the processor programmed to:
  i) determine a sum beam, an azimuth difference beam and an elevation difference beam from the echoes received from the blood vessel of interest;
  ii) modulate the directions of the transmitted and received sonic energy based upon the sum, azimuth difference and elevation difference beams in order to lock on to the highest Doppler energy calculated from echoes from the flow of blood in the blood vessel of interest, and
  iii) calculate the three dimensional position of the highest Doppler energy from the blood flow in the vessel of interest.

Optionally, the processor can also be programmed to determine at least one additional beam having an angle between the azimuth difference beam and the elevation difference beam prior to modulating the directions of the transmitted and received sonic energy, wherein the at least one additional beam is used to modulate the directions of the transmitted and received sonic energy. Naturally, the angle of the at least one additional beam can vary. In a particular embodiment, the at least one additional beam is at an angle that is orthogonal to the blood vessel of interest.

Moreover, the present invention extends to a method as described above, wherein steps (b) through (e) are periodically repeated so that the three dimensional position of blood flow in the vessel of interest is tracked, and the parameter of blood flow is periodically calculated and displayed on the display monitor. In a particular embodiment, the period of time between repeating steps (b) through (e) is sufficiently short so that the parameter being measured remains constant, e.g., 20 milliseconds.

The present invention further extends to a method for determining a parameter of blood flow in a particular region of a blood vessel of interest, comprising the steps of:
a) providing an array of sonic transducer elements, wherein the element spacing in the array is greater than, equal or less than a half wavelength of the sonic energy produced by the elements, wherein at least one element transmits sonic energy, and a portion of the elements receive sonic energy;
b) directing sonic energy produced by the at least one element of the array into a volume of the subject's body having the particular region of the blood vessel of interest,
c) receiving echoes of the sonic energy from the volume of the subject's body having the particular region of the blood vessel of interest;
d) reporting the echoes to a processor programmed to
  i) Doppler process the echoes to determine radial velocity of the blood flowing in the particular region of the blood vessel of interest;
  ii) calculate a three dimensional position of blood-flow in the particular region of the blood vessel of interest; and
  iii) calculate the parameter of blood flow in the particular region of the blood vessel of interest at the three dimensional position calculated in step (ii); and
(e) displaying the parameter on a display monitor that is electrically connected to the processor.

A particular method of calculating the three dimensional position of blow flow in such a method of the present invention comprises having the processor programmed to:
  i) determine a sum beam, an azimuth difference beam and an elevation difference beam from the echoes received from the particular region of the blood vessel of interest;
  ii) modulate the directions of the transmitted and received sonic energy based upon the sum, azimuth difference and elevation difference beams in order to lock on to the highest Doppler energy calculated from echoes received from the flow of blood in the particular region of the blood vessel of interest, and
  iii) calculate the three dimensional position of the highest Doppler energy from the blood flow in the particular region of the blood vessel of interest.

As explained above, at least one additional beam can also be determined and used to calculate the three dimensional position.

Furthermore, the present invention extends to a method for determining a parameter of blood flow in a blood vessel of interest, comprising the steps of:
a) providing an array of sonic transducer elements, wherein the element spacing in the array is greater than, equal or less than a half wavelength of the sonic energy produced by the elements, wherein at least one element transmits sonic energy, and a portion of elements receive sonic energy;
b) directing sonic energy produced by the at least one element of the array into a volume of the subject's body having the blood vessel of interest,
c) receiving echoes of the sonic energy from the volume of the subject's body having the blood vessel of interest;
d) reporting the echoes to a processor electrically connected to the elements of the array, wherein the processor is programmed to
  i) Doppler process the echoes to determine radial velocity of the blood flowing in the blood vessel of interest;
  ii) determine a sum beam, an azimuth difference beam and an elevation difference beam from the echoes received from the blood vessel of interest;
  iii) modulate the directions of the transmitted and received sonic energy based upon the sum, azimuth difference and elevation difference beams in order to lock on to the highest Doppler energy calculated from echoes from the flow of blood in the blood vessel of interest,
  iv) calculate the three dimensional position of the highest Doppler energy from the blood flow in the vessel of interest; and
  v) calculate the parameter of blood flow in the blood vessel at the three dimensional position calculated in step (iv); and
(e) displaying the parameter on a display monitor that is electrically connected to the processor.

As explained above, an operator performing a method of the present invention can obtain blood flow parameters from a blood vessel of interest, and even from a particular region of a blood vessel of interest.

Moreover, the present invention extends to a method for determining a parameter of blood flow in a particular region of a blood vessel of interest, comprising the steps of:
a) providing an array of sonic transducer elements, wherein the element spacing in the array is greater than, equal or less than a half wavelength of the sonic energy produced by the elements, wherein at least one element transmits sonic energy, and a portion of the elements receive sonic energy;
b) directing sonic energy produced by the at least one element of the array into a volume of the subject's body having the particular region of the blood vessel of interest,
c) receiving echoes of the sonic energy from the volume of the subject's body having the particular region of blood vessel of interest;
d) reporting the echoes to a processor electrically connected to the elements of the array, wherein the processor is programmed to
  i) Doppler process the echoes to determine radial velocity of the blood flowing in the particular region of the blood vessel of interest;
  ii) determine a sum beam, an azimuth difference beam and an elevation difference beam from the echoes received from the particular region of the blood vessel of interest;
  iii) modulate the directions of the transmitted and received sonic energy based upon the sum, azimuth difference and elevation difference beams in order to lock on to the highest Doppler energy calculated from echoes from the flow of blood in the particular region of the blood vessel of interest,
  iv) calculate the three dimensional position of the highest Doppler energy from the blood flow in the particular region of the blood vessel of interest; and v) calculate the parameter of blood flow in the particular region of the blood vessel at the three dimensional position calculated in step (iv); and
(e) displaying the parameter on a display monitor that is electrically connected to the processor.

In another embodiment, the present invention extends to a device for determining a parameter of blood flow in a blood vessel of interest, comprising:
a) an array of sonic transducer elements, wherein the element spacing in the array is greater than, equal or less than a half wavelength of the sonic energy produced by the elements, and at least one element transmits sonic energy, and a portion of the elements receive sonic energy;
b) a processor electrically connected to the array so that echoes received from a volume of the subject's body having the blood vessel of interest due to directing sonic energy produced by the at least one element of the array into the subject's body is reported to the processor, wherein the processor is programmed to:
  i) Doppler process the echoes to determine radial velocity of the blood flowing in the blood vessel of interest;
  ii) calculate a three dimensional position of blood flow in the blood vessel of interest; and
  iii) calculate the parameter of blood flow in the blood vessel of interest at the three dimensional position calculated in step (ii); and
(c) a display monitor that is electrically connected to the processor which displays the parameter of blood flow calculated by the processor.

A parameter of blood that can be determined with a device of the present invention includes blood flow volume, vector velocity, Doppler spectral distribution, etc. The parameter being measured can be an instantaneous value, or an average value determined over a heart cycle.

Moreover, the present invention extends to a device as described above, wherein the processor is programmed to:
  i) determine a sum beam, an azimuth difference beam and an elevation difference beam from the echoes received from the blood vessel of interest after Doppler processing the echoes;
  ii) modulate the directions of the transmitted and received sonic energy based upon the sum, azimuth difference and elevation difference beams in order to lock on to the highest Doppler energy calculated from echoes from the flow of blood in the blood vessel of interest;
  iii) calculate the three dimensional position of the highest Doppler energy from the blood flow in the vessel of interest; and
  iv) calculate the parameter of blood flow in the blood vessel of interest at the three dimensional position calculated in (iii).

Optionally, a processor of a device of the present invention can be further programmed to determine at least one additional beam having an angle between the azimuth difference beam and the elevation difference beam prior to modulating the directions of the transmitted and received sonic energy, wherein the at least one additional beam is used to modulate the directions of the transmitted and received sonic energy. In a particular embodiment, the at least one additional beam is at an angle that is orthogonal to the blood vessel of interest.

Moreover, in a another embodiment of a device of the present invention, the distance between the elements of the array is greater than ½ the wavelength of the sonic energy generated by the at least one element.

Furthermore, the present invention extends to a device for determining a parameter of blood flow in a blood vessel of interest, comprising:

a) an array of sonic transducer elements, wherein the element spacing in the array is greater than, equal or less than a half wavelength of the sonic energy produced by the elements, and at least one element transmits sonic energy, and portion of the elements receive sonic energy;
b) a processor electrically connected to the array so that echoes received from a volume of the subject's body having the blood vessel of interest due to directing sonic energy produced by the at least one element of the array into the subject's body is reported to the processor, wherein the processor is programmed to:
  i) Doppler process the echoes to determine radial velocity of the blood flowing in the blood vessel of interest;
  ii) calculate a three dimensional position of blood flow in the blood vessel of interest; and
  iii) calculate the parameter of blood flow in the blood vessel of interest at the three dimensional position calculated in step (ii)
(c) a display monitor that is electrically connected to the processor which displays the parameter of blood flow calculated by the processor.

Particular parameters of blood flow that can be determined with a device of the present invention include, but certainly are not limited to blood flow volume, vector velocity, and Doppler spectral distribution. The parameter being measured can be an instantaneous value, or an average value determined over a heart cycle.

In addition, a processor of a device of the present invention can be further programmed to determine at least one additional beam having an angle between the azimuth difference beam and the elevation difference beam prior to modulating the directions of the transmitted and received sonic energy, wherein the at least one additional beam is used to modulate the directions of the transmitted and received sonic energy. In a particular embodiment, the at least one additional beam is at an angle that is orthogonal to the blood vessel of interest.

Moreover, the present invention extends to a method for generating a three dimensional image using sonic energy of a blood vessel of interest in a subject, the method comprising the steps of:
a) providing an array of sonic transducer elements, wherein the element spacing in the array is greater than, equal or less than a half wavelength of the sonic energy produced by the elements, wherein at least one element transmits sonic energy, and a portion of the elements receive sonic energy;
b) directing sonic energy produced by the at least one element of the array into a volume of the subject's body having the blood vessel of interest,
c) receiving echoes of the sonic energy from the volume of the subject's body having the blood vessel of interest;
d) reporting the echoes to a processor programmed to
  i) Doppler process the echoes to determine radial velocity of the blood flowing in the blood vessel of interest;
  ii) calculate a three dimensional position of blood flow in the blood vessel of interest;
  iii) repeat steps (i) through (ii) to generate a plurality of calculated three dimensional positions; and
  vi) generate a three dimensional image of the blood vessel of interest from the plurality of calculated three dimensional positions; and
(e) displaying the three dimensional image on a display monitor that is electrically connected to the processor.

Furthermore, the present invention permits an operator utilizing a method of the present invention to generate a three dimensional image of not only a blood vessel in the body, but even a particular region of a blood vessel in the body.

Numerous means available for calculating the three dimensional position of a blood vessel and even a particular portion of a blood vessel are encompassed by the present invention. A particular means comprises having the programmed processor:

i) determine a sum beam, an azimuth difference beam and an elevation difference beam from the echoes received from the blood vessel of interest after Doppler processing the echoes;

ii) modulate the directions of the transmitted and received sonic energy based upon the sum, azimuth difference and elevation difference beams in order to lock on to the highest Doppler energy calculated from echoes from the flow of blood in the blood vessel of interest, and iii) calculate the three dimensional position of the highest Doppler energy from the blood flow in the vessel of interest, and iv) repeat steps (i) through (iii) to generate a plurality of calculated three dimensional positions.

Optionally, a processor of a method of the present invention can also be programmed to determine at least one additional beam having an angle between the azimuth difference beam and the elevation difference beam prior to modulating the directions of the transmitted and received sonic energy, and the at least one additional beam is also used to modulate the directions of the transmitted and received sonic energy, and calculate the three dimensional position of the highest Doppler energy. In a particular embodiment, the at least one additional beam is at an angle that is orthogonal to the blood vessel of interest.

The present invention also extends to a method for generating a three dimensional image of a blood vessel of interest in a subject using sonic energy, the method comprising the steps of:

a) providing an array of sonic transducer elements, wherein the element spacing in the array is greater than, equal or less than a half wavelength of the sonic energy produced by the elements, wherein at least one element transmits sonic energy, and a portion of the elements receive sonic energy;

b) directing sonic energy produced by the at least one element of the array into a volume of the subject's body having the blood vessel of interest, c) receiving echoes of the sonic energy from the volume of the subject's body having the blood vessel of interest;

d) reporting the echoes to a processor programmed to i) Doppler process the echoes to determine radial velocity of the blood flowing in the blood vessel of interest;

ii) determine a sum beam, an azimuth difference beam and an elevation difference beam from the echoes received from a portion of the blood vessel of interest;

iii) modulate the directions of the transmitted and received sonic energy based upon the sum, azimuth difference and elevation difference beams in order to lock on to the highest Doppler energy calculated from echoes from the flow of blood in the blood vessel of interest, iv) calculate the three dimensional position of the highest Doppler energy from the blood flow in the vessel of interest; and v) repeat steps (i) through (iv) to generate a plurality of calculated three dimensional positions;

vi) generate a three dimensional image of the blood vessel of interest from the plurality of calculated three dimensional positions; and (e) displaying the three dimensional image on a display monitor that is electrically connected to the processor.

Optionally, the three dimensional image can be of a particular region of a blood vessel of interest. Moreover, a processor of a method described herein can also determine at least one additional beam having an angle between the azimuth difference beam and the elevation difference beam prior to modulating the directions of the transmitted and received sonic energy, and the at least one additional beam is also used to modulate the directions of the transmitted and received sonic energy, and calculate the three dimensional position of the highest Doppler energy. Angles for use with the at least one additional beam are described above.

Moreover, in another embodiment of the present invention, the distance between the elements of the array is greater than ½ the wavelength of the sonic energy generated by the at least one element.

Furthermore, the present invention extends to a device generating a three dimensional image of a blood vessel of interest in a subject using sonic energy, comprising:

a) an array of sonic transducer elements, wherein the element spacing in the array is greater than, equal or less than a half wavelength of the sonic energy produced by the elements, and at least one element transmits sonic energy, and a portion of the elements receive sonic energy;

b) a processor electrically connected to the array so that echoes received from a volume of the subject's body having the blood vessel of interest due to directing sonic energy produced by the at least one element of the array into the subject's body is reported to the processor, wherein the processor is programmed to:

i) Doppler process the echoes to determine radial velocity of the blood flowing in the blood vessel of interest;

ii) calculate a three dimensional position of blood flow in the blood vessel of interest;

iii) repeat steps (i) through (ii) to generate a plurality of calculated three dimensional positions;

v) generate a three dimensional image from the plurality of calculated three dimensional positions, and (c) a display monitor that is electrically connected to the processor which displays the three dimensional image.

As explained above, a device of the present invention permits an operator to generate and display three dimensional images of a blood vessel of interest, and even of a particular region of a blood vessel that the operator wants to investigate closely. Moreover, in a particular embodiment, a processor of a device of the present invention can be programmed to calculate the three dimensional position of a blood vessel by i) determining a sum beam, an azimuth difference beam and an elevation difference beam from the echoes received from the blood vessel of interest after Doppler processing the echoes;

ii) modulating the directions of the transmitted and received sonic energy based upon the sum, azimuth difference and elevation difference beams in order to lock on to the highest Doppler energy calculated from echoes from the flow of blood in the blood vessel of interest, iii) calculating the three dimensional position of the highest Doppler energy from the blood flow in the vessel of interest; and iv) repeat steps (i) through (iii) in order to generate a plurality of calculated three dimensional positions used to generate the three dimensional image.

Optionally, the processor can be programmed to further determine at least one additional beam having an angle between the azimuth difference beam and the elevation difference beam prior to modulating the directions of the transmitted and received sonic energy, wherein the at least one additional beam is used to modulate the directions of the transmitted and received sonic energy. The angle between the azimuth difference beam and the elevation difference beam of the additional beam can vary. In a particular embodiment, the at least one additional beam is at an angle that is orthogonal to the blood vessel of interest.

Furthermore, the present invention extends to a thinned array for use in an ultrasound device, comprising a plurality of sonic transducer elements, wherein the element spacing in the array is greater than a half wavelength of the sonic energy produced by the elements, and the elements are positioned and sized within the array, and sonic energy is electronically steered by the elements so that any grating lobes produced by the sonic energy are suppressed. In a particular embodiment, the elements positioned and sized so that they are flush against each other.

Hence, the current invention performs blood velocity monitoring by collecting Doppler data in three dimensions; azimuth, elevation, and range (depth); so that the point (in three dimensional space) at which the velocity is to be monitored can be acquired and tracked when the patient or the sensor moves. The invention also produces a three dimensional map of the blood flow and converts measured radial velocity to true vector velocity Moreover, in this invention, once the desired signal is found, it will be precisely located and continually tracked with accuracy far better than the resolution. A heretofore unknown method to achieve sub-resolution tracking and mapping involves a novel and unobvious extension of a procedure called "monopulse". Monopulse tracking has been used in military applications for precisely locating and tracking a point target with electromagnetic radiation. However, it has never been utilized in connection with sonic waves to determine the velocity of moving fluids in vivo.

This invention provides: (1) affordable three-dimensional imaging of blood flow using a low-profile easily-attached transducer pad, (2) real-time vector velocity, and (3) long-term unattended Doppler-ultrasound monitoring in spite of motion of the patient or pad. None of these three features are possible with current ultrasound equipment or technology.

The pad and associated processor collects and Doppler processes ultrasound blood velocity data in a three-dimensional region through the use of a two-dimensional phased array of piezoelectric elements on a planar, cylindrical, or spherical surface Through use of unique beamforming and tracking techniques, the invention locks onto and tracks the points in three-dimensional space that produce the locally maximum blood velocity signals. The integrated coordinates of points acquired by the accurate tracking process is used to form a three-dimensional map of blood vessels and provide a display that can be used to select multiple points of interest for expanded data collection and for long term continuous and unattended blood flow monitoring. The three dimensional map allows for the calculation of vector velocity from measured radial Doppler.

In a particular embodiment, a thinned array (greater than half-wavelength element spacing of the transducer array) is used to make a device of the present invention inexpensive and allow the pad to have a low profile (fewer connecting cables for a given spatial resolution). The array is thinned without reducing the receiver area by limiting the angular field of view. The special 2-D phased array used in this invention makes blood velocity monitoring inexpensive and practical by (1) forming the beams needed for tracking and for re-acquiring the blood velocity signal and by (2) allowing for an element placement that is significantly coarser than normal half-wavelength element spacing. The limited range of angles that the array must search allows for much less than the normal half wavelength spacing without reducing the total receiver area.

Grating lobes due to array thinning can be reduced by using wide bandwidth and time delay steering. The array, or at least one element of the array, is used to sequentially insonate the beam positions. Once the region of interest has been imaged and coarsely mapped, the array is focused at a particular location on a particular blood vessel for measurement and tracking. Selection of the point or points to be measured and tracked can be based on information obtained via mapping and may be user guided or fully automatic. Selection can be based, for example, on peak response within a range of Doppler frequencies at or near an approximate location.

In the tracking mode a few receiver beams are formed at a time: sum, azimuth difference, elevation difference, and perhaps, additional difference beams, at angles other than azimuth (=0 degrees) and elevation (=90 degrees). Monopulse is applied at angles other than 0 and 90 degrees (for example 0, 45, 90, and 135 degrees) in order to locate a vessel in a direction perpendicular to the vessel. When the desired (i.e. peak) blood velocity signal is not in the output, this is instantly recognized (e.g., a monopulse ratio, formed after Doppler filtering, becomes non-zero) and the array is used to track (slow movement) or re-acquire (fast movement) the desired signal. Re-acquisition is achieved by returning to step one to form and Doppler-process a plurality of beams in order to select the beam (and the time delay or "range gate") with the most high-Doppler (high blood velocity) energy. This is followed by post-Doppler monopulse tracking to lock a beam and range gate on to the exact location of the peak velocity signal. In applications such as transcranial Doppler, where angular resolution based on wavelength and aperture size is inadequate, fine mapping is achieved, for example, by post-Doppler monopulse tracking each range cell of each vessel, and recording the coordinates and monopulse-pair angle describing the location and orientation of the monopulse null. With a three-dimensional map available, true vector velocity can be computed. For accurate vector flow measurement, the monopulse difference is computed in a direction orthogonal to the vessel by digitally rotating until a line in the azimuth-elevation or C-scan display is parallel to the vessel being monitored. The aperture is more easily rotated in software (as opposed to physically rotating the transducer array) if the aperture is approximately circular (or eliptical) rather than square (or rectangular). Also, lower sidelobes result by removing elements from the four corners of a square or rectangular array in order to make the array an octagon.

In this invention, as long as (1) a blood vessel or (2) a flow region of a given velocity can be resolved by finding a 3-D resolution cell through which only a single vessel passes, that vessel or flow component can then be very accurately located within the cell. Monopulse is merely an example of one way to attain such sub-resolution accuracy (SRA). Other methods involve "super-resolution" or "parametric" techniques used in "modern spectral estimation", including the MUSIC algorithm and autoregressive modeling, for example. SRA allows an extremely accurate map of 3-D flow.

Furthermore, the present invention utilizes post-Doppler, sub-resolution tracking and mapping; it does Doppler processing first and uses only high Doppler-frequency data. This results in extended targets since the active vessels approximate "lines" as opposed to "points". In three-dimensional space, these vessels are resolved, one from another. At a particular range, the monopulse angle axis can be rotated (in the azimuth-elevation plane) so that the "line" becomes a "point" in the monopulse angle direction. That point can then be located by using super-resolution techniques or by using a simple technique such as monopulse. By making many such measurements an accurate 3-D map of the blood vessels results.

Methods for extending the angular field of view of the thinned array (that is limited by grating lobes) include (1) using multiple panels of transducers with multiplexed processing channels, (2) convex V-shaped transducer panels, (3) cylindrical shaped transducer panel, (4) spherical shaped transducer panel, and (5) negative ultrasound lens. If needed, moving the probe and correlating the sub-images can create a map of an even larger region.

Active digital beamforming can also be utilized, but the implementation depends on a choice to be made between wideband and narrowband implementations. If emphasis is on high resolution mapping of the blood vessels, then a wide bandwidth (e.g., 50% of the nominal frequency) is used for fine range resolution. If emphasis is on Doppler spectral analysis, measurement, and monitoring, the map is only a tool. In this case, a narrowband, low cost, low range-resolution, high sensitivity implementation might be preferred. A wideband implementation would benefit in performance (higher resolution, wider field of view, and reduced grating lobes) using time-delay steering while a narrowband implementation would benefit in cost using phase-shift steering. The invention can thus be described in terms of two preferred implementations.

In a wideband implementation, time delay steering can be implemented digitally for both transmit and receive by oversampling and digitally delaying in discrete sample intervals. In a narrowband implementation, (1) phase steering can be implemented digitally (digital beamforming) for both transmit and receive, and (2) bandpass sampling (sampling at a rate lower than the signal frequency) can be employed with digital down-conversion and filtering.

Accordingly, it is an object of the present invention to locate the point in three dimensional space having the greatest high-Doppler energy, and determining coordinates for that point. With that information, and the radial velocity of the blood flowing through the blood vessel at that point, a variety of blood flow parameters can be calculated at that point, including, but not limited to vector velocity of blood flow, volume of blood flow, or Doppler spectral distribution. The parameter being measured can be an instantaneous value, or an average value determined over a heart cycle.

It is also an object of the present invention to continuously track and map in vivo the point in three dimensional space having the greatest Doppler-energy, and using the coordinates to generate a three dimensional image of a blood vessel and blood flow therein that possess a much greater resolution than images generated using heretofore known Doppler ultrasound methods and devices.

It is yet another object of the present invention to provide a thinned array which does not utilize the number of element transducers as are required with heretofore known Doppler ultrasound devices. As a result, the decreased number of elements in the array decreases size of the array utilized and provides a patient being analyzed with mobility that would not be available if using conventional ultrasound devices to obtain blood flow parameters such as vector velocity, blood flow volume, and Doppler spectral distribution. The parameter being measured can be an instantaneous value, or an average value determined over a heart cycle.

These and other aspects of the present invention will be better appreciated by reference to the following drawings and Detailed Description.

BRIEF DESCRIPTION OF THE DRAWINGS

FIG. 2 shows a 64-element bistatic ultrasound transducer array example, where, with D=2d, the same elements are reconfigured differently for transmit and receive during the acquisition phase of operation. FIG. 2(a) shows the Receive Configuration, where all 64 elements receive at once. FIG. 2(b) shows the Transmit Configuration, where, during acquisition, the 16 sub-apertures transmit one at a time.

FIG. 3 is an example overall block diagram of a blood flow mapping monitor embodiment.

FIG. 4 illustrates ultrasound beam coverage for the TCD array example of FIG. 2. The left illustration shows 25 digitally beam-formed beams, as an example. On the right, is shown, for that example, the manner in which the transmit beam encompasses 21 receive beams in the acquisition mode.

FIG. 5 shows one-dimensional patterns for a bistatic transducer array with D=2 d as in FIG. 2. FIG. 5a (top) shows the transmit element pattern. FIG. 5b shows the receive Element Pattern and Array Pattern with the receiver beam steered to broadside (x=0). The Array Pattern has Grating Lobes (Receiver Ambiguities). FIG. 5c shows the resultant two-way beam pattern (product of all three patterns above). The Grating Lobes are suppressed.

FIG. 8 shows a one-dimensional representation of the example of FIG. 4. FIG. 8a shows the product of transmit and receive Element Patterns. FIG. 8b plots a set of five receive beams showing Grating Lobes of the Thinned Array. FIG. 8c plots the resultant two-way beams with Grating Lobes suppressed.

FIG. 10 shows the receiver channel signal spectrum illustrating functions performed by the FPGA of FIG. 9 on each of the 64 received signals for a narowband case.

FIGS. 26(a-f) show six different views of a combined transmit/receive according to an embodiment of the invention.

DETAILED DESCRIPTION OF THE INVENTION

Figure 1:
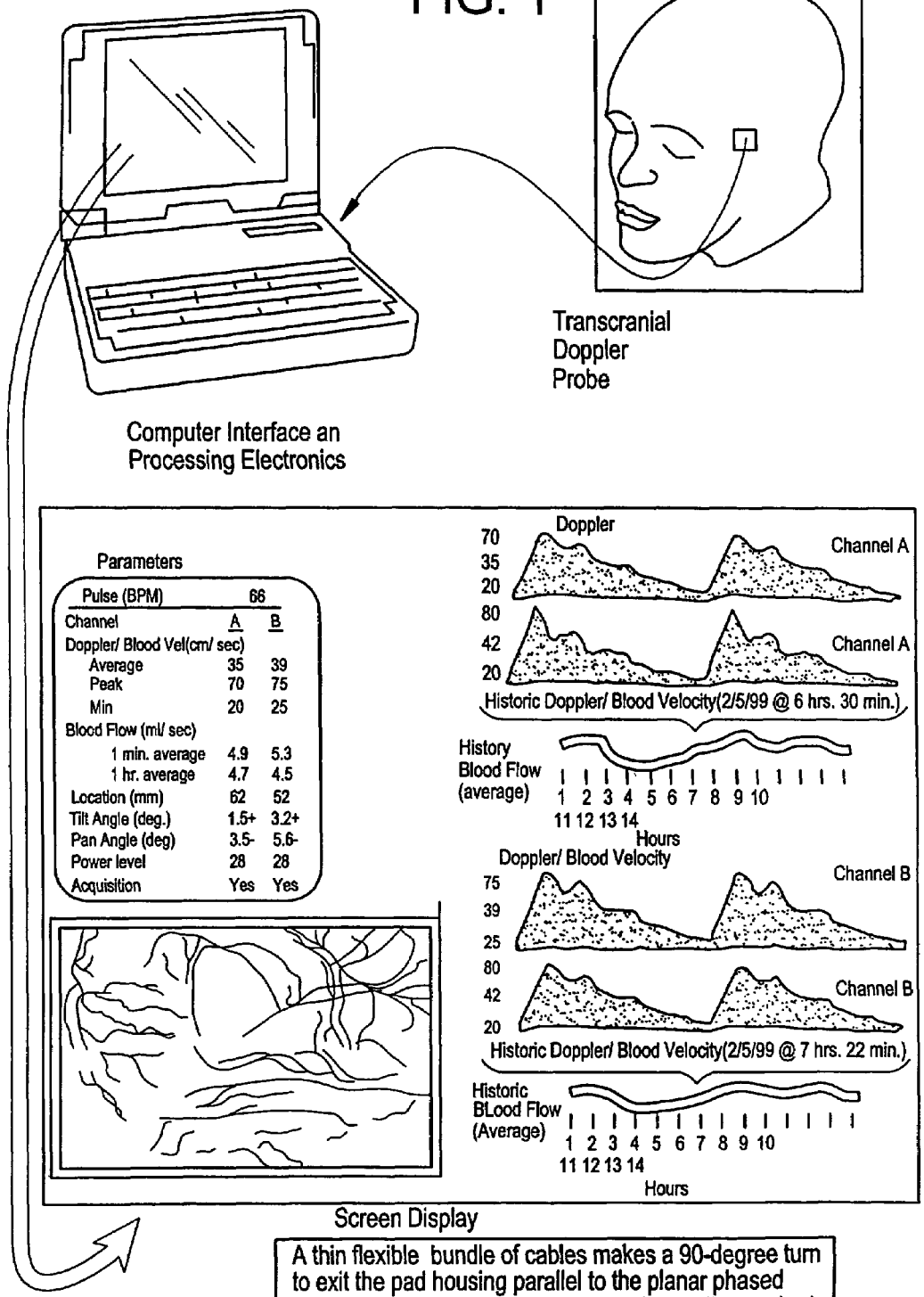
FIG. 1 illustrates the Blood Flow Mapping Monitor in use with a Transcranial Doppler Probe, as an example.

The invention involves (1) a family of ultrasound sensors, (2) the interplay of a set of core technologies that are unique by themselves, and (3) a number of design options which represent different ways to implement the invention. To facilitate an organizational understanding of this many-faceted invention, a discussion of each of the three topics above follows.

The sensors addressed are all two-dimensional (i.e., planar or on the surface of a convex shape such as a section of a cylinder) arrays of piezoelectric crystals for use in active, non-invasive, instantaneous (or real-time), three-dimensional imaging and monitoring of blood flow. The sensors use a unique approach to 3-D imaging of blood velocity and blood flow that (1) allows for finer image resolution than would otherwise be possible with the same hardware complexity (number of input cables and associated electronics) and (2) allows for finer accuracy than would ordinarily be possible based on the resolution. The invention measures and monitors 3-D vector velocity rather than merely the radial component of velocity.

Moreover, the present invention also utilizes (1) array thinning with large elements and limited scanning, (2) array shapes to reduce peak sidelobes and extend the field of coverage, (3) post-Doppler sub-resolution tracking, (4) post-Doppler sub-resolution mapping, (5) additional methods for maximizing the angular field of view, and (6) various digital beamforming procedures for implementing the mapping, tracking, and measurement processes. The present invention also extends to array thinning, where the separation between array elements is significantly larger than half the wavelength. This reduces the number of input cables and input signals to be processed while maintaining high resolution and sensitivity and avoiding ambiguities. In a transcranial Doppler application, for example, where signal to noise and hence receiver array area is of paramount importance, array thinning is possible without reducing the receiver array area because a relatively small (compared to other applications) angular field of view is needed.

Thinning with full aperture area imposes limitations on the angular field of view. Methods for expanding the field of view include using more elements than are active at any one time. For example, if the electronics are switched between two identical panels, the cross-range field of view at any depth is increased by the size of the panel. If the panels are pointed in slightly different directions so that overlapping or redundant beams are avoided, the field of view is doubled. A generalization of this approach involves the use of an array on a cylindrical or spherical surface.

Once a section of a blood vessel is resolved from other vessels in Doppler, depth, and two angles (az and el), Post-Doppler sub-resolution processing locates that section to an accuracy that is one-tenth to one-twentieth of the resolution. This allows for precise tracking and accurate mapping. Tracking provides for the possibility of unattended long term monitoring and mapping aids the operator in selecting the point or points to be monitored.

Furthermore, methods of the present invention permit non-invasive, continuous, unattended, volumetric, blood vessel tracking, ultrasound monitoring and diagnostic device for blood flow. It will enable unattended and continuous blood velocity measurement and monitoring as well as 3-dimensional vascular tracking and mapping using an easily attached, electronically steered, transducer probe that can be in the form of a small pad for monitoring application, when desired. Moreover, a device and method of the present invention have applications in measuring the parameters described above in any part of the body. A nonlimiting example described below involves a cranial application. However as set forth, a device and method of the present have applications in any part of the body, and can be used to track and map any blood vessel in the body. A device of the present invention can, for example:

1. Measure and continuously monitor blood velocity with a small low-profile probe that can be adhered, lightly taped, strapped, banded, or otherwise easily attached to the portion of the body where the vascular diagnosis or monitoring is required.
2. Track and maintain focus on multiple desired blood vessels in spite of movement.
3. Map 3-D blood flow; e.g., in the Circle of Willis (the central network of arteries that feeds the brain) or other critical vessels in the cranial volume.
4. Perform color velocity imaging and display a 3-D image of blood flow that is rotated via track ball or joystick until a desired view is selected.
5. Form and display a choice of projection, slice, or perspective views, including (1) a projection on a depth-azimuth plane, a B-scan, or a downward-looking perspective, (2) a projection on an azimuth-elevation plane, a C-scan, or a forward-looking perspective, or (3) a projection on an arbitrary plane, an arbitrary slice, or an arbitrary perspective.
6. Use a track ball and buttons to position circle markers on the points were measurement or monitoring of vector velocity is desired.
7. Move the track location along the blood vessel by using the track ball to slide the circle marker along the image of the vessel.
8. Display actual instantaneous and/or average vector velocity and/or estimated average volume flow.
9. Maintain a multi-day history and display average blood velocity versus time for each monitored vessel over many hours.
10. Sound an alarm when maximum or minimum velocity is exceeded or when emboli count is high; and maintain a log of emboli detected.
11. Track, map, and monitor small vessels (e.g., 1 mm in diameter), resolve vessels as close as 4 mm apart (for example), and locate them with an accuracy of ±0.1 mm, for example.

Moreover, as explained herein, numerous methods have applications in obtaining the three dimensional coordinates of points along a blood vessel from echoes returned from the body, and are encompassed by the present invention. A particular nonlimiting example of such a method having applications herein is a novel and unobvious variation of monopulse tracking. For tracking purposes utilizing monopulse, up to nine beams are simultaneously formed for each transmit beam position. In addition to the "sum" beam that corresponds to the transmitted beam, there will either be 4 monopulse difference beams or there will be 8 overlapping focused beams. If a cluster of eight focused beams is used, these will be highly overlapped with the sum beam, and displaced very slightly from the sum beam, with their centers equally spaced on a small circle around the center of the sum beam. These satellite beams would then operate in pairs to form four difference beams. For example, the azimuth Monopulse ratio can be produced in two different ways, which will call "liner" and "non-linear". The non-linear method will determine the magnitudes or the powers of three received signals, left, right, and sum (L, R, and S), and compute $M_a=(|L|-|R|)/|S|$. The linear method uses complex signals and computes the azimuth monopulse ratio as the real part of the ratio $D_a/S$, where $D_a=L-R$. $D_a$ is the azimuth difference.

For an ideal point target, the linear method for computing $M_a$ results in an excellent estimate of the azimuth angle error. It also has the advantage of only requiring 4, instead of 8 auxiliary beams. These 4 beams would be an azimuth difference beam, $D_a$, an elevation difference beam, and two diagonal difference beams. The individual beams, such as L and R, are not needed. However, beam shapes will be highly distorted by refraction through bone and tissue, and a "sub-optimum" non-linear approach might be more robust.

Regardless of which monopulse method is used, the conventional two difference beams used in radar (azimuth difference and elevation difference) may not be enough. The projection of the high-velocity data on a plane perpendicular to the transducer line of sight (the C-scan) will usually be a line, not a point. With multiple difference beams, equally spaced in angle, one will be approximately perpendicular to the C-scan projection of the vessel. The system will select the monopulse difference output with the largest magnitude. This provides an approximate orientation of the C-scan projection of the vessel. The corresponding monopulse ratio (provided the sum beam power exceeds a threshold) is used to correctly re-steer and maintain a beam precisely centered on that vessel.

If the power map output of a Wall filter is used for the monopulse beams, the beam outputs are power and hence a complex ratio is not available. In that case the nonlinear method would be used. An alternative is to use the complex wall filter output, before computing the power, with the linear method. During measurement, however, the output of a particular (high velocity) FFT Doppler bin may be used for monopulse (provided that the magnitude or power of he sum beam at that Doppler exceeds a threshold). In that case either the linear or the nonlinear monopulse ratio may be used.

Another alternative is to use FFT processing and form the monopulse ratio (linearly or non-linearly) at the output of a high-velocity Doppler-frequency cell with high sum-beam power. For example, set a power threshold and select the highest (positive or negative) velocity cell with power that exceeds the threshold. Since the data in a single FFT cell is expected to be noisy, this procedure is recommended for a measurement dwell, where enough time is spent in a single beam position to have both useable velocity resolution and the ability to make several measurements (multiple FFT's per frame).

FFT-Based Monopulse and Monopulse Averaging During Measurement

In a K pulse dwell, let $K=K_1 \times K_2$, where $K_1$ is the number of input pulses used in the FFT and $K_2$ is the number of FFT's. Instead of performing monopulse to re-steer the beam every $K_1$ pulses, we compute the monopulse ratio at the output of a desired high velocity Doppler bin, and average its value over $K_2$ FFT's. This reduces the steering noise while assuring that we are locating the center of the vessel (the highest Doppler Energy). We chose the highest Doppler frequency for which the minimum sum beam power exceeds a threshold, and utilize only that Doppler cell for monopulse. The average is best performed as a weighted average. For example, if $D_n$ and $S_n$ are (say, elevation) difference-beam and sum beam outputs in the nth FFT for the selected Doppler bin, we chose:

$$M = \frac{\sum_{n=1}^{K_2} |S_n|^2 M_n}{\sum_{n=1}^{K_2} |S_n|^2}, \text{ where } M_n = \text{Re}\{D_n/S_n\}$$

$$\text{or } M_n = \frac{|D_n|^2}{|S_n|^2}$$

depending on whether linear or non-linear monopulse is used. For linear monopulse it might be best to use only one large FFT ($K_2=1$). For non-linear monopulse, the expression simplifies to:

$$M = \frac{\sum_{n=1}^{K_2} |D_n|^2}{\sum_{n=1}^{K_2} |S_n|^2}$$

[Note that because a ratio is involved (so that beam pointing error is not confused with signal strength) even the "linear" method is non-linear.]

A device of the present invention will allow a person with little training to apply the sensor and position it based on an easily understood ultrasound image display. The unique sensor can continuously monitor artery blood velocity and volume flow for early detection of critical events. It will have an extremely low profile for easy attachment, and can track selected vessels; e.g., the middle cerebral artery (MCA), with no moving parts. If the sensor is pointed to the general volume location of the desired blood vessel (e.g., within ±1 cm.), it will lock to within ±0.1 mm of the point of maximum radial component of blood flow and remain locked in spite of patient movement.

A device of the present invention can remain focused on the selected blood vessels regardless of patient movement because it produces and digitally analyzes, in real time, a 5-dimensional data base composed of signal-return amplitude as a function of:
1. Depth,
2. Azimuth,
3. Elevation,
4. Radial component of blood velocity,
5. Time.

Since a device of the present invention can automatically locate and lock onto the point with the maximum volume of blood having a significant radial velocity, unattended continuous blood velocity monitoring is one of its uses. By using the precise relative location of the point at which lock occurs as a function of depth, a device of the present invention can map the network of blood vessels as a 3-dimensional track without the hardware and computational complexity required to form a conventional ultrasound image. Using the radial component of velocity along with the three-dimensional blood path, a device of the present invention can directly compute vector velocity.

A device used in a method of the present invention is a non-mechanical Doppler ultrasound-imaging sensor comprising probes, processing electronics, and display. Specific choices of probes allow the system to be used for transcranial Doppler (TCD), cardiac, dialysis, and other applications.

The present invention may be better understood by reference to the following non-limiting Examples, which are provided as exemplary of the invention. The following Examples are presented in order to more fully illustrate particular embodiments of the invention. They should in no way be construed, however, as limiting the broad scope of the invention.

EXAMPLE 1

An Ultrasound Diagnostic and Monitoring Sensor with Real-Time 3-D Mapping and Tracking of Blood Flow This embodiment of the present invention has application for medical evaluation and monitoring multiple locations in the body; however, the transcranial Doppler application will be used as an example to describe the invention.

This invention provides: (1) affordable three-dimensional imaging of blood flow using a low-profile easily-attached transducer pad, (2) real-time vector velocity, and (3) long-term unattended Doppler-ultrasound monitoring in spite of motion of the patient or pad. None of these three features are possible with current ultrasound equipment or technology.

The pad and associated processor collects and Doppler processes ultrasound blood velocity data in a three dimensional region through the use of a planar phased array of piezoelectric elements. Through use of unique beamforming and tracking techniques, the invention locks onto and tracks the points in three-dimensional space that produce the locally maximum blood velocity signals. The integrated coordinates of points acquired by the accurate tracking process is used to form a three-dimensional map of blood vessels and provide a display that can be used to select multiple points of interest for expanded data collection and for long term continuous and unattended blood flow monitoring. The three dimensional map allows for the calculation of vector velocity from measured radial Doppler.

A thinned array (greater than half-wavelength element spacing of the transducer array) is used to make the device inexpensive and allow the pad to have a low profile (fewer connecting cables for a given spatial resolution). The same physical array can also be used to form a broad transmit beam encompassing a plurality of narrow receive beams. Initial acquisition of the blood velocity signal is attained by insonating a large region by defocusing the transmit array or by using a small transmitting sub-aperture, for example. The computer simultaneously applies numerous sets of delays and/or complex weights to the receiver elements in order to form M simultaneous beams. With M beams being formed simultaneously, the receiver can dwell M times as long, so as to obtain high S/N and fine Doppler resolution. For an embodiment that utilizes a small transmitting sub-aperture, the source of the transmitted energy within the array (i.e., the location of the transmitter sub-aperture) varies with time in order to lower the temporal average spatial peak intensity to prevent skin heating.

The array is thinned without reducing the receiver area by limiting the angular field of view. When needed, a map of a larger region is created by moving the probe and correlating the sub-images. Once the region of interest has been imaged and coarsely mapped, the full transmitter array is focused at a particular location on a particular blood vessel for tracking. In the tracking mode: (1) grating lobes due to array thinning are reduced by using wide bandwidth and time delay steering and (2) only three beams are formed at a time: sum, azimuth difference, and elevation difference. When the desired (i.e. peak) blood velocity signal is not in the output, this is instantly recognized (e.g., a monopulse ratio, formed after Doppler filtering, becomes non-zero) and the array is used to track (slow movement) or re-acquire (fast movement) the desired signal. Re-acquisition is achieved by returning to step one to form and Doppler-process a plurality of beams in order to select the beam (and the time delay or "range gate") with the most high-Doppler (high blood velocity) energy. This is followed by post-Doppler monopulse tracking in azimuth, elevation, and range to lock a beam and range gate on to the exact location of the peak velocity signal.

In applications such as transcranial Doppler, where angular resolution based on wavelength and aperture size is inadequate, fine mapping is achieved, for example, by post-Doppler monopulse tracking each range cell of each vessel, and recording the coordinates describing the location of the monopulse null. With a three-dimensional map available, true vector velocity can be computed. For accurate vector flow measurement, the monopulse difference is computed in a direction orthogonal to the vessel by digitally rotating until a line in the azimuth-elevation or C-scan display is parallel to the vessel being monitored.

All current ultrasound devices (including "Doppler color flow mapping" systems) form images that are limited by their resolution. In some applications, such as TCD, the low frequency required for penetration makes the azimuth and elevation resolution at the depths of interest larger than the vessel diameter. In this invention, as long as (1) a blood vessel or (2) a flow region of a given velocity can be resolved by finding a 3-D resolution cell through which only a single vessel passes, that vessel or flow component can then be very accurately located within the cell. Monopulse is merely an example of one way to attain such sub-resolution accuracy (SRA). SRA allows an extremely accurate map of 3-D flow.

This invention utilizes post-Doppler, sub-resolution tracking and mapping; it does Doppler processing first and uses only high Doppler-frequency data. This results in extended targets since the active vessels approximate "lines" as opposed to "points". In three-dimensional space, these vessels are resolved, one from another. At a particular range, the azimuth-elevation axis can be rotated so that the "line" becomes a "point" in the azimuth dimension. That point can then be located by using super-resolution techniques or by using a simple technique such as monopulse.

Overview of the Embodiment

The invention is complex because it involves (1) a family of ultrasound sensors (for different parts of the body), (2) the interplay of a set of core technologies that are unique by themselves, and (3) a number of design options which represent different ways to implement the invention. To facilitate an organizational understanding of this many-faceted invention, we precede a description of an overall preferred embodiment with a discussion of each of the three topics above.

The sensors addressed are all two-dimensional (i.e., planar) arrays of piezoelectric crystals for use in active, non-invasive, instantaneous (or real-time), three-dimensional imaging and monitoring of blood flow. While the sensors and the techniques for their use apply to all blood vessels in the body, the figures and detailed description emphasizes the transcranial Doppler (TCD) monitor because that application is most difficult to implement without all of the components of this invention. The sensors use a unique approach to 3-D imaging of blood velocity and blood flow that (1) allows for finer image resolution than would otherwise be possible with the same hardware complexity (number of input cables and associated electronics) and (2) allows for finer accuracy than would ordinarily be possible based on the resolution. The invention measures and monitors 3-D vector velocity rather than merely the radial component of velocity.

The core technologies that constitute the invention are (1) array thinning with suppression of ambiguities or grating lobes, (2) post-Doppler sub-resolution tracking, and (3) post-Doppler sub-resolution mapping. The invention encompasses two ways to thin the array (reducing the number of input cables and input signals to be processed while maintaining high resolution and avoiding ambiguities). The first is bistatic operation; the second is broadband operation. In the TCD application, where signal to noise and hence receiver array area is of paramount importance, array thinning is possible without reducing the receiver array area because a relatively small (compared to other applications) angular field of view is needed. One particular bistatic approach to thinning reduces transmitter area and consequently poses a problem of excessive spatial peak intensity (skin heating) in the TCD application. This is solved by a component invention called transmitter diversity (which lowers the temporal average of the spatial peak intensity). The phase-defocusing bistatic approach and the monostatic or bistatic broadband approach to thinning all use the entire aperture and hence do not require transmitter diversity.

In the TCD application, the achievable angular resolution is poor, regardless of the method of thinning, or whether or not thinning is used. Once a section of a blood vessel is resolved from other vessels in Doppler, depth, and two angles (az and el), Post-Doppler sub-resolution processing locates that section to an accuracy that is 10 to 20 times as fine as the resolution. This allows for precise tracking and accurate mapping. Tracking provides for the possibility of unattended long term monitoring and mapping aids the operator in selecting the point or points to be monitored.

There are many options available in the design of any member of the family of sensors that utilizes any or all of the core technologies that comprise this invention. A two-dimensional array is established art that can be designed in many ways and can have many sizes and shapes (rectangular, round, etc.). Digital beamforming (DBF) is a technique that has been in the engineering literature (especially radar and sonar) for many years. One medical ultrasound DBF patent cites many references, while another describes a particular instance of DBF without citing the other patent or any other prior art. While planar arrays, DBF, Doppler ultrasound, and color flow imaging are prior art, the manner in this specification of using such established technologies to map, track, measure, and monitor blood flow is unique.

The embodiment is a non-invasive, continuous, unattended, volumetric, blood vessel tracking, ultrasound monitoring and diagnostic device. It will enable unattended and continuous blood velocity measurement and monitoring as well as 3-dimensional vascular tracking and mapping using an easily attached, electronically steered, transducer probe that can be in the form of a small pad for monitoring application, when desired. Although the device has application to multiple body parts, the cranial application will be used as a specific example. The device can, for example:

1. Measure and continuously monitor blood velocity with a small low-profile probe that can be adhered, lightly taped, strapped, banded, or otherwise easily attached to the portion of the body where the vascular diagnosis or monitoring is required.
2. Track and maintain focus on up to four desired blood vessels in spite of movement.

3. Map 3-D blood flow; e.g., in the Circle of Willis (the central network of arteries that feeds the brain).
4. Perform color velocity imaging and display a 3-D image of blood flow that is rotated via track ball or joystick until a desired view is selected.
5. Form and display a choice of projection, slice, or perspective views, including (1) a projection on a depth-azimuth plane, a B-scan, or a downward-looking perspective, (2) a projection on an azimuth-elevation plane, a C-scan, or a forward-looking perspective, or (3) a projection on an arbitrary plane, an arbitrary slice, or an arbitrary perspective.
6. Use a track ball and buttons to position circle markers on the points at which we wish to measure and monitor vector velocity.
7. Move the spatial resolution cell being measured along the blood vessel by using the track ball to slide the circle marker along the image of the vessel.
8. Display actual instantaneous and/or average vector velocity and/or estimated average volume flow.
9. Maintain a 3-day history and display average blood velocity versus time for each monitored vessel over 14 hours.
10. Sound an alarm when maximum or minimum velocity is exceeded or when emboli count is high.
11. Track, map, and monitor vessels as small as 1 mm in diameter, resolve vessels as close as 4 mm apart (for example), and locate them with an accuracy of ±0.1 mm.

The Monitoring Device will allow a person with little training to apply the sensor and position it based on an easily understood ultrasound image display. The unique sensor can continuously monitor artery blood velocity and volume flow for early detection of critical events. It will have an extremely low profile for easy attachment, and can track selected vessels; e.g., the middle cerebral artery (MCA), with no moving parts. If the sensor is pointed to the general volume location of the desired artery (e.g., within ±0.5 cm.), it will lock is to within ±0.1 mm of the point of maximum radial blood flow and remain locked in spite of patient movement.

The device can remain focused on the selected blood vessels regardless of patient movement because it produces and digitally analyzes, in real time, a 5-dimensional data base composed of signal-return amplitude as a function of:
6. Depth, 2. Azimuth, 3. Elevation, 4. Radial blood velocity, 5. Time.

Since the device can automatically locate and lock onto the point with the maximum volume of blood having a significant radial velocity, unattended continuous blood velocity monitoring is one of its uses. By using the precise relative location of the point at which lock occurs as a function of depth, the device can map the network of blood vessels as a 3-dimensional track without the hardware and computational complexity required to form a conventional ultrasound image. Using radial velocity along with the three-dimensional blood path, the device can directly compute vector velocity.

The proposed device is a non-mechanical Doppler ultrasound-imaging sensor consisting of probes, processing electronics, and display. Specific choices of probes allow the system to be used for transcranial Doppler (TCD), cardiac, dialysis, and other applications.

FIG. 1 shows the TCD configuration and the initial definition of the display screen. The TCD system is comprised of one or two probes attached to the head with a "telephone operator's band" or a Velcro strap. The interface and processing electronics is contained within a small sized computer. A thin cable containing 64 micro coax cables attaches the probe to the electronics in the computer. When the operator positions the probe on the head the Anterior, Middle and Posterior Cerebral Arteries and the Circle of Willis are imaged on the screen along with other blood vessels. The arteries or vessels of interest are selected by viewing the image. The system locks onto the blood vessels and tracks their position electronically. A variety of selected parameters is presented on the screen; e.g., the velocity, the pulse rate, depth of region imaged, gain and power level. Using only one probe the TCD can monitor up to two arteries (vessels) at a time. Presented on the screen are dual traces, one for each artery. The blood velocity can be dynamically monitored. As shown in FIG. 1 both the current blood velocity (dark traces) and any historic trace (lighter color) can be displayed simultaneously. The average blood velocity or estimated average flow for each artery is displayed below the respective velocity trace. The image shows the arteries and the channel used for each artery. When two probes are used, the display is split showing signals from both of them. Using a different probe (i.e., different size) with the same electronics and display, the unit can be used to measure and monitor the blood flow in a carotid artery. Similarly, it can be used to perform this function for dialysis, anesthesia, and in other procedures.

The sensor is a two dimensional array of transducer elements (piezoelectric crystals) that are configured and utilized differently for transmit and receive during acquisition. For example, if a square (N×N) array is used, all $N^2$ elements would receive at the same time, but only a 2×2 sub-aperture would transmit at any one time. This is illustrated in FIG. 2 for the case of N=8. The array need not be square. Any M×N array may be utilized in this manner. All NM received signals (64 in our example) are sampled, digitized, and processed. This can be done, for example, in a desk top or lap top personal computer with additional cards for electronics and real-time signal processing as illustrated in FIG. 1 and FIG. 3. If the PCI bus in FIG. 2 becomes a bottleneck for high speed processing, a pipelined or systolic architecture would be used. Alternatively, the processing can be performed in an application specific integrated circuit (ASIC).

The small (4 element) transmit sub-aperture (FIG. 2b) produces a broad transmit beam that insonates a region containing many receive beams. This is schematically illustrated in FIG. 4 for the particular case of a square array and square elements such as in FIG. 2. Since data is received from each element of the array, this data can be combined in a processor (FIG. 3, for example) in many different ways to form any number of beams. The transmitter is larger than a single array element so that it can provide some selectivity and not insonate the grating lobes caused by array thinning (spacing the array elements more than ½ wavelength apart). The concept is illustrated below for a 1-dimensional array forming a beam that measures only one angle. For a two-dimensional array, this represents a horizontal or vertical cut through the cluster of beams shown in FIG. 4. FIG. 4 was an approximate and conceptual representation of the two-angle (azimuth and elevation) extension of the single angle case detailed below.

"Grating lobes" are ambiguities or extra, unwanted, beams caused by using a transducer array whose elements are too large and hence too far apart. The following analysis illustrates grating lobe suppression for the worst case of narrowband signals and phase-shift beam processing. Time delay processing using wideband signals would be similar, but would further attenuate or eliminate grating lobes, resulting in even better performance.

The next four figures show beam pattern amplitudes plotted against $$x = (d/\lambda) \sin \theta, \qquad (1)$$

where x represents a normalization for the angle, $\theta$, from which reflected acoustic energy arrives. The azimuth (or elevation) angle, $\theta$, is zero in the broadside direction, perpendicular to the transducer array. The width (or length) of a transmitter is 2d, where d is the width (or length) of a single element of the receiver array. The wavelength of the radiated acoustic wave is $\lambda=c/f$, where c is the acoustic propagation velocity (1540 meters/second in soft tissue) and f is the acoustic frequency (usually between 1 and 10 megahertz). FIG. 5a shows the transmitter pattern $$a_T(x) = \sin 2\pi x / 2\pi x \qquad (2)$$

for the special case of uniform insonation over the 2d-wide transmitter sub-aperture being used.

The receiver pattern is the product of the receiver element pattern and the receiver array pattern $$a_R(x) = a_{RE}(x) a_{RA}(x) \qquad (3)$$

Each of these two component patterns is plotted separately in FIG. 5b. Again assuming the special case of a uniform receiver element (and a square element in the case of a 2-D array), the receive element pattern is $$a_{RE}(x) = \sin \pi x / \pi x. \qquad (4)$$

The receiver element pattern is twice as wide as the transmitter pattern because the receiver element is half as wide as the transmitter. In the far-field, i.e., for $\lambda r >> L^2$, where r is the range or depth and L is the length of the aperture, the receive array pattern steered to the angle $\theta = \theta_0$ is $$a_{RA}(x) = \sum_{n=0}^{N-1} w_n e^{j2\pi n(x-x_0)}, \qquad (5)$$

where $w_n$ is a weighting to reduce sidelobes and N is the number of elements in one dimension. As seen in FIG. 5b, equation (5) is periodic in x. The peak at $x=x_0$ ($x_0=0$ in FIG. 5) is the desired beam and the others are grating lobes.

In the near field, when focused at $(r_0, \theta_0)$, equation (5) is replaced by the slightly better general Fresnel approximation:

$$a_{RA}(x, z) = \sum_{n=0}^{N-1} w_n e^{j2\pi \left[n(x-x_0) + \left(n - \frac{N-1}{2}\right)^2 (z-z_0)\right]} \qquad (6)$$

(provided that the range significantly exceeds the array size, r>L), where $x = d \sin \theta / \lambda$, as before, and $$z = d^2 \cos^2 \theta / \lambda r. \qquad (7)$$

Because the receiver aperture is sampled with a spatial period of d, the receiver array pattern will be periodic in $\sin \theta$, with a period of $\lambda/d$ (equation 5).

This periodicity means that the array pattern is ambiguous. When the array is pointed broadside ($\theta=0$), it will also be pointed at the angle $\theta = \sin^{-1}(\lambda/d)$, for example. In terms of the normalized variable, x, the period is unity. Since $|\sin \theta|$ cannot exceed 1, the variable x is confined to the interval $[-d/\lambda, d/\lambda]$.

The conventional element spacing is $d = \lambda/2$. Thus, in a conventional phased array, x is always between $-0.5$ and $+0.5$, and hence ambiguities are not encountered. In a highly thinned array ($d > \lambda$), there will normally be ambiguities or grating lobes as illustrated in FIG. 5b. The second grating lobe, at $x=2$ or $\theta = \sin^{-1}(2 \lambda/d)$, is not real when d does not exceed $2\lambda$.

FIG. 5c shows the two-way pattern. The gating lobe suppression, resulting from the choice of a transmitter diameter of D=2d is valid for all values of d. In a two dimensional array, the elements could be rectangular instead of square ($d_x \times d_y$), and the results would still be valid. Similar results could be obtained for an array in which the elements are staggered from row to row (and/or column to column). For example, if the receiver array is a "bathroom tile" of hexagonal elements, the transmitters could be chosen as sub-arrays consisting of an element and its six surrounding neighbors.

Figure 6A:
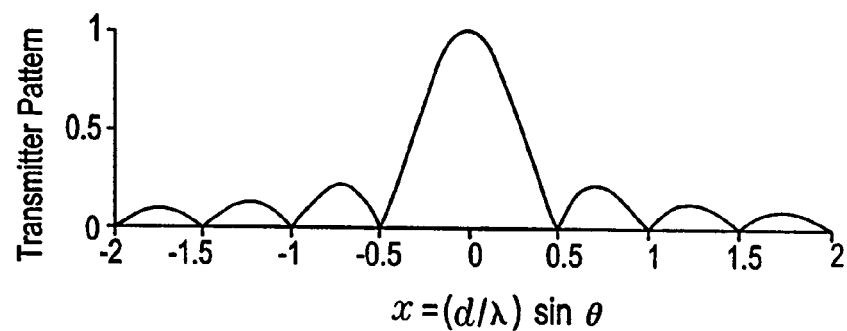
FIG. 6 is the same as FIG. 5, with the receive array beam steered to x=0.2.
Figure 6B:
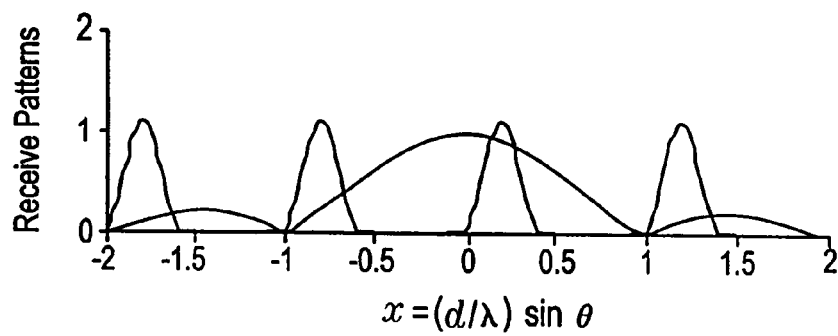
Figure 6C:
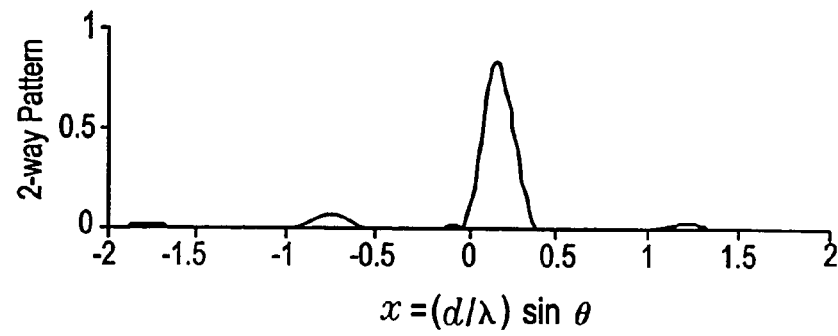
Figure 7:
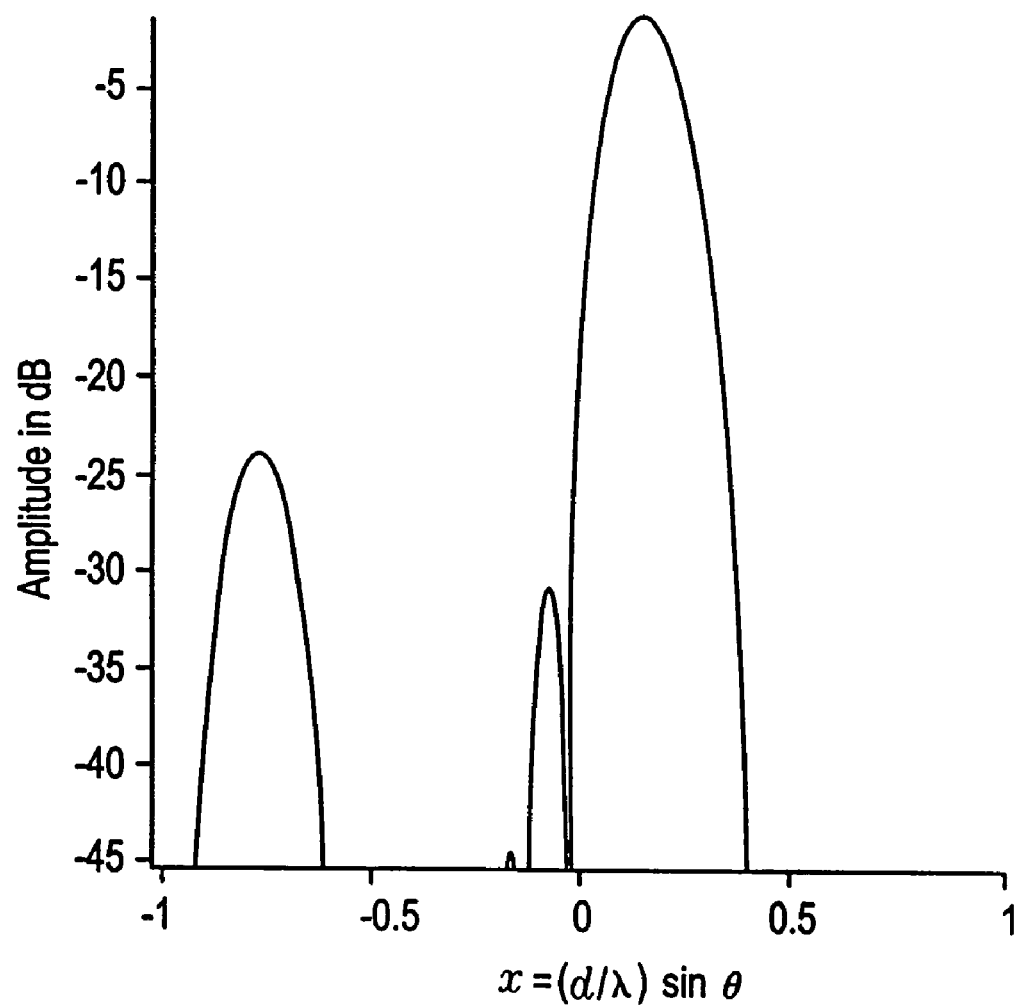
FIG. 7 shows the Two-way pattern of a receiver beam steered to the half power point (x=0.2). This is FIG. 6c plotted in dB.

In FIG. 6 the same array is used as in FIG. 5, but the receiver element signals are combined with a phase taper that steers the beam to $x=0.2$. This is approximately (a little less than) the half power point, where $a_t(x) a_{re}(x)=0.707$. In FIG. 6c, we see that the grating lobes are not completely suppressed, with the largest one at $x=-1+0.2=-0.8$. FIG. 7 shows this in decibels. The worst-case grating lobe is attenuated by at least 25 dB, even in the stressing case of extremely narrow band operation. A Hanning window was applied to keep the sidelobes lower than the peak grating lobe. These Figures were produced in MATLAB, using the following software (m-file):

x=-2:1/64:2-1/64;
p=pi*x+eps; R=sin(p)./p;
p=2*p; T=sin(p)./p;
N=8
n=0:N-1;
% xo=0;
xo=0.2; % is 2-way 1/2 power
e=exp(j*n'*2*pi*(x-xo));
w=hanning(N);
% E=(1/N)*ones(1,N)*e;
E=(2/N)*w'*e;
subplot(311); plot(x,abs(T));
subplot(312); plot(x,[abs(R);abs(E)]);
TRE=abs(T).*abs(R).*abs(E);
subplot(313); plot(x,TRE);
figure(2); plot(x,20*log10(TRE));
zoom on;

The dimensions in FIG. 4 are representative for a transcranial Doppler application of the invention, to provide a specific example. If f=2 MHz is chosen for the center frequency, the wavelength is 0.77 mm. An 8×8 array with a width and/or length of L=1 cm, provides a one dimensional thinning ratio of $2 d/\lambda = 3.247$. For a square array, the total number of elements is reduced by a factor of $(2 d/\lambda)^2 \geq 10$ from that of a filled array. Even greater thinning ratios are possible. Even if $d/\lambda$ is kept less than 2 to avoid a second grating lobe (at x=2), complexity reductions up to a factor of 16 are possible. For the 1 cm array at 2 MHz, the hyperfocal distance (where the 3 dB focal region extends to infinity) is $L^2/4\lambda = 3.25$ cm. Thus, a fixed focus probe suffices for this application. However, since the simultaneous formation of multiple receive beams is conveniently performed digitally, dynamic focus on receive is easily accomplished. The quadratic phase distribution across the elements required to focus in depth is simply added to the linear phase distributions required to steer the beams.

FIG. 8a shows the product of the transmitter pattern (FIG. 5a or 6a) and the receiver element pattern. FIG. 8b plots the element patterns for a set of five beams steered to x=-0.2, -0.1, 0, 0.1, and 0.2. This set of five receive beams shows grating lobes of the thinned array. FIG. 8c shows the set of resulting 2-way patterns obtained by multiplying the patterns in FIG. 8b by the function plotted in FIG. 8a. Here, the grating lobes are suppressed. This represents a horizontal or vertical cut through the cluster of beams in FIG. 4.

Using the configuration described above, the cluster of beams in FIGS. 4 and 8c is used to approximately locate the desired point for collecting the blood velocity signal. For example the output of each beam in the cluster would be Doppler processed by performing an FFT or equivalent transformation on a sequence of pulse returns. The pulse repetition frequency (PRF) would typically be less than or equal to 9 kHz to unambiguously achieve a depth of 8.5 cm for the TCD application. In order to obtain a velocity resolution as fine as $\Delta v=1$ cm per second (to distinguish brain death), a dwell of duration $T=\lambda/(2\Delta v)=38.5$ ms, or 347 pulses at 9 kHz, is desired. For efficient FFT processing, the number of pulses used would be zero filled to a power of 2 such as 512.

The example shown in FIGS. 2 through 8 was an 8 by 8 receiver array forming a 5 by 5 cluster of beams. This is an example of an approximate rule of thumb for this invention, that an N element linear array is recommended for use in producing N/2+1 beams for N even and [N+1]/2 beams for N odd. Thus, a 16 by 10 element rectangular array would preferably be used to form a 9 by 6 cluster of beams, though the actual number of beams formed is arbitrary. This recommended number of beams is derived below.

If an N elements were used to form orthogonal beams, e.g., by an N-point FFT, then there would be N beams in a 1800 angular region, from $-90°$ to $+90°$, corresponding to $-1<u<1$, where $u=\sin\theta$. In conventional phased array ultrasound, a 128 ($=N$) element array is used to produce 256 ($=2N$) lines (sequentially scanned beams) in a 90° angular region from $-45°$ to 45°, corresponding to $-0.707<u<0.707$. If the array is filled, then $x=u/2$ (Equation 1) and 2N beams are conventionally formed in $|x|<\sqrt{2}/4$. When we thin the array, we prefer to have $|x|<0.2=1/5$ (the 3 dB point of the curve in FIG. 7a). The number of beams in that region, for the same beam density as used in current practice, is given by Recommended No. of beams=$(1/5)N\div(\sqrt{2}/4)=2\sqrt{2}$
$N/5\approx 0.5657\ N.$ The beams are formed digitally, using software on a personal computer or using digital signal processing hardware to implement equations such as Equation 5 or 6. The electronic interface between the probe and the processor is diagrammed in FIG. 9. This figure illustrates the case of signals from 64 elements being connected to a single A/D converter, and power being applied to sets of four elements. The use of a separate A/D converter for every received channel, for example, is another possible implementation of this invention.

A conventional, half-wavelength spaced, monostatic, phased array could sequentially search a region of interest, but it would require far more elements and would thus be far more costly. Using the array differently in transmit and receive, not only allows for the formation of multiple beams; it also enables the use of the angular pattern of the transmitter to suppress receiver grating lobes. This allows for a "thinned" array (elements spaced less than a half wavelength apart). Because receive beams are formed only in a limited angular region, a wide-angle receiver element pattern (which usually implies a small element) is not required. In fact, the size of the receiver element can be as large as the element spacing. Thus the receiver array is "thinned" only in the sense that the element spacing exceeds a half wavelength. Since the element size also exceeds a half wavelength, the array area is not reduced. It is thinned only in terms of number of elements, not in terms of receiver area. Consequently, there is no reduction in signal-to-noise ratio, nor a requirement for increased transmitter power.

A monostatic array would transmit from the full aperture, scanning the transmitted beam over the region being examined. The "bistatic" array of this invention transmits from a sub-aperture to insonate multiple receive beam positions simultaneously. Since there is an FDA limit to spatial peak, temporal average, intensity ($I_{spta}$), there may be a danger of exceeding this limit at the transducer surface, creating a danger of burning the skin. This potential danger is eliminated by using a different transmit sub-aperture for each coherent dwell or burst of pulses. This transmitter diversity technique spreads the temporal average intensity over the face of the array, reducing $I_{spta}$ to what it would be if the entire array were used at once.

Figure 9:
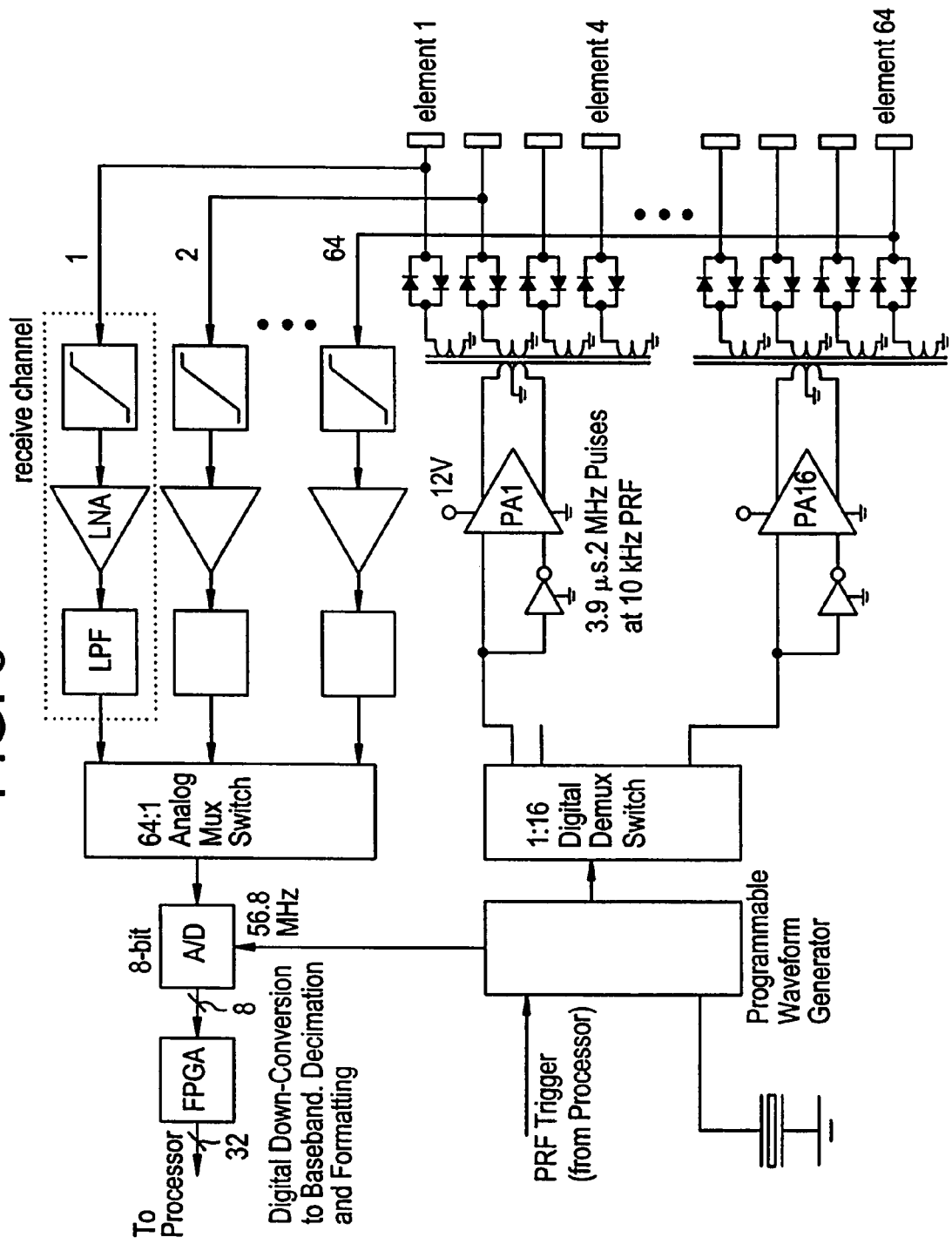
FIG. 9 is a block diagram of one possible embodiment of the Transmit-Receive Electronics for a Bistatic Ultrasound Imaging Sensor and Blood Monitoring Monitor.

For the particular implementation pictured in FIG. 9, an A/D converter is multiplexed amongst the 64 elements. The signal spectrum at any of these elements is centered at $f_0=2$ MHz, as shown in FIG. 10a. This is a real signal with a spectrum that is symmetric about f=0. This analog signal is bandpass filtered (BPF) to insure that there is little power outside of a 444 kHz band centered at 2 MHz. If a 512/9=56.889 MHz A/D converter is used, each receive channel is sampled at $f_s=888.9$ kHz, giving rise to a real sampled signal with a spectrum as shown in FIG. 10b. A processing element such as a field programmable gate array (FPGA) is used to shift the frequency by $f_s/4$ (FIG. 10c) by "multiplying" by quarter cycle samples of sinusoids (which are zeros and ones). The same FPGA also digitally filters (or Hilbert transforms) the complex signal to decimate its sampling rate by a factor of two. The spectrum of the decimated digital low-pass signal is shown in FIG. 10d.

The signal sent to the processor from each element has the spectrum shown in FIG. 9d, and consists of $r=f_s/2$ complex samples per second. The total data rate into the processor is approximately 57 megabytes per second. For non-real-time operation, tens of seconds of data at a time will be collected in system memory and then transferred to hard disk. For real-time monopulse tracking, only three beams are formed, so that the data rate is reduced to $3\times 0.8889=2.67$ Mbytes, or 5.33 Mbytes allowing for bit growth.

The transmitted pulses are sent to a group of four elements. The particular embodiment shown in FIG. 9 uses diodes to block the received signals and prevent mutual coupling between the four receive elements. After a coherent pulse train (or pulse burst used for Doppler processing), the waveform is switched to another set of 4 elements for the next burst. A separate power amplifier is associated with each of the 16 sets of elements so that the switching can be accomplished at low power.

One embodiment of sub-resolution tracking (i.e., tracking and locating blood flow to a small fraction of a spatial resolution cell) is "Monopulse". Monopulse tracking is performed as follows. A particular set of complex weights are applied to the set of received signals (64 in the example of FIG. 2) to steer a beam at the middle cerebral artery, for example. The phase taper across the array defines the steering direction and the amplitude taper (called a window in radar and a shading in sonar) is used to provide low sidelobes for high dynamic range. The beam output (a linear combination of the signals) is range gated (time delay corresponding to the desired depth) and the range-gated/beam-formed output from a sequence of transmitted pulses is then Fourier transformed to obtain a plot of amplitude versus Doppler frequency. The receive beam is steered digitally to the point that produces the maximum amplitude at high Doppler frequencies.

Since the measured data at each element is stored, the digital processor can apply more than one set of weights at a time, forming more than one beam. For software monopulse the processor will form three beams, all in the same direction. All three beams may have the same phases applied to the element signals; but the amplitudes will differ. The beam called Sum has all positive amplitudes, with the larger weights applied to the central elements. This forms a fairly broad beam. The beam called Az for "azimuth difference beam" has large positive weights on the rightmost elements and large negative weights on the leftmost elements (or vice versa). The beam called El for elevation difference has large positive weights on the top-most elements and large negative weights on the bottom-most elements. A correctly pointed beam would have Az=El=0, and Sum would be maximized.

The ratio of the peak Doppler amplitude outputs: Az/Sum, is a precise measure of the azimuth pointing error and the corresponding ratio El/Sum measures the elevation pointing error. The digital steering phase taper is thus corrected with data from a single burst of pulses. The duration of the pulse burst is the reciprocal of the medically required Doppler resolution (usually corresponding to the minimum blood velocity that can support life). Without techniques such as those described in this specification, a sequence of at least four additional Doppler dwells or pulse bursts would be required (above, below, to the right, and to the left) in a hunt and seek method to find the correct (maximum peak Doppler Amplitude) beam. With monopulse, the correction is very precise (to within ±0.1 mm of the point of maximum peak Doppler amplitude) and virtually instantaneous. For the bistatic digitally beamformed sensor, the original data exists in computer memory. Hence, whenever the Doppler processed monopulse differences are non zero, the same data set could even be re-processed to form a correctly pointed beam. A slower processor would merely process the next burst correctly.

A "front view" perspective display or a C scan display (azimuth horizontal and elevation vertical) of the blood flow map at the desired range will allow someone to aim the transducer probe or pad at the desired point (highest amplitude for high Doppler), so that the desired point is initially within the center beam. The receiver array is then steered electronically so that the monopulse differences are zero and hence the central beam is precisely aimed at the desired point. Slight motions are corrected using monopulse and large motions are corrected by again forming all beams to re-acquire the peak signal. All corrections are made entirely electronically, in the data processing or digital beamforming. A narrow receiver beam will always be precisely pointed (to within a tenth or $20^{th}$ of the receiver beamwidth) as long as the desired point remains within the much larger region covered by the transmitter (FIG. 4).

True vector velocity is computed from the blood vessel map and the radial velocity measured from the pulse Doppler dwell. A map, far more accurate than that attainable with the available angular resolution is attained as follows. The low-resolution map is used to locate a vessel of interest and a beam is locked on it at a fixed range, using azimuth and elevation monopulse. The coordinates of the point at which lock occurs is recorded. The range is then changed slightly, another lock (on the same vessel) is obtained, and the coordinates are recorded. In this manner, the vessel is mapped far more accurately than would be predicted from the available image resolution. All vessels within the field of view of the probe are similarly mapped. By moving the probe angle slightly, another region can be mapped in the same manner. Several such maps can be correlated over the region of pair-wise overlap and converted to a common coordinate system. In this manner a larger region is mapped and displayed than that of the current field of view. The current field of view would be highlighted, outlined, or presented as a color flow map. Points to be monitored in the current field are then selected by moving a cursor along the display (point and click). The selected points are Doppler processed and tracked using three-dimensional monopulse. While Doppler measurements provide only the radial component of velocity, the accurate blood vessel map provides the exact three-dimensional orientation of the vessel at the point being monitored. The measured radial velocity is divided by the projection of a unit vector representing the vessel at the monitored point onto the transducer line of sight. This gives the magnitude of the true vector blood velocity.

Sub-resolution mapping accuracy is attainable if (1) the range-azimuth-elevation-Doppler resolution cell being examined encompasses only a single blood vessel, and (2) "azimuth" monopulse is performed with the usually vertical e-axis tilted so that the orientation of the vessel in the spatial resolution cell being processed is parallel to the e-r plane ("azimuth" is constant).

The user will ascertain from the display, that the resolution cell being monitored contains only a single vessel, and would rotate the 3-D blood-vessel map to a C-scan aspect (elevation up and azimuth to the right). A vertical mark will appear in the display, within the resolution circle, to signify the orientation of the monopulse axis. This axis (parallel to the line separating the positively and negatively weighted array elements) can then be oriented so that the mark is aligned with the blood vessel in either of two ways. The probe can be physically twisted (rotated about the line of sight), or it can be electronically rotated via digital processing because the weights are applied digitally.

Figure 11:
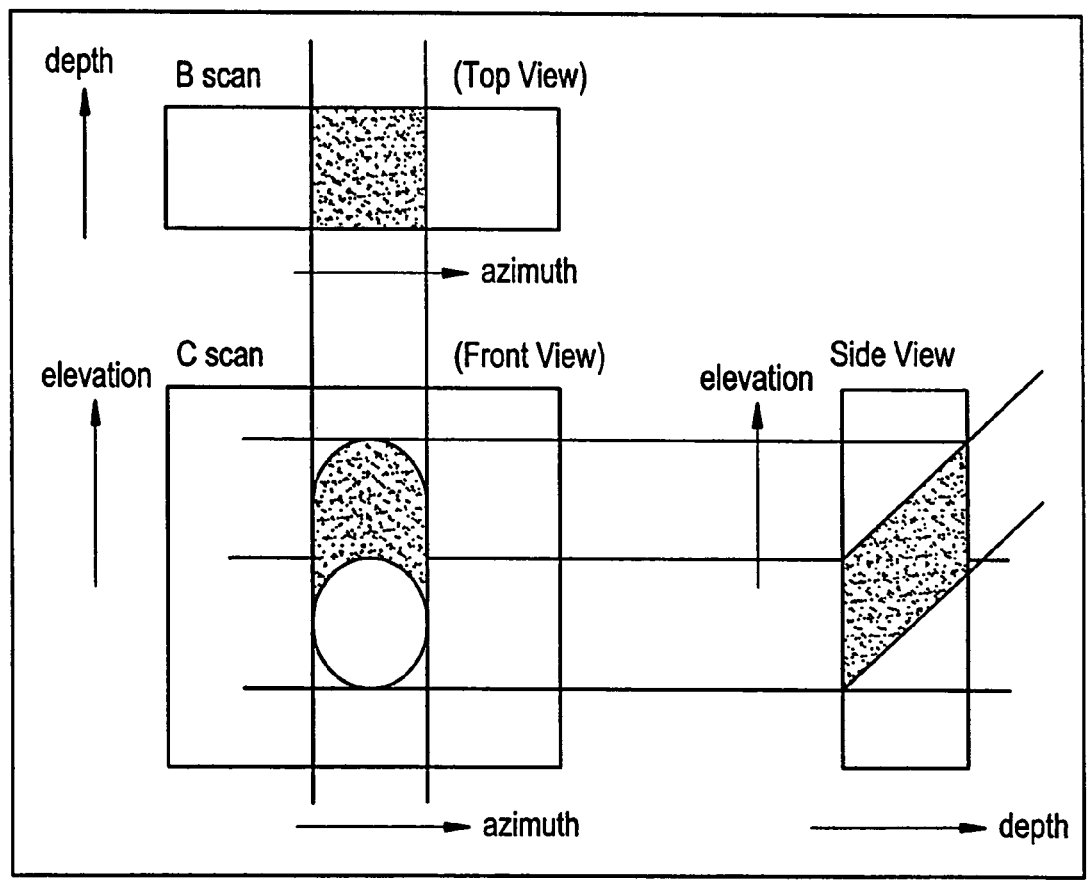
FIG. 11 shows the geometry involved in using azimuth monopulse to more accurately determine the cross-range location of a vessel. The range resolution is better than the cross-range resolution and the measured radial velocity field or color flow map has been utilized to rotate and orient the azimuth and elevation axes so that the center of the vessel is vertical, at approximately zero azimuth. The black circular cylinder represents the location of all points within the spatial resolution cell that have a particular velocity.

FIG. 11 illustrates the segment of a vessel in a single resolution cell, after rotation. The resolution cell shown is not a cube because the range resolution will typically be finer than the cross-range resolution. The illustrated circular cylinder represents blood cells in a vessel reflecting energy at a fixed Doppler frequency. These represent a cylindrical annulus of blood cells, at a constant distance from the vessel wall, moving with approximately the same velocity. In the single resolution cell of FIG. 11, the return at the highest Doppler would represent a line in three-dimensional space (the axis of the vessel) and hence a point on the azimuth axis after rotation. When applied to the highest Doppler output, the Sum beam would have broad peak at zero azimuth (a=0) and the monopulse ratio, r=Az/Sum, will be a linear function of the azimuth angle to which the array is phase steered:

$$r(a)=ka.$$

This result can be attained by applying the same phase across the aperture for the Az and Sum beams, but using the derivative of the Sum beam amplitude weights with respect to x and y respectively for the Az and El aperture weights.

Other Embodiments

If the wide transmit beam (for search and acquisition) is created by using a quadratic phase curvature instead the scheme of FIG. 2b, transmitter diversity may not be needed. Furthermore the manner of controlling grating lobes in FIG. 1 and FIGS. 5-8 is only one of many. Using a wider bandwidth and time-delay steering can also reduce grating lobes.

EXAMPLE II

Ultrasound Measurement of Blood Volume Flow

As explained above, current ultrasound Doppler devices measure radial velocity. Several methods now exist for 3-D ultrasound imaging, such as those involving transducer motion. A three-dimensional image with Doppler allows for the measurement of vector velocity. Example I above provides measurement and long term monitoring of three-dimensional vector velocity. If the resolution of a color flow Doppler image is sufficient to provide an estimate of the inside diameter of the blood vessel, then measurement of volume blood flow becomes practical. Presently available ultrasound imaging devices have either low resolution or they only produce a two-dimensional image. The present invention combines vector velocity information (such as attained as explained in Example I above) with additional information to obtain volume flow. The additional information is the inside diameter of the vessel under examination, the blood velocity profile across the vessel, or the vector velocity as a function of time and position (i.e., the velocity field). This additional information can be obtained from a high-resolution radial-Doppler or color flow image or from external data such as a high-resolution MRI image.

A two-dimensional array of piezoelectric elements, or some other means, is used to image blood flow in a three dimensional region. A particular point on a particular vessel is selected and the vector representing the orientation of the vessel is noted. The radial velocity divided by the cosine of the angle made by the vessel with the line of sight at the measurement point is the magnitude of the vector velocity. That number integrated over the vessel cross section would give the volume flow in volume per unit time or milliliters per minute, for example.

Figure 12:
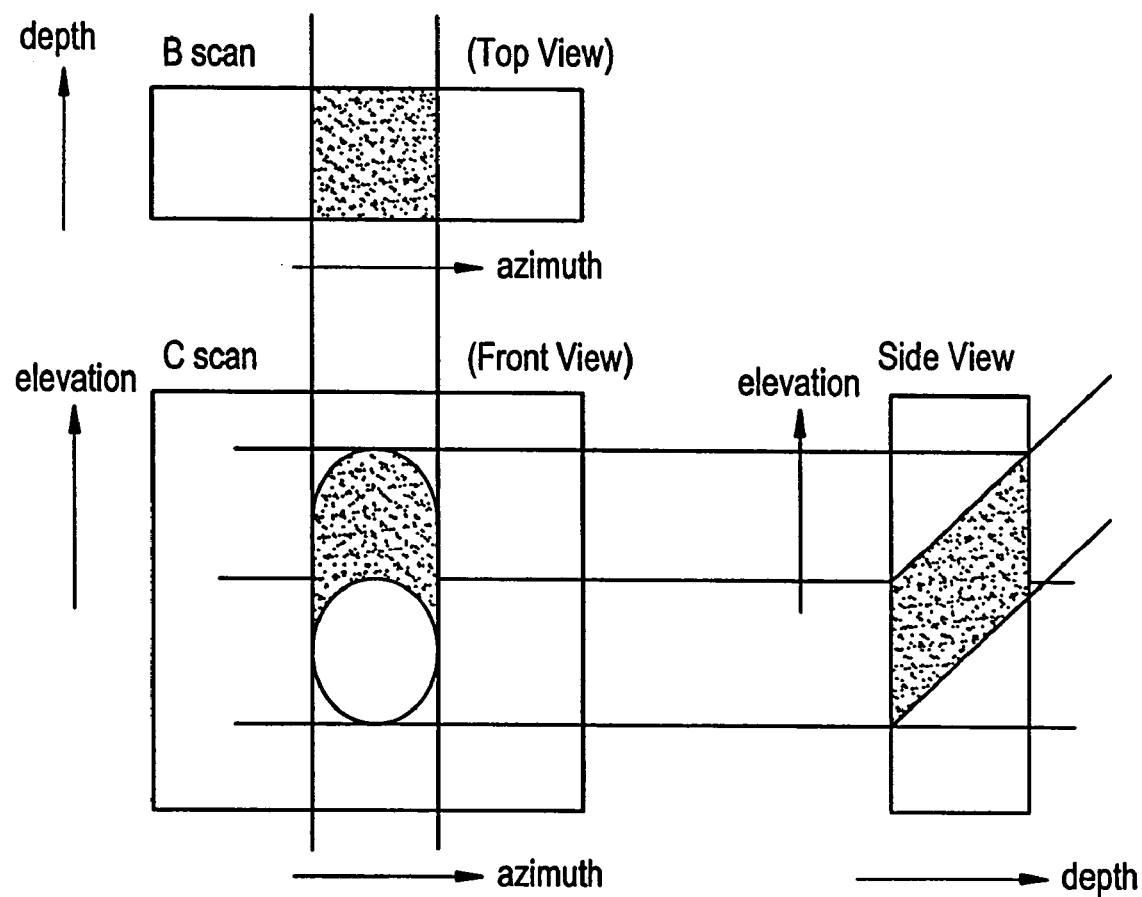
FIG. 12 shows the geometry involved in using Doppler ultrasound to determine the diameter of a vessel or the velocity field within the vessel. While the initial 3-D orientation of the vessel is general, a measured 3-D radial velocity field or 3-D color flow map has been utilized to rotate and orient the azimuth and elevation axes so that the center of the vessel is vertical, at approximately zero azimuth. In other words, the coordinate system has been rotated about the depth-axis so that the centerline of the vessel is in the depth-elevation plane. This can be accomplished either by a change of coordinates in software or by physically rotating the ultrasound probe. The black circular cylinder represents the location of all points within the illustrated box that have a particular velocity. The diameter of the cylinder is then measured as the azimuth extent of a high-resolution depth-azimuth or B-scan image at the Doppler frequency under examination.

FIG. 12 shows a circular cylinder representing blood cells in a vessel moving at a particular velocity and thus reflecting energy at a specific Doppler frequency. The figure assumes that methods such as those in the referenced invention, for example, have been used to measure the 3-D orientation of the vessel so that the vector velocity can be calculated and the azimuth axis can be defined to be perpendicular to the vessel.

The simplest way to estimate volume flow is to measure the vessel diameter, d, (or radius d/2), calculate the cross-sectional area, $A=\pi(d/2)^2$, and multiply by the average velocity. A more accurate way is to integrate the velocity as a function of position, over the cross-section. The velocity is a function of the radius, a, of the cylinder depicted in FIG. 12. If a is the distance from the cylinder to its axis, and v (a) is the velocity function, then the volume flow is $$2\pi \int_0^{d/2} a v(a) \, da \quad (7)$$

Equation (1) assumes a circular cross-section of constant radius, r=d/2. It is a special case of the more general polar coordinate integration:

$$\int_0^{2\pi} \left( \int_0^{r(\theta)} a v(a, \theta) \, da \right) d\theta \quad (8)$$

The velocity function is determined by determining the diameter (and hence the radius) of the cylinder corresponding to each velocity.

For example, a 1.5-cm diameter Doppler ultrasound transducer array operating at 10 MHz will be oriented with the length or azimuth direction perpendicular to the vessel to produce a B-scan (depth-azimuth) image. At a depth of approximately 10 mm, the cross range resolution is 0.1 mm. If the vessel diameter is 1 mm, the diameter can be measured with an accuracy of ±5%. The area of the vessel is thus known to an accuracy of 10%. Since the average vector velocity can be measured extremely accurately, the volume flow is also accurate to ±10%. The best accuracy is attained by measuring the azimuth extent corresponding to various velocities and then numerically evaluating equation (7) or (8). Naturally, a skilled artisan can readily program a processor to solve these equations, and calculate blood flow volume using routine programming techniques.

Since the autocorrelation function (pulse-to-pulse, at a fixed range) and the Doppler Power Spectrum form a Fourier pair, the total power can be obtained either as the autocorrelation function at zero lag or the integral of the Doppler Power Spectrum (Spectral Density) over all Doppler frequencies. Since radial velocity is proportional to Doppler frequency, the mean velocity can be obtained from the autocorrelation function as shown below:

$$R_{xx}(\tau) = \frac{1}{2\pi} \int_{-\infty}^{\infty} S(\omega) e^{j\omega\tau} d\omega = \int_{-\infty}^{\infty} S_d(f) e^{j2\pi f \tau} df, \text{ hence}$$

$$R_{xx}(0) = \int_{-\infty}^{\infty} S_d(f) df = P_d = \text{total Doppler power and}$$

$$\dot{R}_{xx}(\tau) = \dot{R}_{xx}(\tau) = \int_{-\infty}^{\infty} [j 2\pi f S_d(f)] e^{j 2\pi f \tau} df, \text{ leading to}$$

$$\dot{R}_{xx}(0) = j \int_{-\infty}^{\infty} 2\pi f S_d(f) df. \text{ Thus}$$

$$-j \frac{\dot{R}_{xx}(0)}{R_{xx}(0)} = 2\pi \int_{-\infty}^{\infty} f \frac{S_d(f)}{\int_{-\infty}^{\infty} S_d(f) df} df = 2\pi E\{f_d\},$$

where the Doppler frequency and its mean (expected value) are related to the radial blood velocity and its mean by $$f_d = \frac{2 f_0}{c} v. \text{ Hence}$$

$$E\{v\} = \int_{-\infty}^{\infty} v \frac{P(v)}{\int_{-\infty}^{\infty} P(v) dv} dv = -j \frac{c}{4\pi f_0} \frac{\dot{R}_{xx}(0)}{R_{xx}(0)}$$

which is used in the autocorrelation method of color-flow blood-velocity imaging. We note that if we do not normalize by dividing by the total Doppler power, we obtain a power-velocity product that indicates the volume flow rate. This is due to the fact that power is directly proportional to area [see Reference 1].

Since all velocity vectors are parallel at the narrowest point (the vena contracta), flow at that particular point can be considered as non-turbulent, even though severe turbulence exists before and after. Reference 1 shows that regurgitant blood flow through the mitral heart valve can be quantitatively measured by observing the Doppler spectrum at that point and using the power-velocity-integral relation below.

In terms of the velocity power spectrum, $P(v)=(2f_0/c) S_d(f)$, Reference 1 shows that the blood vessel area in a "slice"

perpendicular to the line of sight is directly proportional to the total Doppler power (the total power at the output of the high-pass wall filter).

$$A = \frac{A_0}{P_0} P_d = \frac{A_0}{P_0} \int P(v) dv$$

where $A_0$ and $P_0$ are the known area and measured power in a narrow beam, smaller than the vessel. If the blood flow makes an angle $\theta$ with the line of sight, the area, and hence power, is increased by the factor $1/\cos\theta$. This offsets the fact that only the radial component of velocity is measured, so that the power velocity integral provides true volume flow:

$$\dot{Q} = \frac{dQ}{dt} = \frac{A_0}{P_0} \int v P(v) dv$$

In Reference 1, P was measured with the same probe as $P_0$ by masking the outside of the aperture in order to create a wider beam. With our 2-D phased array, we would merely turn off or ignore some of the outer elements. More importantly, we can use the 3-D image to precisely locate the vena contracta, and lock on to it using monopulse. We can even monitor the valve during a stress test, while the patient is on a treadmill.

We note here, that there are several ways to measure the volume flow rate. Reference 1 uses the fact that it is proportional to the integral of the product of the velocity and the power per unit velocity, as in the last equation. An other way is to recognize that it is equal to the product of the average radial velocity and the total projected area that is, in turn, proportional to total Doppler power. Since the total Doppler power is used in the denominator of the autocorrelation-based color-flow velocity map, volume flow rate can be obtained by merely not dividing by the total power. If the $i^{th}$ pulse return (after MTI or Doppler high-pass or wall filtering) is $$z_i = x_i + j y_i, i=1, 2, \ldots, N$$

the volume flow rate is proportional to $$\sum_{i=2}^{N} x_i y_{i-1} - y_i x_{i-1}$$

The normalization (denominator) that is used to convert this last quantity to mean velocity can be $$\sum_{i=2}^{N} x_i x_{i-1} + y_i y_{i-1}$$

that is based on a derivation in Reference 2, or a simple power estimate, such as $$\sum_i x_i^2 + y_i^2$$

The point we wish to make here is that by not dividing by a power estimate to obtain radial velocity, we obtain volume flow. Current ultrasound Doppler imaging systems compute the mean velocity as a ratio, $$E(v) = F/P_d,$$

and display it as a color flow image. Newer imaging systems [2] also display total Doppler power (at the output of the wall filter), $P_d$. By not dividing the color flow image by $P_d$, we can also display the true volume flow, dQ/dt. This is because the numerator, $$F = P_d \cdot E(v),$$

is the power-velocity-integral that is directly proportional to the volume flow.

Determination of the scale factor, $A_0/P_0 = A/P_d = dQ/dt/F$, that must multiply F to obtain volume flow requires further comment.

$A_0$ is the area of a reference beam. In [1], $A_0$ is smaller than the blood flow area. We will describe three normalization approaches.

1. Use a single transmit beam, wider than the vessel, and two simultaneous receive beams. One receive beam (the measurement beam) is the same as the transmit beam and the other (the reference beam) is smaller than the vessel.
2. Use two (sequential or multiplexed) two-way (transmit and receive) beams. One (the measurement beam) is wider than the vessel and the other (the reference beam is smaller than the vessel.
3. Use two (sequential or multiplexed) two-way (transmit and receive) beams. Both are wider than the vessel and the measurement beam is wider than the reference beam.

Let $A_0$ be the known area of the reference beam, let $P_0$ and $P_1$ be the measured received power in the reference and measurement beams. In case 1, the transmit power density is the same for measurement and reference. The receive power is proportional to area. If the area of the vessel (in a slice perpendicular to the line of sight) is A, it follows that $$A/A_0 = P_1/P_0.$$

In cases 2 and 3, the transmit power density is greater in the reference beam than in the measurement beam, but by a known factor. In all three cases, the power received in the measurement beam is proportional to the vessel area. In case 2, the received reference power also varies with vessel size, but at a different rate than in the measurement beam. With proper calibration, correct measurements can be attained in all three cases.

[1]. T. Buck, Et al, "Flow Quantification in Valvular Heart Disease Based on the Integral of Backscattered Acoustic Power Using Doppler Ultrasound," *Proc. IEEE*, vol.88, no.3, pp.307-330, March 2000.

[2]. K. Ferrara and G DeAngelis, "Color Flow Mapping", *Ultrasound in Medicine and Biology*, vol.23, no.2, pp.321-345, March 1997.

EXAMPLE III

3-D Doppler Ultrasound Blood Flow Monitor with Enhanced Field and Sensitivity

This example sets forth an ultrasound Doppler device and method that enables non-invasive diagnosis (the conventional role of ultrasound systems), and also non-invasive unattended and continuous monitoring of vascular blood flow for medical applications. In particular, the embodiment of the present invention set forth in this example provides: (1) affordable three-dimensional imaging of blood flow using a low-profile easily-attached transducer pad, (2) real-time vector velocity, and (3) long-term unattended Doppler-ultrasound monitoring in spite of motion of the patient or pad. None of these three features are possible with current ultrasound equipment or technology.

The pad and associated processor collects and Doppler processes ultrasound blood velocity data in a three-dimensional region through the use of a two-dimensional phased array of piezoelectric elements on a planar, cylindrical, or spherical surface. Through use of unique beamforming and tracking techniques described herein, the present invention locks onto and tracks the points in three-dimensional space that produce the locally maximum blood velocity signals. The integrated coordinates of points acquired by the accurate tracking process is used to form a three-dimensional map of blood vessels and provide a display that can be used to select multiple points of interest for expanded data collection and for long term continuous and unattended blood flow monitoring. The three dimensional map allows for the calculation of vector velocity from measured radial Doppler.

A thinned array (greater than half-wavelength element spacing of the transducer array) is used to make a device of the present invention inexpensive and allow the pad to have a low profile (fewer connecting cables for a given spatial resolution). The array is thinned without reducing the receiver area by limiting the angular field of view. Grating lobes due to array thinning can be reduced by using wide bandwidth and time delay steering. The array, or portions of the array, is used to sequentially insonate the beam positions. Once the region of interest has been imaged and coarsely mapped, the array is focused at a particular location on a particular blood vessel for measurement and tracking. Selection of the point or points to be measured and tracked can be based on information obtained via mapping and may be user guided or fully automatic. Selection can be based, for example, on peak response within a range of Doppler frequencies at or near an approximate location.

In the tracking mode a few receiver beams are formed at a time: sum, azimuth difference, elevation difference, and perhaps, additional difference beams, at angles other than azimuth (=0 degrees) and elevation (=90 degrees). Monopulse is applied at angles other than 0 and 90 degrees (for example 0, 45, 90, and 135 degrees) in order to locate a vessel in a direction perpendicular to the vessel. When the desired (i.e. peak) blood velocity signal is not in the output, this is instantly recognized (e.g., a monopulse ratio, formed after Doppler filtering, becomes non-zero) and the array is used to track (slow movement) or re-acquire (fast movement) the desired signal. Re-acquisition is achieved by returning to step one to form and Doppler-process a plurality of beams in order to select the beam (and the time delay or "range gate") with the most high-Doppler (high blood velocity) energy. This is followed by post-Doppler monopulse tracking to lock a beam and range gate on to the exact location of the peak velocity signal. In applications such as transcranial Doppler, where angular resolution based on wavelength and aperture size is inadequate, fine mapping is achieved, for example, by post-Doppler monopulse tracking each range cell of each vessel, and recording the coordinates and monopulse-pair angle describing the location and orientation of the monopulse null. With a three-dimensional map available, true vector velocity can be computed. For accurate vector flow measurement, the monopulse difference is computed in a direction orthogonal to the vessel by digitally rotating until a line in the azimuth-elevation or C-scan display is parallel to the vessel being monitored. The aperture is more easily rotated in software (as opposed to physically rotating the transducer array) if the aperture is approximately circular (or eliptical) rather than square (or rectangular). Also, lower sidelobes result by removing elements from the four corners of a square or rectangular array in order to make the array an octagon.

All currently available ultrasound devices (including "Doppler color flow mapping" systems) form images that are limited by their resolution. In some applications, such as TCD, the low frequency required for penetration of the skull makes the azimuth and elevation resolution at the depths of interest larger than the vessel diameter. In this invention, as long as (1) a blood vessel or (2) a flow region of a given velocity can be resolved by finding a 3-D resolution cell through which only a single vessel passes, that vessel or flow component can then be very accurately located within the cell. Monopulse is merely an example of one way to attain such sub-resolution accuracy (SRA). Other methods involve "super-resolution" or "parametric" techniques used in "modem spectral estimation", including the MUSIC algorithm and autoregressive modeling, for example. SRA allows an extremely accurate map of 3-D flow.

This invention utilizes post-Doppler, sub-resolution tracking and mapping; it does Doppler processing first and uses only high Doppler-frequency data. This results in extended targets since the active vessels approximate "lines" as opposed to "points". In three-dimensional space, these vessels are resolved, one from another. At a particular range, the monopulse angle axis can be rotated (in the azimuth-elevation plane) so that the "line" becomes a "point" in the monopulse angle direction. That point can then be located by using super-resolution techniques or by using a simple technique such as monopulse. By making many such measurements an accurate 3-D map of the blood vessels results.

Methods for extending the angular field of view of the thinned array (that is limited by grating lobes) include (1) using multiple panels of transducers with multiplexed processing channels, (2) convex V-shaped transducer panels, (3) cylindrical shaped transducer panel, (4) spherical shaped transducer panel, or (5) negative ultrasound lens. If needed, moving the probe and correlating the sub-images can create a map of an even larger region.

Active digital beamforming can be utilized, but the implementation depends on a choice to be made between wideband and narrowband implementations. If emphasis is on high resolution mapping of the blood vessels, then a wide bandwidth (e.g., 50% of the nominal frequency) is used for fine range resolution. If emphasis is on Doppler spectral analysis, measurement, and monitoring, the map is only a tool. In this case, a narrowband, low cost, low range-resolution, high sensitivity implementation might be preferred. A wideband implementation would benefit in performance (higher resolution, wider field of view, and reduced grating lobes) using time-delay steering while a narrowband implementation would benefit in cost using phase-shift steering. The invention can thus be described in terms of two preferred implementations.

In a wideband implementation, time delay steering can be implemented digitally for both transmit and receive by oversampling and digitally delaying in discrete sample intervals. In a narrowband implementation, (1) phase steering can be implemented digitally (digital beamforming) for both transmit and receive, and (2) bandpass sampling (sampling at a rate lower than the signal frequency) can be employed with digital down-conversion and filtering.

Overview of this Embodiment.

This embodiment of the present invention involves (1) a family of ultrasound sensors, (2) the interplay of a set of core technologies that are unique by themselves, and (3) a number of design options which represent different ways to implement the invention. To facilitate an organizational understanding of this many-faceted invention, a discussion of each of the three topics above follows.

The sensors addressed are all two-dimensional (i.e., planar or on the surface of a convex shape such as a section of a cylinder) arrays of piezoelectric crystals for use in active, non-invasive, instantaneous (or real-time), three-dimensional imaging and monitoring of blood flow. While the sensors and the techniques for their use apply to all blood vessels in the body, the figures and detailed description emphasizes the transcranial Doppler (TCD) monitor method as a nonlimiting example. The method of the present invention utilizes a new, useful and unobvious approach to 3-D imaging of blood velocity and blood flow that (1) allows for finer image resolution than would otherwise be possible with the same hardware complexity (number of input cables and associated electronics) and (2) allows for finer accuracy than would ordinarily be possible based on the resolution. The invention measures and monitors 3-D vector velocity rather than merely the radial component of velocity.

The core technologies that constitute the invention are (1) array thinning with large elements and limited scanning, (2) array shapes to reduce peak sidelobes and extend the field of coverage, (3) post-Doppler sub-resolution tracking, (4) post-Doppler sub-resolution mapping, (5) additional methods for maximizing the angular field of view, and (6) various digital beamforming procedures for implementing the mapping, tracking, and measurement processes. The invention encompasses array thinning, where the separation between array elements is significantly larger than half the wavelength. This reduces the number of input cables and input signals to be processed while maintaining high resolution and sensitivity and avoiding ambiguities. In the TCD application, where signal to noise and hence receiver array area is of paramount importance, array thinning is possible without reducing the receiver array area because a relatively small (compared to other applications) angular field of view is needed.

Thinning with full aperture area imposes limitations on the angular field of view. Methods for expanding the field of view include using more elements than are active at any one time. For example, if the electronics is switched between two identical panels, the cross-range field of view at any depth is increased by the size of the panel. If the panels are pointed in slightly different directions so that overlapping or redundant beams are avoided, the field of view is doubled. A generalization of this approach involves the use of an array on a cylindrical or spherical surface.

In the TCD application, the achievable angular resolution is poor, regardless of the method of thinning, or whether or not thinning is used. Once a section of a blood vessel is resolved from other vessels in Doppler, depth, and two angles (az and el), Post-Doppler sub-resolution processing locates that section to an accuracy that is one-tenth to one-twentieth of the resolution. This allows for precise tracking and accurate mapping. Tracking provides for the possibility of unattended long term monitoring and mapping aids the operator in selecting the point or points to be monitored.

One of ordinary skill in the art will readily recognize that there are many options available in the design of any member of the family of sensors that utilizes any or all of the core technologies that comprise this invention, all of which are encompassed by the present invention. A two-dimensional array is established art that can be designed in many ways and can have many sizes and shapes (rectangular, round, etc.).

As with other nonlimiting embodiments of the present invention set forth above, this embodiment is a non-invasive, continuous, unattended, volumetric, blood vessel tracking, ultrasound monitoring and diagnostic device for blood flow. It will enable unattended and continuous blood velocity measurement and monitoring as well as 3-dimensional vascular tracking and mapping using an easily attached, electronically steered, transducer probe that can be in the form of a small pad for monitoring application, when desired. Although a device of the present invention has applications with blood vessels in any part of the body, the cranial application will be used as a specific example. A device of the present invention can, for example:

1. Measure and continuously monitor blood velocity with a small low-profile probe that can be adhered, lightly taped, strapped, banded, or otherwise easily attached to the portion of the body where the vascular diagnosis or monitoring is required.
2. Track and maintain focus on multiple desired blood vessels in spite of movement.
3. Map 3-D blood flow; e.g., in the Circle of Willis (the central network of arteries that feeds the brain) or other critical vessels in the cranial volume.
4. Perform color velocity imaging and display a 3-D image of blood flow that is rotated via track ball or joystick until a desired view is selected.
5. Form and display a choice of projection, slice, or perspective views, including (1) a projection on a depth-azimuth plane, a B-scan, or a downward-looking perspective, (2) a projection on an azimuth-elevation plane, a C-scan, or a forward-looking perspective, or (3) a projection on an arbitrary plane, an arbitrary slice, or an arbitrary perspective.
6. Use a track ball and buttons to position circle markers on the points were measurement or monitoring of vector velocity is desired.
7. Move the track location along the blood vessel by using the track ball to slide the circle marker along the image of the vessel.
8. Display actual instantaneous and/or average vector velocity, estimated average volume flow, and/or Doppler spectral distribution.
9. Maintain a multi-day history and display average blood velocity versus time for each monitored vessel over many hours.
10. Sound an alarm when maximum or minimum velocity is exceeded or when emboli count is high; and maintain a log of emboli detected.
11. Track, map, and monitor small vessels (e.g., 1 mm in diameter), resolve vessels as close as 4 mm apart (for example), and locate them with an accuracy of ±0.1 mm, for example.

This embodiment of the present invention will allow a person with little training to apply the sensor and position it based on an easily understood ultrasound image display. The unique sensor can continuously monitor artery blood velocity and volume flow for early detection of critical events. It will have an extremely low profile for easy attachment, and can track selected vessels; e.g., the middle cerebral artery (MCA), with no moving parts. If the sensor is pointed to the general volume location of the desired blood vessel (e.g., within ±1 cm.), it will lock to within ±0.1 mm of the point of maximum radial component of blood flow and remain locked in spite of patient movement.

A device of the present invention can remain focused on the selected blood vessels regardless of patient movement because it produces and digitally analyzes, in real time, a 5-dimensional data base composed of signal-return amplitude as a function of:
1. Depth,
2. Azimuth,
3. Elevation,
4. Radial component of blood velocity,
5. Time.

Since a device of the present invention can automatically locate and lock onto the point in three dimensions having the maximum high-Doppler energy, i.e., maximum volume of blood having a significant radial velocity, unattended continuous blood velocity monitoring is one of its uses. By using the precise relative location of the point at which lock occurs as a function of depth, a device of the present invention can map the network of blood vessels as a 3-dimensional track without the hardware and computational complexity required to form a conventional ultrasound image. Using the radial component of velocity along with the three-dimensional blood path, a device of the present invention can directly compute parameters of blood flow, such as vector velocity, blood flow volume, and Doppler spectral distribution.

A device having applications in a method of the present invention is a non-mechanical Doppler ultrasound-imaging sensor comprising probes, processing electronics, and display. Specific choices of probes allow the system to be used for transcranial Doppler (TCD), cardiac, dialysis, and other applications.

Figure 13:
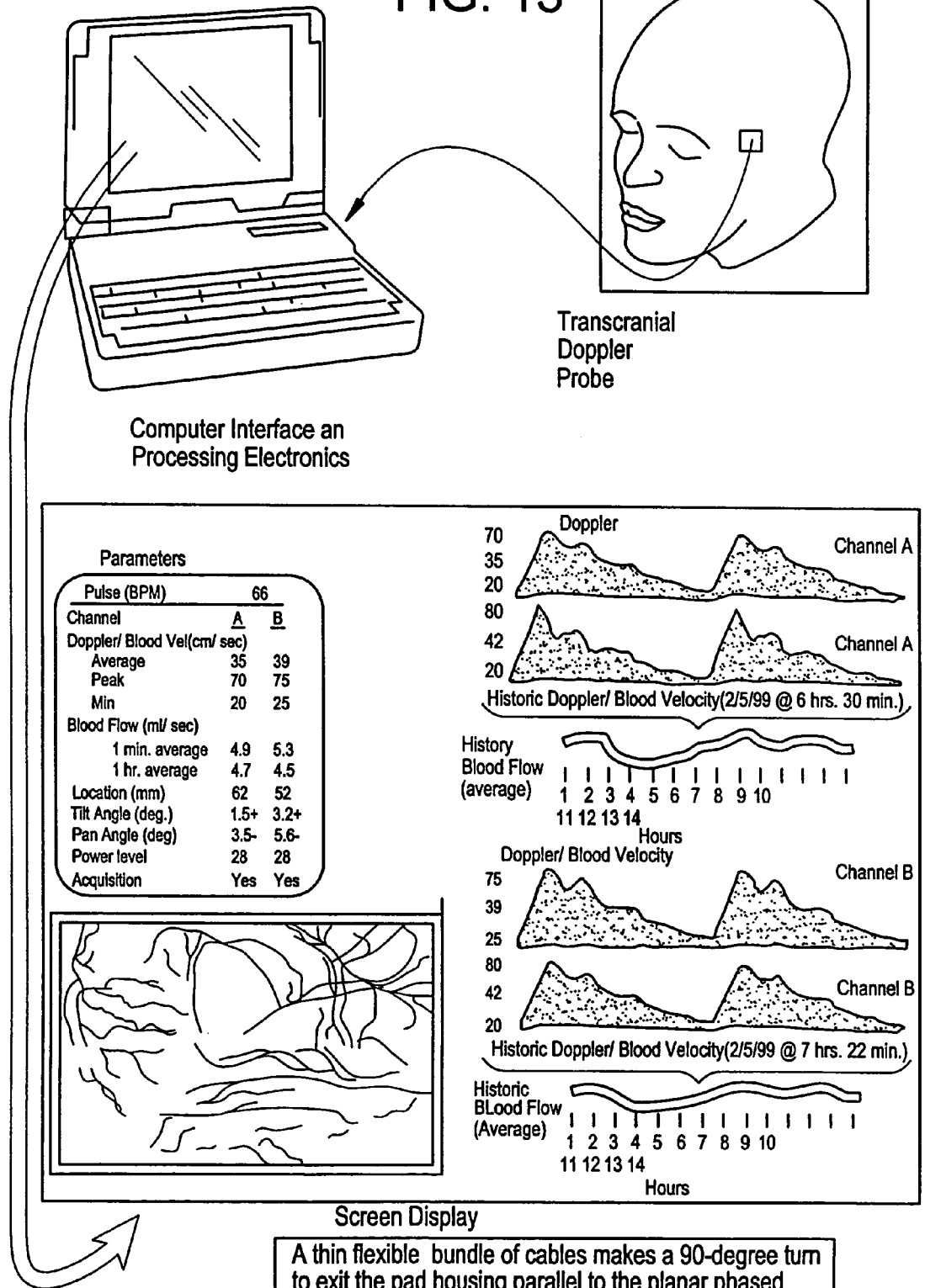
FIG. 13 illustrates the Blood Flow Mapping Monitor in use with a Transcranial Doppler Probe, as an example.

Just as with other embodiments of the present invention set forth above, this embodiment has application for medical evaluation and monitoring multiple locations in the body. However, the transcranial Doppler application will be used as an nonlimiting example. FIG. 13 shows the overall TCD configuration and a typical definition of the display screen. The TCD system is comprised of one or two probes that may be attached to the head with a "telephone operator's band" or a Velcro strap. The interface and processing electronics is contained within a small sized computer. A thin cable containing from 52 to 120 micro coax cables, depending on the example probe design used, attaches the probe to the electronics in the computer. When the operator positions the probe on the head and activates the system, the Anterior, Middle and Posterior Cerebral Arteries and the Circle of Willis are mapped on the screen along with other blood vessels. The arteries or vessels of interest are selected by manually locating a cursor overlaid on the vessel 3-D map. The system locks onto the blood vessels and tracks their position electronically. A variety of selected parameters are displayed on the screen; e.g., the velocity, the pulse rate, depth of region imaged, gain and power level. Using only one probe the TCD can monitor multiple arteries (vessels) at a time. By way of example, presented on the screen are dual traces, one for each artery selected. The blood velocity can be dynamically monitored. As shown in FIG. 13 both the current blood velocity (dark traces) and any historic trace (lighter color) can be displayed simultaneously. The average blood velocity or estimated average flow for each artery is displayed below the respective velocity trace. The image shows the arteries and the channel used for each artery. When two probes are used, the display is split showing signals from both of them. For example, using a different probe (i.e., different size) with the same electronics and display, the unit can be used to measure and monitor the blood flow in a carotid artery. Similarly, it can be used to perform this function for dialysis, anesthesia, and in other procedures.

Figure 14:
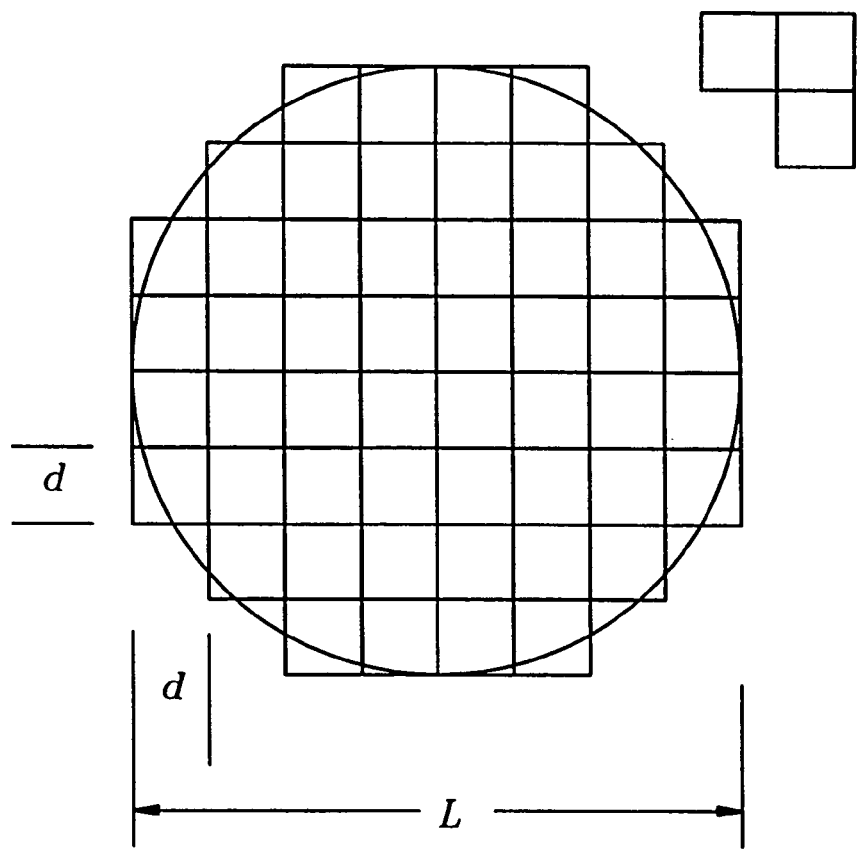
FIG. 14 shows a 52-element ultrasound transducer array example, based on an 8 by 8 rectangular array of elements with 3 elements removed from each corner to make the array octagonal instead of rectangular or square. For this example, the elements are square ($d_1=d_2=d$) and $L/d=8$.
Figure 15:
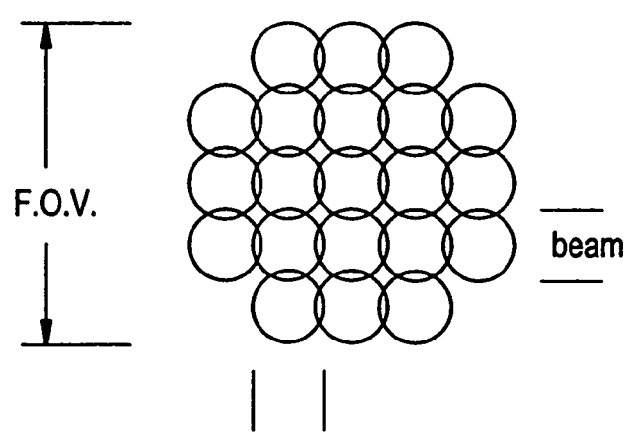
FIG. 15 shows a typical pattern of electronically scanned beams produced by the array in FIG. 14. The beam width is nominally, given by the signal wavelength divided by the size, L, of the array. The angular field of view (F.O.V.) is limited by the maximum angle to which the array can be steered without producing grating lobes that are not sufficiently attenuated by the pattern of the individual dxd element.
Figure 21:
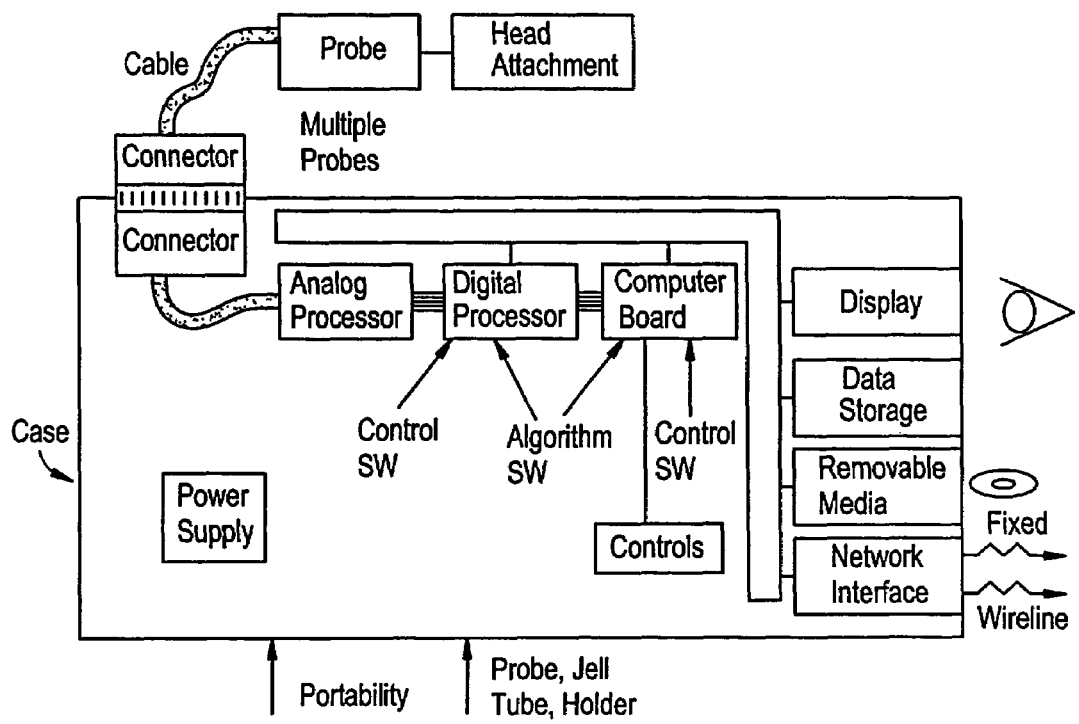
FIG. 21 is an example overall block diagram of a blood flow mapping monitor embodiment.

The sensor is a two dimensional array of transducer elements (e.g., piezoelectric crystals) that are electronically activated in both transmit and receive to effect a scan. For example, if a square (N×N) array is used, up to $N^2$ elements could be used at the same time. This is illustrated in FIG. 14 for the case of N=8. The array need not be square. Any M×N array may be utilized in this manner. All received signals (52 in the example of FIG. 13) are sampled, digitized, and processed. This can be done, for example, in a desk top or lap top personal computer with additional cards for electronics and real-time signal processing as illustrated in FIG. 13 and FIG. 21. The array is phase steered or time-delay steered, depending on the bandwidth utilized, which depends in turn on the desired range resolution. The angular field of view shown in FIG. 15 is limited by the existence of grating lobes caused by array thinning (spacing the array elements more than ½ wavelength apart). The concept is illustrated below for a 1-dimensional array forming a beam that measures only one angle. For a two-dimensional array, this represents a horizontal or vertical cut through the cluster of beams shown in FIG. 15.

The frequency utilized for TCD is usually at or near 2 MHz because higher frequencies do not propagate well through bone and lower frequencies do not provide adequate reflection from the blood cells. However, other frequencies have applications when examining other parts of the body. With a propagation velocity of 1.54 millimeters per microsecond, the wavelength is 0.77 mm. If a filled array is utilized, the element size and array pitch would be d=0.7712. For a cross-range resolution of 5.8 mm or less at a depth of 60 mm, the array size, L, must be at least 8 mm (Resolution=depth× wavelength/L). Since N=L/d in FIG. 2, N must exceed 21 and hence the array must have on the order of $N^2$ or over 400 elements. If the desired resolution is halved, the array size doubles and the number of elements exceeds 1,600. The array in FIG. 14 is said to be "thinned" because it only has 52 elements.

As explained above, "grating lobes" are ambiguities or extra, unwanted, beams caused by using a transducer array whose elements are too large and hence too far apart. The following analysis illustrates grating lobe suppression for the worst case of narrowband signals and phase-shift beam processing. Time delay processing using wideband signals would be similar, but would further attenuate or eliminate grating lobes, resulting in even better performance. Naturally, one of ordinary skill in the art can readily program a processor to suppress or limit grating lobes with the equations described herein using routine programming techniques.

Let $$x=(d/\lambda) \sin \theta, \tag{9}$$

represent a normalization for the angle, θ, from which reflected acoustic energy arrives. The azimuth (or elevation) angle, θ, is zero in the broadside direction, perpendicular to the transducer array and d is the width (or length) of a single element of the receiver array. The wavelength of the radiated acoustic wave is λ=c/f, where c is the acoustic propagation velocity (1540 meters/second in soft tissue) and f is the acoustic frequency (usually between 1 and 10 megahertz). The wide pattern in FIG. 16a is the element pattern $$a_e(x)=\sin \pi x/\pi x. \tag{10}$$

The pattern is the product of the element pattern, the array pattern, and cos θ.

$$a(\theta)=\cos (\theta) a_e(x) a_a(x) \tag{11}$$

Figures 16, 16A, 16B:
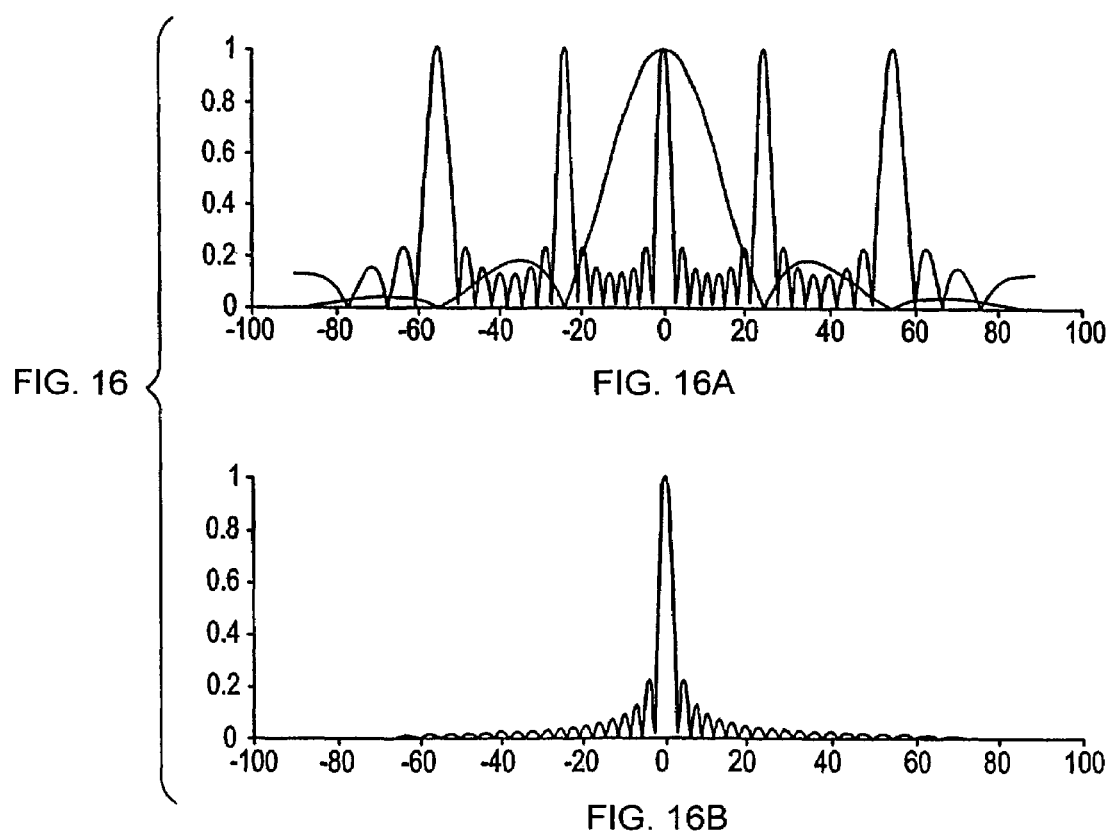
FIG. 16 shows one-dimensional patterns for an eight-element monostatic linear transducer array corresponding to a column or a row in FIG. 16.
FIG. 16a (top) shows the Element Pattern and Array Pattern with the beam steered to broadside (x=0). The Array Pattern has Grating Lobes (Receiver Ambiguities).
FIG. 16b shows the resultant beam pattern. The Grating Lobes are suppressed.

Each of the two component patterns is plotted separately as a function of θ in FIG. 16a and the total pattern of equation

(11) is plotted in FIG. 16b. In the far-field, i.e., for $\lambda r \gg L^2$, where r is the range or depth and L is the length of the aperture, the array pattern steered to the angle $\theta=\theta_0$ is $$a_a(x) = \sum_{n=0}^{N-1} w_n e^{j2\pi n(x-x_0)}, \quad (12)$$

where $w_n$ is a weighting to reduce sidelobes and N is the number of elements in one dimension. As seen in FIG. 16a, equation (12) is periodic in x. The peak at $\theta=\theta_0$ ($\theta_0=0$ in FIG. 16) is the desired beam and the others are grating lobes.

In the near field, when focused at $(r_0,\theta_0)$, equation (12) is replaced by the slightly better general Fresnel approximation:

$$a_a(x,z) = \sum_{n=0}^{N-1} w_n e^{j2\pi\left[n(x-x_0)+\left(n-\frac{N-1}{2}\right)^2(z-z_0)\right]} \quad (13)$$

(provided that the range significantly exceeds the array size, r>L), where x=d sin $\theta/\lambda$, as before, and $$z = d^2 \cos^2\theta/\lambda r. \quad (14)$$

Because the receiver aperture is sampled with a spatial period of d, the receiver array pattern will be periodic in sin θ, with a period of θ/d (equation 12). This periodicity means that the array pattern is ambiguous. When the array is pointed broadside (θ=0), it will also be pointed at the angle θ=sin$^{-1}$ (λ/d), for example. In terms of the normalized variable, x, the period is unity. Since |sin θ| cannot exceed 1, the variable x is confined to the interval [−d/λ, d/λ]. The conventional element spacing is d=λ/2. Thus, in a conventional phased array, x is always between −0.5 and +0.5, and hence ambiguities are not encountered. In a highly thinned array (d>λ), there will normally be ambiguities or grating lobes as illustrated in FIG. 16a. The second grating lobe, at x=2 or θ=sin$^{-1}$ (2λ/d), is not real when d does not exceed 2λ.

FIG. 16b shows that the unsteered total pattern does not exhibit grating lobes. In a two dimensional array, the elements could be rectangular instead of square ($d_x \times d_y$), and the results would still be valid. Similar results could be obtained for an array in which the elements are staggered from row to row (and/or column to column).

Figure 17:
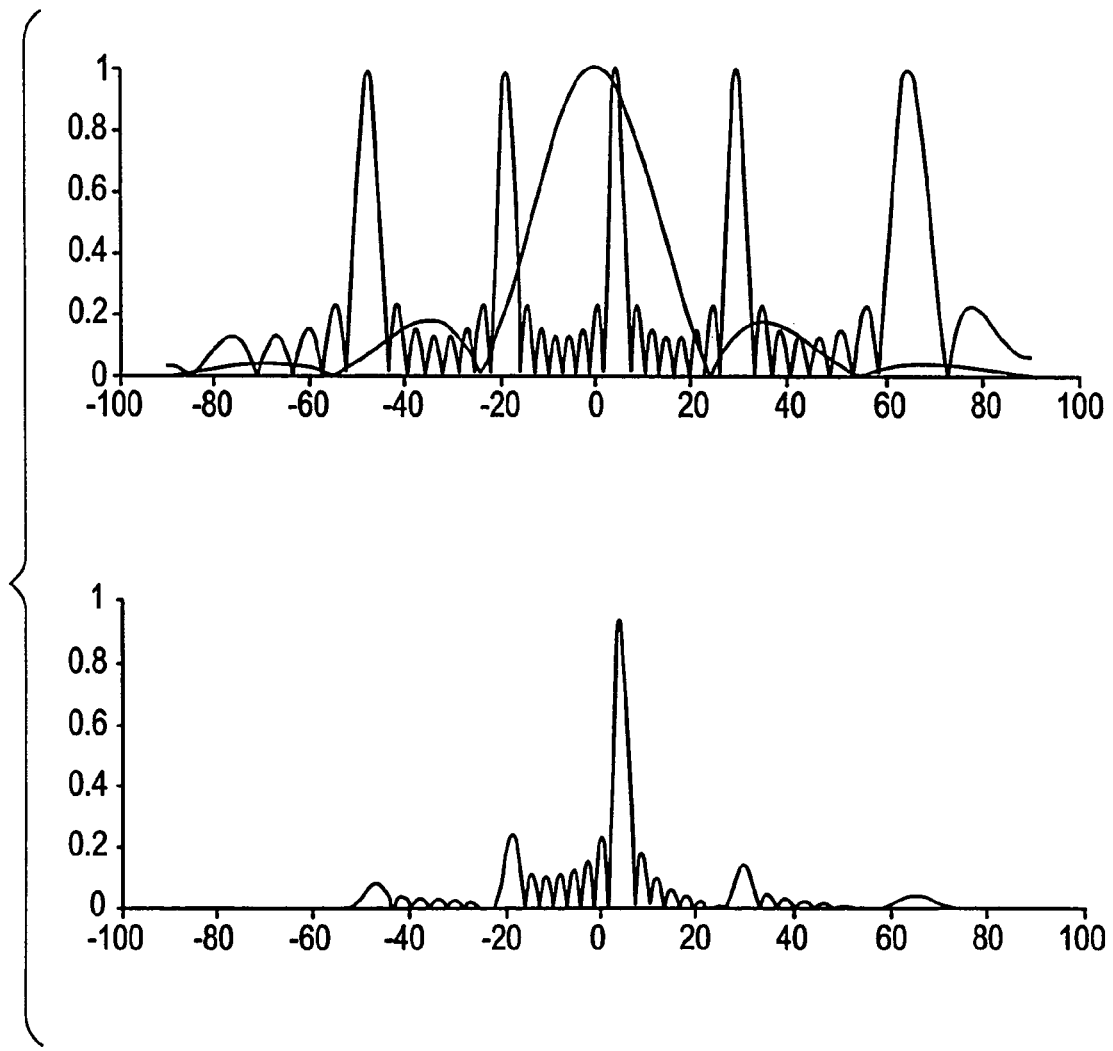
FIG. 17 is the same as FIG. 16, with the array beam steered to an angle at which a grating lobe exceeds the highest sidelobe. The thinned array of FIG. 16 should not be steered beyond $\pm\arcsin(\lambda/5d)$ ($\pm 4.7°$ for the example used) if grating lobes are to be suppressed.
Figure 18:
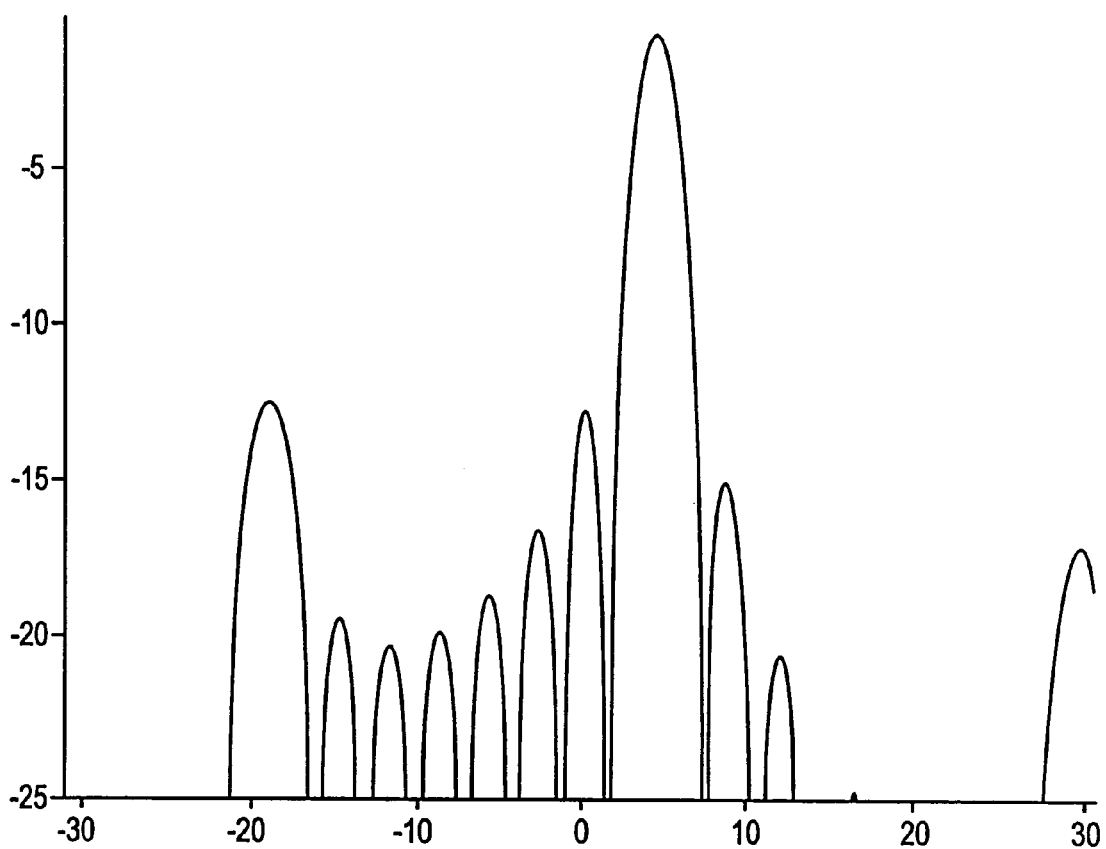
FIG. 18 shows the pattern of a beam steered to the point where the grating lobe problem appears. This is FIG. 17b plotted in dB.

In FIG. 17 the same array is used as in FIG. 16, but the receiver element signals are combined with a phase taper that steers the beam to x=0.2 or θ=4.71°. In FIG. 17b, we see that the grating lobes are not completely suppressed, with the largest one at x=−1+0.2=−0.8 or θ=−19.18°. FIG. 18 shows this in decibels. The worst-case grating lobe is attenuated by at least 12 dB, even in the stressing case of extremely narrow band operation. These Figures were produced in MATLAB, using the following software (m-file):

```
%MPATTERN  mpattern.m  Script to plot monostatic patterns vs. theta
Mt = 90; wave_length = 0.77 ; d=1.875 , N=8,
k=d/wave_length
t = -Mt:0.1:Mt;
tr = pi.*t./180;
x=k*sin(tr);
p=pi*x + eps; R=sin(p)./p;
 R=R.*cos(tr);
n=0:N-1;
```

```
xo=0;
xo=0.2;   % steered
e=exp(j*n'*2*pi*(x-xo));
 W=nanning(N);
 E=(2/N)*w'*e;
E = (1/N)*ones(1,N)*e;
subplot(211); plot(t,[abs(R);abs(E)]);
ER=abs(E) . *abs(R);   % Monostatic
subplot(212); plot( t, (abs(ER)));
figure(2); plot(t,20*log10(abs(ER)));
zoom on;
```

The values of d and λ used in the above example are representative for a transcranial Doppler application of the invention. If f=2 MHz is chosen for the center frequency, the wavelength is 0.77 mm. An 8×8 array with a width and/or length of L=15 mm, provides a one dimensional thinning ratio of 2 d/λ=4.87. A 15 mm square array with half-wavelength elements would require more than 15,000 elements. By thinning, this number was reduced to 52 provided that the angular field of view is limited to 2×4.71=9.42°. For a 1 cm array at 2 MHz, the hyperfocal distance (where the 3 dB focal region extends to infinity) is $L^2/4\lambda$=3.25 cm. For a 15 mm array, the hyperfocal distance is 7.3 cm. Thus, a fixed focus probe suffices for this application, but the quadratic phase distribution across the elements required to focus in depth should be added to the linear phase distributions required to steer the beams.

Using the configuration described above, the cluster of beams in FIG. 15 is used to approximately locate the desired point for collecting the blood velocity signal. This is done initially, and is repeated periodically, in "mapping dwells" that are interspersed with normal measurement dwells. For example the output of each beam in the cluster would be Doppler processed by performing an FFT or equivalent transformation on a sequence of pulse returns. The pulse repetition frequency (PRF) would typically be less than or equal to 9 kHz to unambiguously achieve a depth of 8.5 cm for the TCD application. In order to obtain a velocity resolution finer than Δv=2 cm per second (to distinguish brain death), a dwell of duration as long as T=λ/(2Δv)=20 ms, or 170 pulses at 8.5 kHz, may be desired in the measurement mode. During monostatic mapping, 21 beams are scanned. If a mapping dwell is to be completed in 20 ms, only 8 pulses per beam are available, and an 8-pulse FFT would be utilized for each beam position.

The example shown in FIGS. 16 through 18 was an 8 by 8 receiver array forming a 5 by 5 cluster of beams. This is an example of an approximate rule of thumb for this invention, that an N element linear array is recommended for use in producing N/2+1 beams for N even and [N+1]/2 beams for N odd. Thus, a 16 by 10 element rectangular array would preferably be used to form a 9 by 6 cluster of beams, though the actual number of beams formed is arbitrary.

Because receive beams are formed only in a limited angular region, a wide-angle receiver element pattern (which usually implies a small element) is not required. In fact, the size of the receiver element can be as large as the element spacing. Thus the receiver array is "thinned" only in the sense that the element spacing exceeds a half wavelength. Since the element size also exceeds a half wavelength, the array area is not reduced. It is thinned only in terms of number of elements, not in terms of receiver area. Consequently, there is no reduction in signal-to-noise ratio, nor a requirement for increased transmitter power.

Figure 19A:
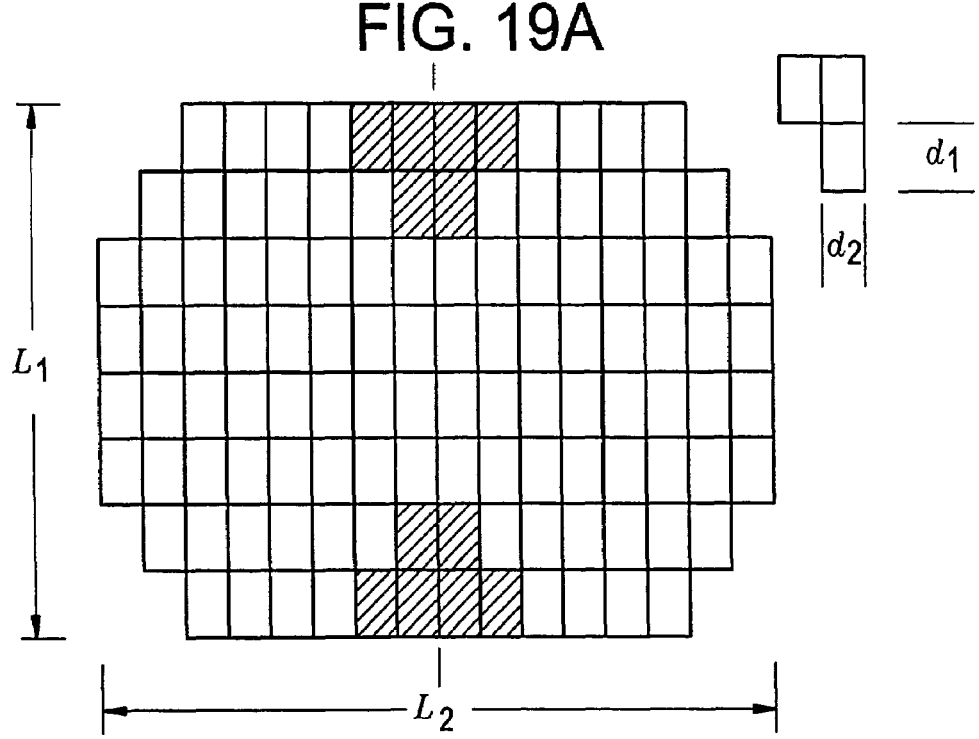
FIG. 19 shows a dual 52-active-element ultrasound transducer array example (similar to that in FIG. 14) with a total of 116 elements, 52 of which are used at a time.
FIG. 19B shows that the two sub-arrays are in two different planes, tilted to reduce the overlap between beams from the two sub-arrays and maximize the azimuth angular field of view.
Figure 19B:
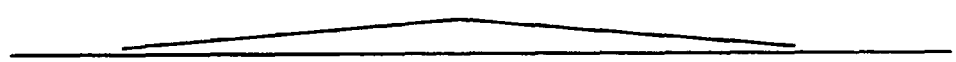

FIG. 19 illustrates a means for increasing the angular field of view in the azimuth direction by extending the array horizontally. A similar scheme could be used vertically to extend the elevation F.O.V. The 52-element array of FIG. 14 becomes a single panel of the extended array. One panel is active at a time in FIG. 19. The beamwidth for FIG. 14, in radians, is nominally given by λ/L. At a range or depth of R, the cross range resolution is Rλ/L (typically 3 to 5 mm). The F.O.V in millimeters at that same range is less than N/2+1=5 times that beamwidth. If a second panel is used in a planar configuration, the second panel translates the beam pattern to the right (or left) by the width of the panel, L=$L_2$/2 (typically 8 mm). The field of view can be extended by more than this (it can even be doubled) by tilting the two panels in opposite directions to minimize the overlap in coverage of the two panels.

FIG. 19, with $L_1 \approx L_2$, simultaneously provides: (1) a large F.O.V. in the $L_2$ direction to allow for the simultaneous monitoring of two blood vessels more than an inch apart, (2) a large active array area for high sensitivity, and (3) a number of active elements below 60 and a total number of elements below 120. An alternative, shown in FIG. 20, has the array on the surface of a segment of a cylinder. This uses 52 elements at a time with a total of only 84 elements (and hence only 84 cables). The $L_1 \times L_2'$ active array translates around the curved surface as the beam is scanned horizontally. If a symmetric F.O.V. extension (azimuth and elevation) is desired, a spherical surface could be utilized.

Figure 20:
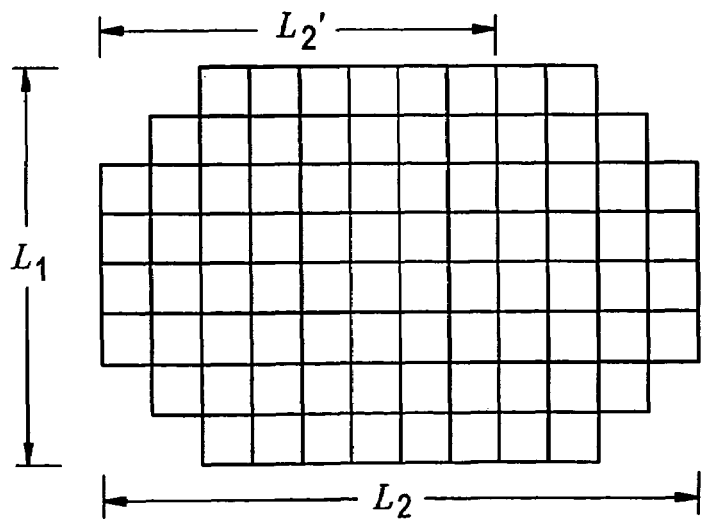
FIG. 20 shows a 52-active-element ultrasound transducer array example (similar to that in FIG. 14) with a total of 84 elements (52 of which are used at a time) and with a slightly convex cylindrical shape. The indicated $L_1 \times L_2$' sub-aperture would be activated for the formation of beams pointed to one side.

FIG. 21 is an overall block diagram depiction of the overall blood flow monitor. Most functions are performed by means of software in the digital processor. Naturally, one of ordinary skill in the art can readily program the processor to perform functions described herein using equations set forth herein and routine programming techniques. A possible implementation of the analog processing is diagrammed in FIG. 22. The A/D converter can be a bank of converters or one or more converters multiplexed amongst the 52 channels. If an extended array such as shown in FIG. 19 or 20 were used, a switch would be included between the 52 processing channels in FIG. 22 and the actual elements. Note that the 52 element array of FIG. 14 represents an 8×8 array with corners removed (52=8×8−4×3). Other possibilities include a 24 element array (24=6×6−4×3), a 120 element array (120=12× 124×6), etc.

The transmitter produces pulses for each active element at a pulse repetition frequency (PRF) of 8,500 pulses per second. Each pulse will be at a frequency of $f_o$=2 MHz and will have a bandwidth, B, of at least 250 kHz (e.g., a pulse no more than 4 microseconds long).

For measurement, only one or two beam positions need be insonated by a single probe. For mapping, many beam positions must be insonated, with several pulses on each for moving target indication (MTI) and/or Doppler processing. A measurement frame duration longer than 20 milliseconds (170 pulses at an 8.5 kHz PRF) may not be necessary because of the non-stationary (pulsed) nature of human blood flow. Mapping, requires several (4 to 11) pulses per beam position and many (e.g., 21 to 36) beam positions per frame. Since the Doppler resolution for mapping is not as fine as in the measurement mode, longer mapping frames can be used. If only 21 beams are formed with 8 pulses on each or if up to 34 beams are formed with only 5 pulses on each, a frame duration of 20 ms can be maintained even during search and mapping.

Figure 22:
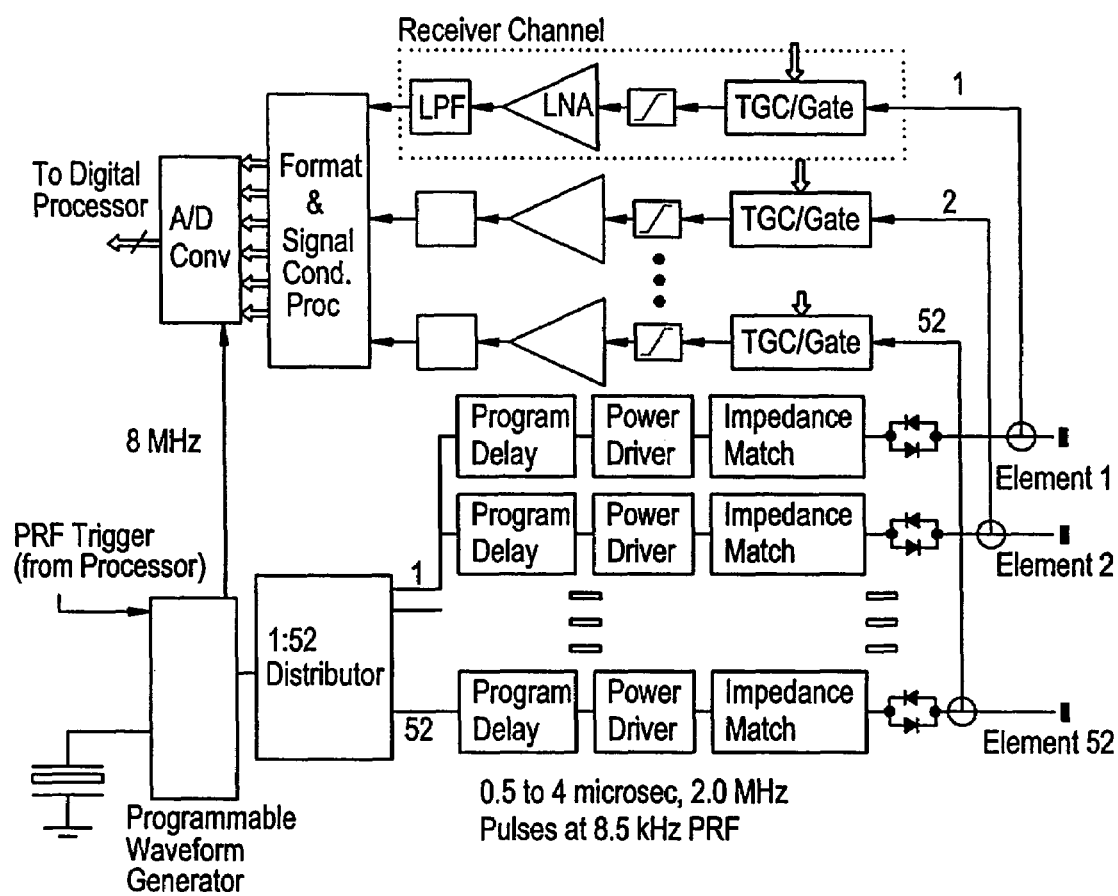
FIG. 22 is a block diagram of one possible embodiment of the analog Transmit-Receive Electronics for an Ultrasound Imaging Sensor and Blood Monitor.

FIG. 22 shows 52 identical receiver chains comprising
1. Processor controlled time gain control and time gate (open for up to 26 microseconds for each pulse).
2. A limiter for dynamic range control.
3. A low noise amplifier (LNA).
4. A low pass filter (to pass $|f|<f_o+B/2$ (e.g., $|f|<2.125$ kHz) and reject $|f|>5.87$ kHz by at least 40 dB (assuming $f_o$=2 MHz and B=250 kHz).

A/D conversion (typically 12 to 16 bits) is performed at an 8 MHz rate for each channel in FIG. 22. This keeps the analog filtering requirements extremely simple. It also permits extremely large bandwidths (up to 2 MHz) and time-delay steering. For narrower bandwidths and phase-shift steering, bandpass analog filtering and much lower sampling rates (determined by B rather than $f_o$) could be used. For the 8 MHz sampling rate, either time-delay or phase-shift beam steering can be utilized (depending on signal bandwidth). FIG. 22 depicts time delay steering for the transmitter. The distance from each array element to each focal point (each beam center at a nominal depth (e.g., 60 mm for TCD) would be pre-computed and stored either as a time delay or as a phase shift (depending on the type of steering) for each element for each beam. If phase shift steering were utilized on transmit, the transmitted signal could be created digitally in the processor, followed by D/A conversion for each element. Hence FIG. 22 represents only one possible embodiment of the invention.

An example of the digital receiver processing for the case of an 8 MHz sampling rate per channel is described below. The input is 208 12 or 16 bit samples per pulse (8 samples per microsecond ×26 microseconds to allow for a 4 cm deep radial mapping field of view), 8,500 pulses/second, and 52 channels. This results in a maximum average rate of 52×208× 8500=91.9 MegaSamples per second (or 1.84 million samples in a 20 ms frame). During measurement, the range interval can be narrowed to less than 1 cm, reducing the number of samples per pulse to 32. The average rate for measurement and monitoring becomes 14 megasamples per second. The receiver processing steps are as follows:

Buffer (to allow subsequent processing to be performed at the average rate).

Digitally Down Convert to Baseband (make I and Q). 52 channels in parallel. Multiply input samples by samples of a 2 MHz cosine wave and sine wave to create In-phase and Quadrarture samples, respectively. Since the samples are ¼ cycle apart, the multiplicands are all 0, 1, or −1, and hence no multiplications are needed. If r(j,p) is the real $p^{th}$ sample from the $j^{th}$ channel, the complex low-pass signal, s(j, p), has a real part for p=0, 1, 2, 3, 4, 5 . . . given by r(j,0), 0, −r(j,2), 0, r(j, 4),0, . . .

and an imaginary part given by

0, −r(j,1), 0, r(j,3), 0, −r(j,5), . . .

This provides a data rate 2 times the input rate because the data is now complex.

Pre-Decimation Low-Pass Digital Filter. Filter 52 complex channels. Pass $|f|<B/2$, reject $|f|>r-B/2$, where r is the sampling rate after sample rate decimation (e.g., 1 MHz). If B=250 kHz, r could be as low as 500 kHz. If B is large, r could be 2 or 3 MHz. If receiver phase-shift steering were to be performed, the output samples would be computed at the decimated rate. If receiver time-delay steering is to be used, we output 8 million complex samples per second and postpone sample rate decimation until after beam formation.

Perform MTI or create coarse Doppler cells. For every channel and every range sample, either digitally high-pass filter the sequence of pulse returns to suppress clutter from tissue and bone or perform 52×208 8-point discrete Fourier transforms (DFTs or FFTs) for each mapping frame. (Six points of the 8-point complex DFT provides 3 positive and 3 negative coarse Doppler cells.)

Perform Digital Beamforming. Case 1: Time Delay Beamforming with Sample Rate Decimation uses a set of pre-computed time delays to reduce 52 complex channels with 208 samples per pulse to one of M (e.g. 21) complex beam outputs with 25 samples (range cells) per pulse. The example given here assumes 8:1 decimation. The maximum delay is slightly less than 0.75 μs=6 T, where T=1/8 microsecond is the time between input samples. For a given pulse return, the $k^{th}$ sample (k=1, 2, ..., 25) of the $i^{th}$ beam, i=1, 2, ..., M, is denoted by b(i, k). The $p^{th}$ sample (p=1, 2, ..., 208) of the j th input channel (=1, 2, ..., 52) is denoted by s(j,p). Let $d_{ij}$ be the delay required for the signal in channel j to produce beam i.

For a given pulse return, the $k^{th}$ complex 1 MHz rate output sample for beam i is $$b(i,k) = \sum_{j=1}^{52} \{a_{ij}s(j, 8[k+1] - b_{ij}) + (1 - a_{ij})s(j, 8[k+1] - b_{ij} - 1)\}$$

where $b_{ij}$ is the integer part of $d_{ij}/T$ (between 0 and 6) and $a_{ij}$ is the fractional remainder (between 0 and 1). Determine power or amplitude in each output Doppler bin as $I^2+Q^2$ or its square root:

Case 2: Phase-shift beamforming of already decimated data involves only a sequence of inner products of 52-dimensional complex vectors of element values with a complex vector of representing the required phase shifts.

Display Coarse Blood-Vessel Color-Flow Map. Coarse blood vessel map is the set of range, azimuth, and elevation cells with high power, with 6 Doppler values. Blue and red represent positive and negative Doppler, with saturation related to radial velocity and intensity related to power.

Initialize Acquisition. The user, looking at an azimuth-elevation Coarse Map (with depth automatically truncated to a set of values that should include the MCA), moves the transducer and looks for a high-intensity, saturated spot. He can center the probe on that spot or he can have a device of the present invention display a range interval corresponding to the ACA, in which case he can make sure that both vessels are well within the angular field of view of the probe.

Acquisition and Tracking of one or two points being monitored. This is done with a single transmit beam focused on the spot identified above for several frames. Digital Down-conversion, low-pass filtering, and MTI are performed as before, but beamforming is different. Five receive beams are simultaneously formed. These are a sum beam and four monopulse difference beams, all steered to the same point as the transmit beam. Each monopulse beam is equivalent to the difference between the outputs of a pair of beams displaced on opposite sides of the focal point. The four monopulse pairs are in 45 degree intervals with the first being horizontal, and the third being vertical. The monopulse-difference output with the largest magnitude is divided by the output of the sum beam. The imaginary part is the "monopulse ratio" used to re-steer the beam (in the difference pair direction) so that it is better centered on the vessel. This procedure can be repeated in an effort to drive all four monopulse ratios to zero.

Measurement and Tracking. Tracking continues as described above during the measurement mode. Measurement is made with fine Doppler resolution (128 point FFT) applied to only the sum beam. In a 15 ms frame, data from 128 pulses are collected (52 channels, 6 range samples). The pulses are Hamming weighted and FFTd. This produces 128 Doppler bins (for each range bin and element), 66.4 times a second. Real sum beam outputs would then be produced (using monopulse-guided steering) for each of 64 to 126 of these Doppler bins.

Track maintenance and re-acquisition. Tracking is continued in parallel with measurement. If a monopulse ratio suddenly deviates far from zero and is not brought back to zero in one or two iterations, loss of track is declared. Re-acquisition is attempted autonomously by re-steering the beam by an amount determined by correlating a current color flow map with a stored earlier version (from before track was lost). If this is unsuccessful, (monopulse ratios do not all converge to zero) an alarm is sounded so that the user can return to repeat initialization of acquisition.

Correlation with previous maps will be periodically applied to prevent wandering of the data collection point along the vessel being tracked.

For tracking purposes, a monopulse tracking method described above can be used.

Figure 23:
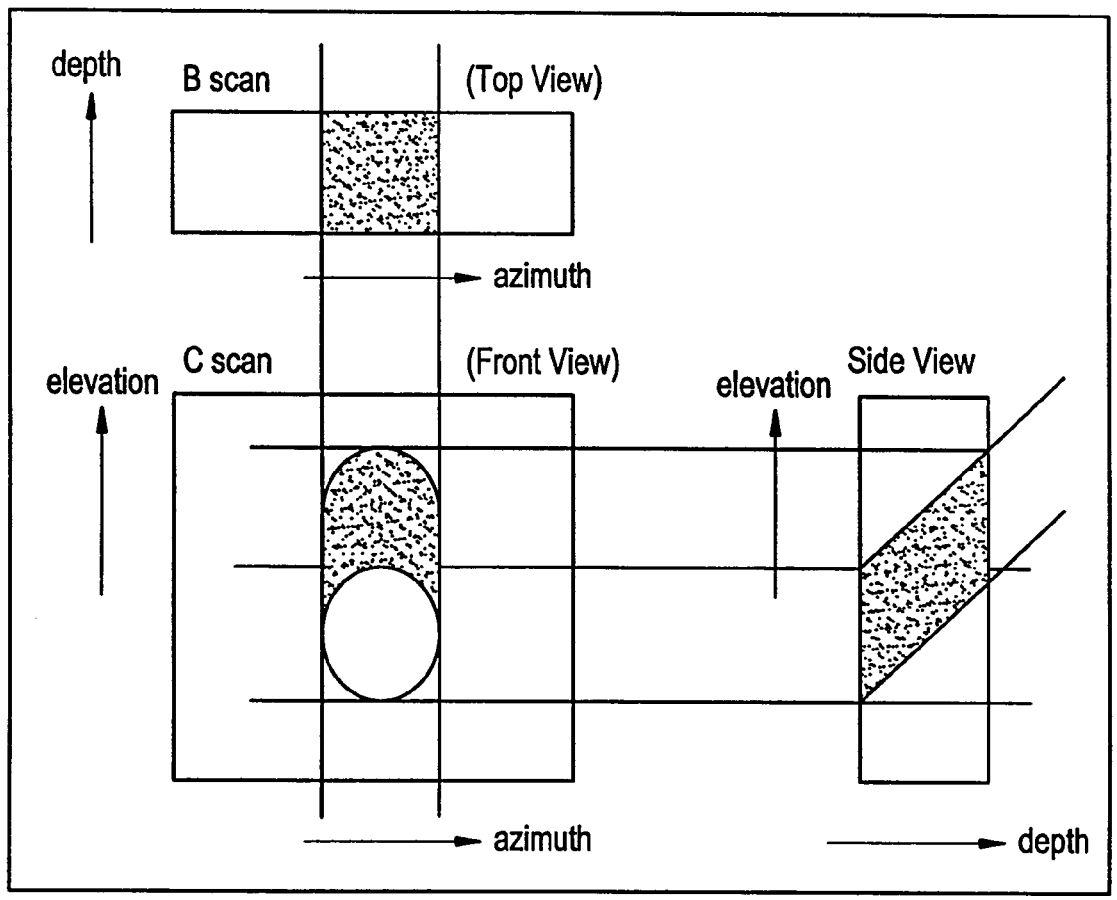
FIG. 23 shows the geometry involved in using azimuth monopulse to more accurately determine the cross-range location of a vessel. The measured radial velocity field or color flow map has been utilized to rotate and orient the azimuth and elevation axes so that the center of the vessel is vertical, at approximately zero azimuth. The black circular cylinder represents the location of all points within the spatial resolution cell that have a particular velocity.

FIG. 23 illustrates the segment of a vessel in a single resolution cell, after rotation. The resolution cell shown is not a cube because the range resolution might be finer than the cross-range resolution. The illustrated circular cylinder represents blood cells in a vessel reflecting energy at a fixed Doppler frequency. These represent a cylindrical annulus of blood cells, at a constant distance from the vessel wall, moving with approximately the same velocity. In the single resolution cell of FIG. 23, the return at the highest Doppler would represent a line in three-dimensional space (the axis of the vessel) and hence a point on the azimuth axis after rotation. When applied to the highest Doppler output, the Sum beam would have broad peak at zero azimuth (a=0) and the monopulse ratio, r=Az/Sum, will be a linear function of the azimuth angle to which the array is phase steered:

$r(a)=ka.$

This result can be attained by applying the same phase across the aperture for the Az and Sum beams, but using the derivative of the Sum beam amplitude weights with respect to x and y respectively for the Az and El aperture weights.

Ultrasound systems include a beamformer and an image processor. The transmit waveforms from the beamformer are converted to acoustical energy, and the reflected acoustical energy is converted into receive signals by an array of transducer elements. U.S. application Ser. No. 09/926,665, assigned to the present invention and now allowed, describes one method of providing thinned arrays for use in ultrasound systems and is hereby incorporated by reference in its entirety. While the invention is described in terms of ultrasound applications, and in particular, Doppler ultrasound embodiments, the invention is not limited to Doppler Ultrasound operation, but is applicable to all active phased arrays, including sonar, radar, and coherent optics, regardless of whether or not Doppler processing is involved.

Antifocusing

Figure 24:
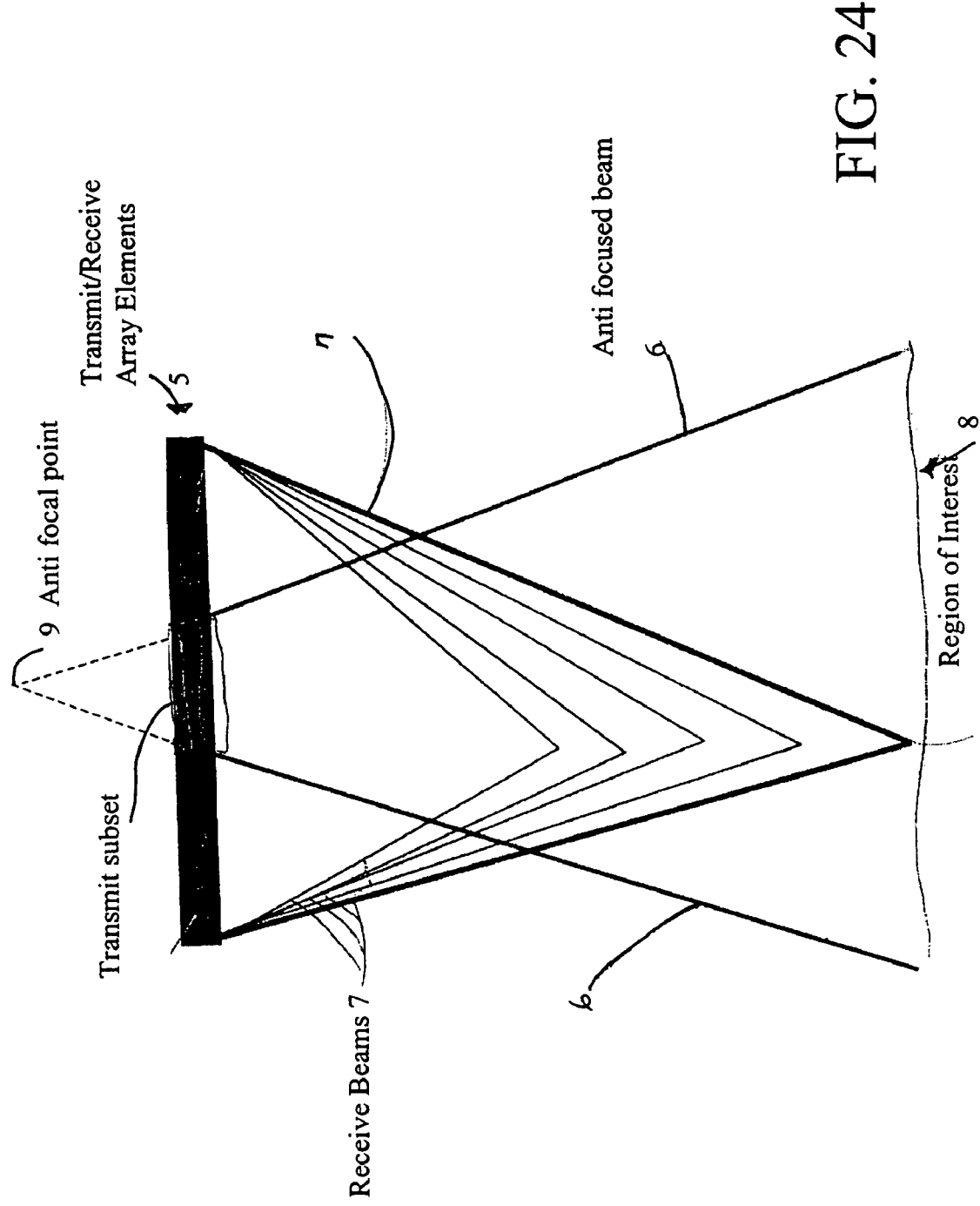
FIG. 24 is a conceptual diagram illustrating the antifocusing technique according to an embodiment of the invention.
Figure 25A:
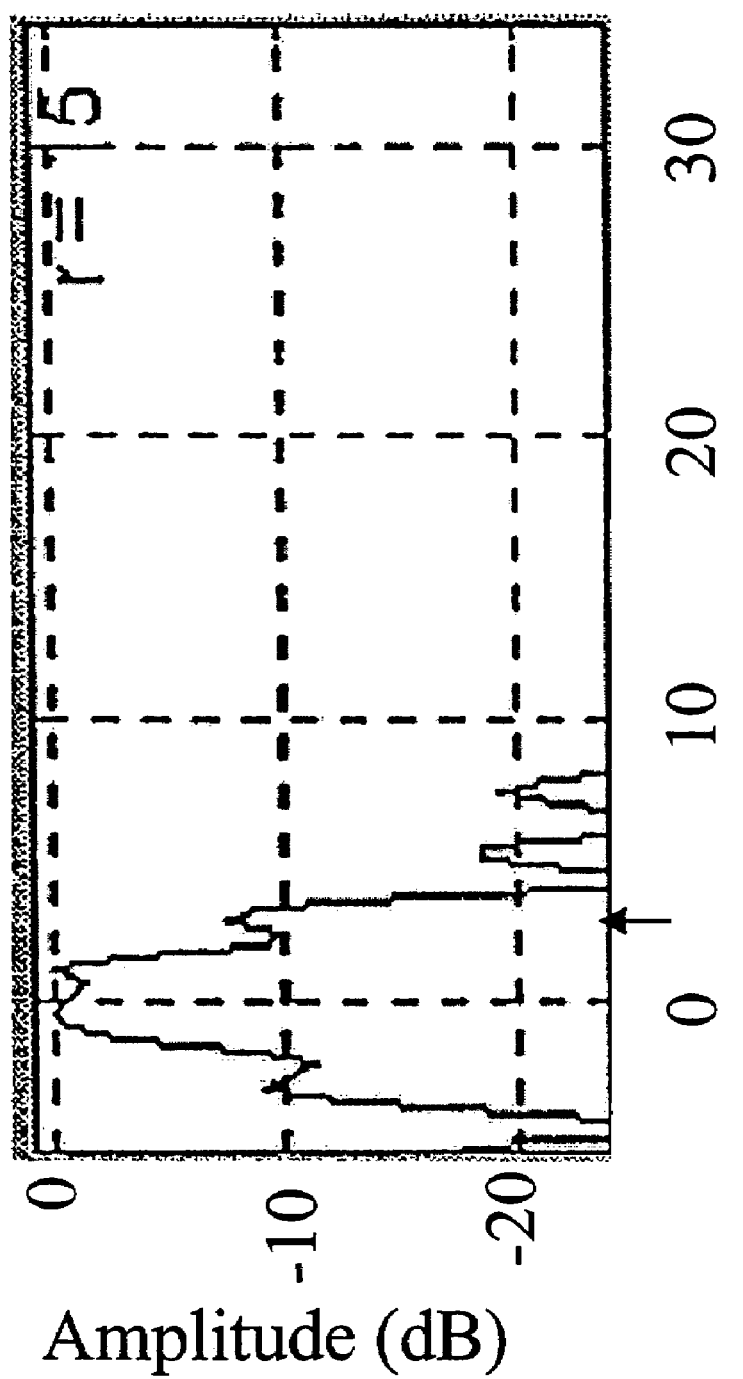
FIGS. 25(a-f) illustrates a transmitter pattern wherein pulses of energy are transmitted according to an embodiment of the invention at six different ranges and center focused.
Figure 25B:
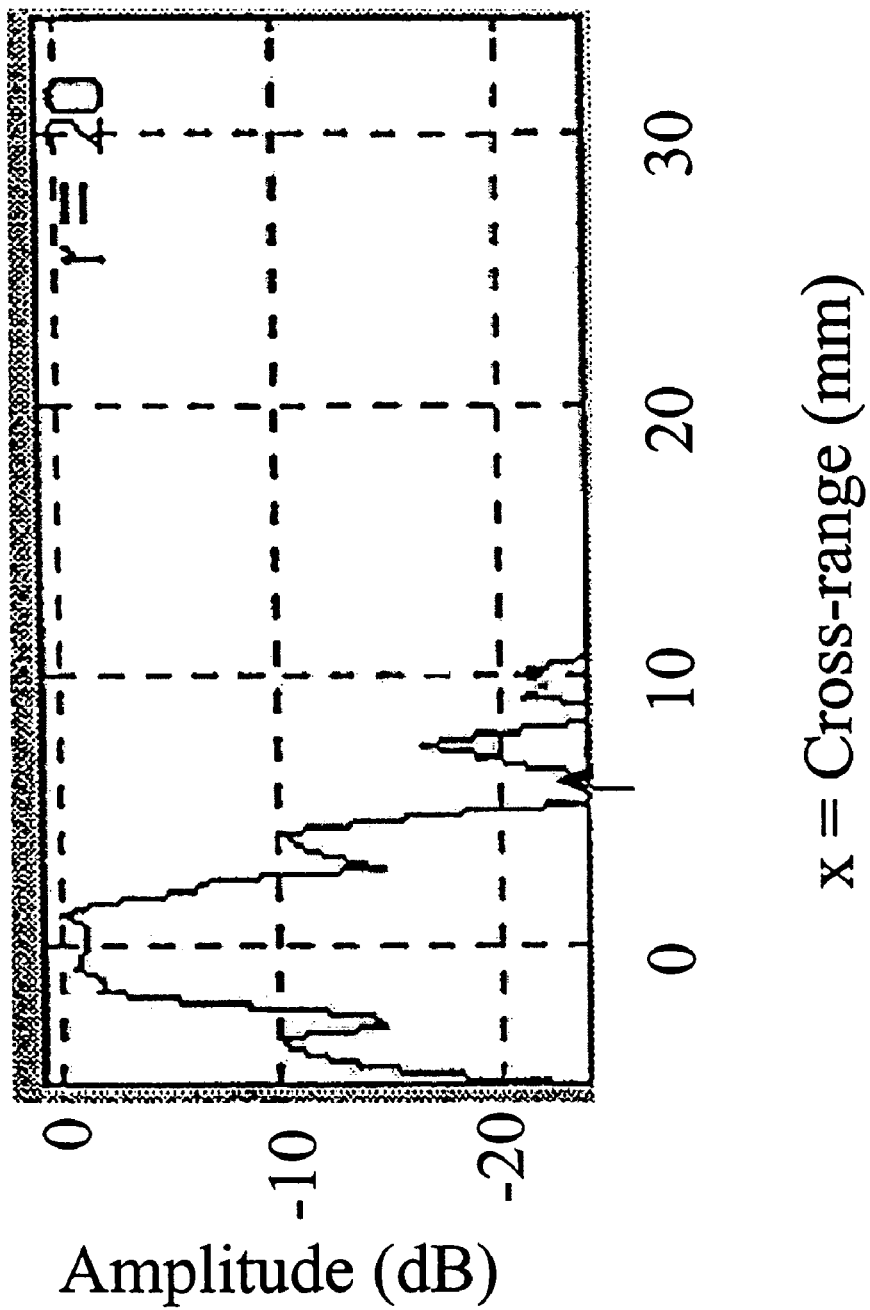
Figure 25C:
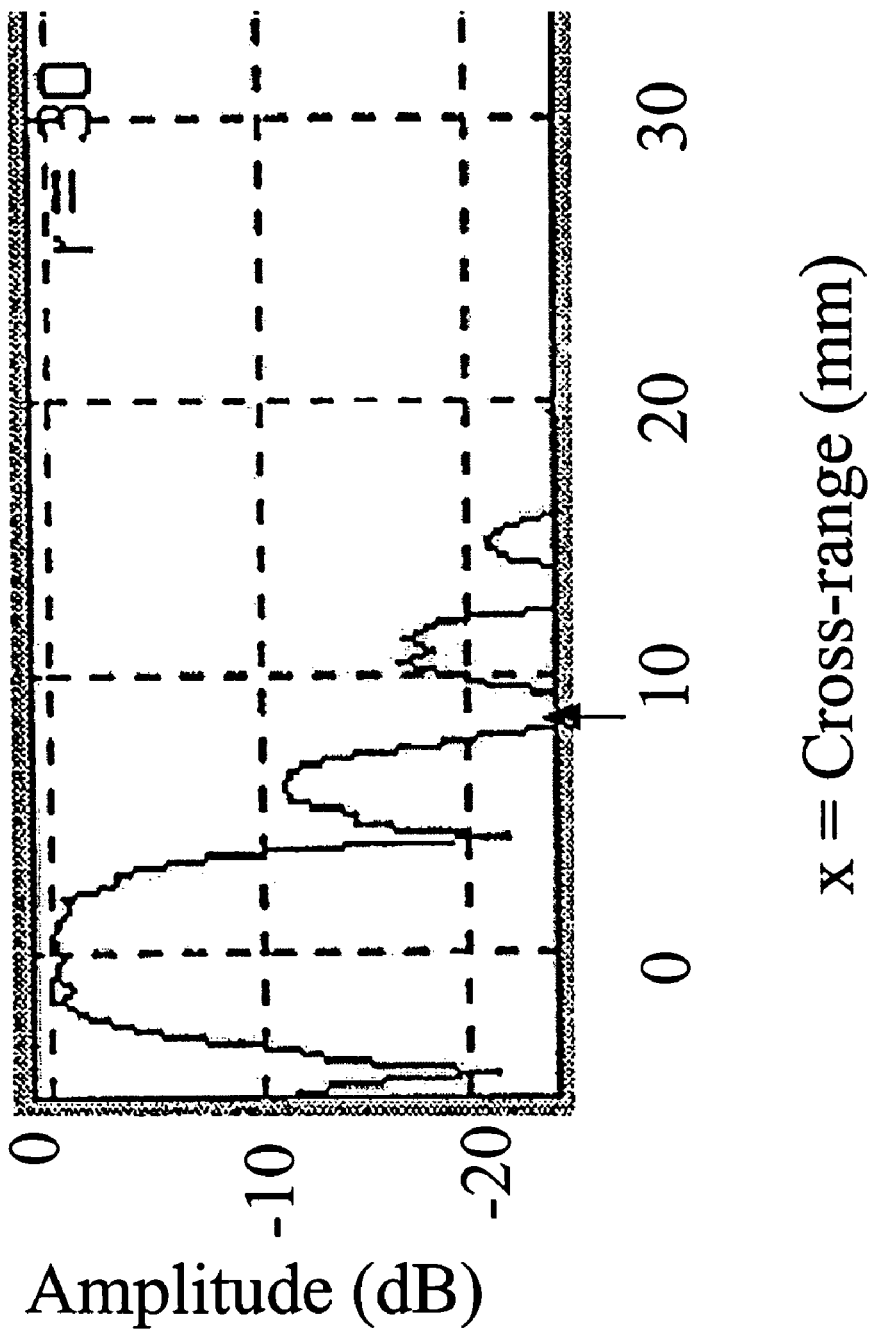
Figure 25D:
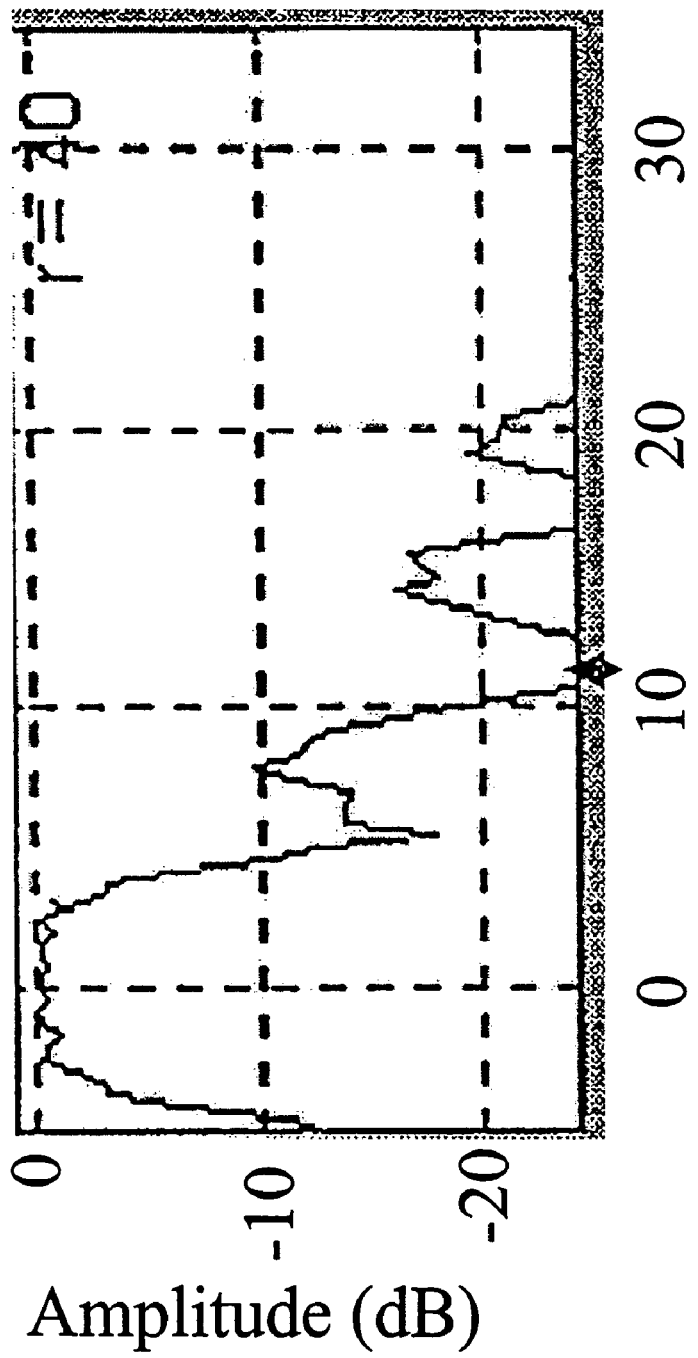
Figure 25E:
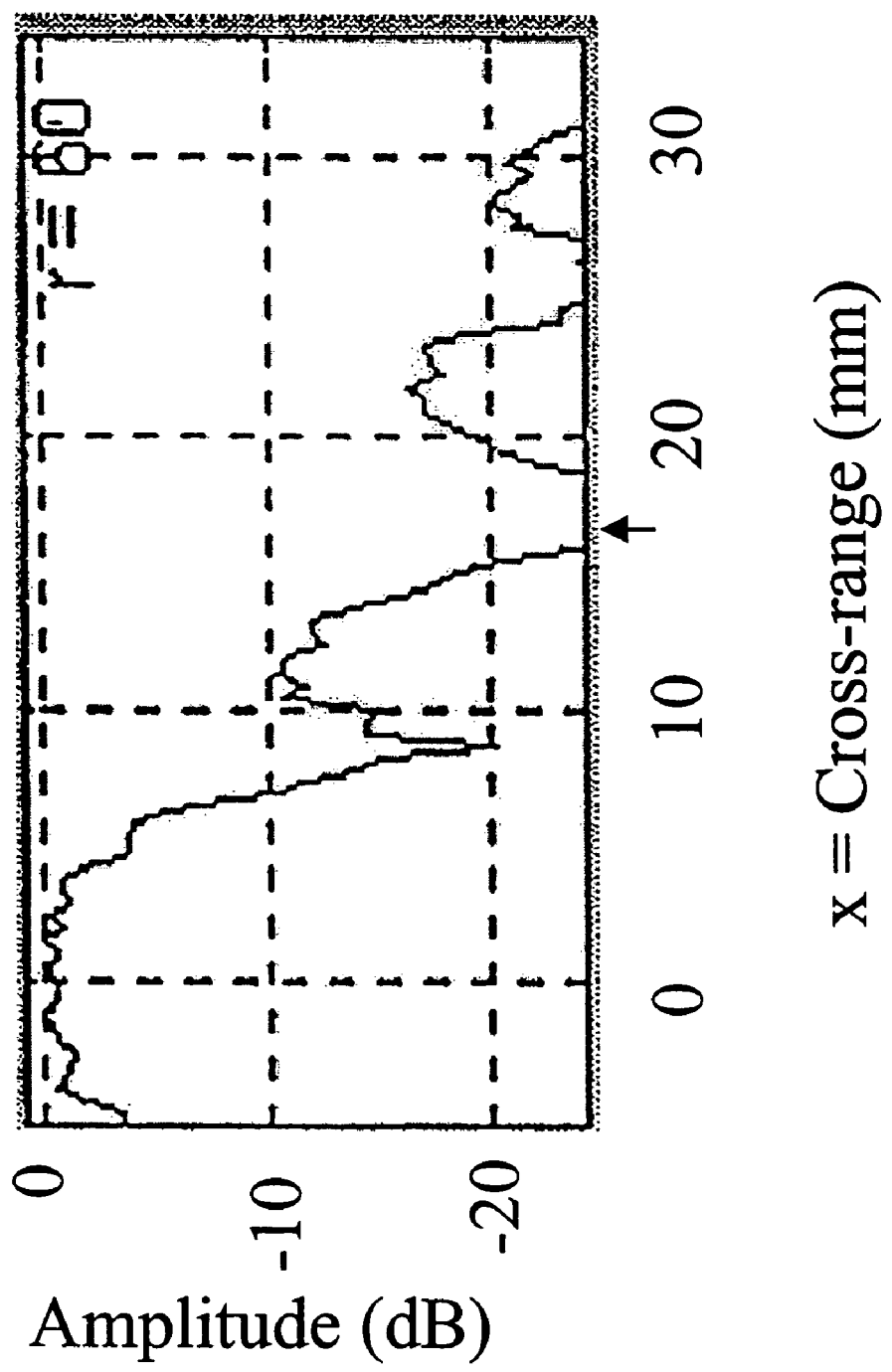
Figure 25F:
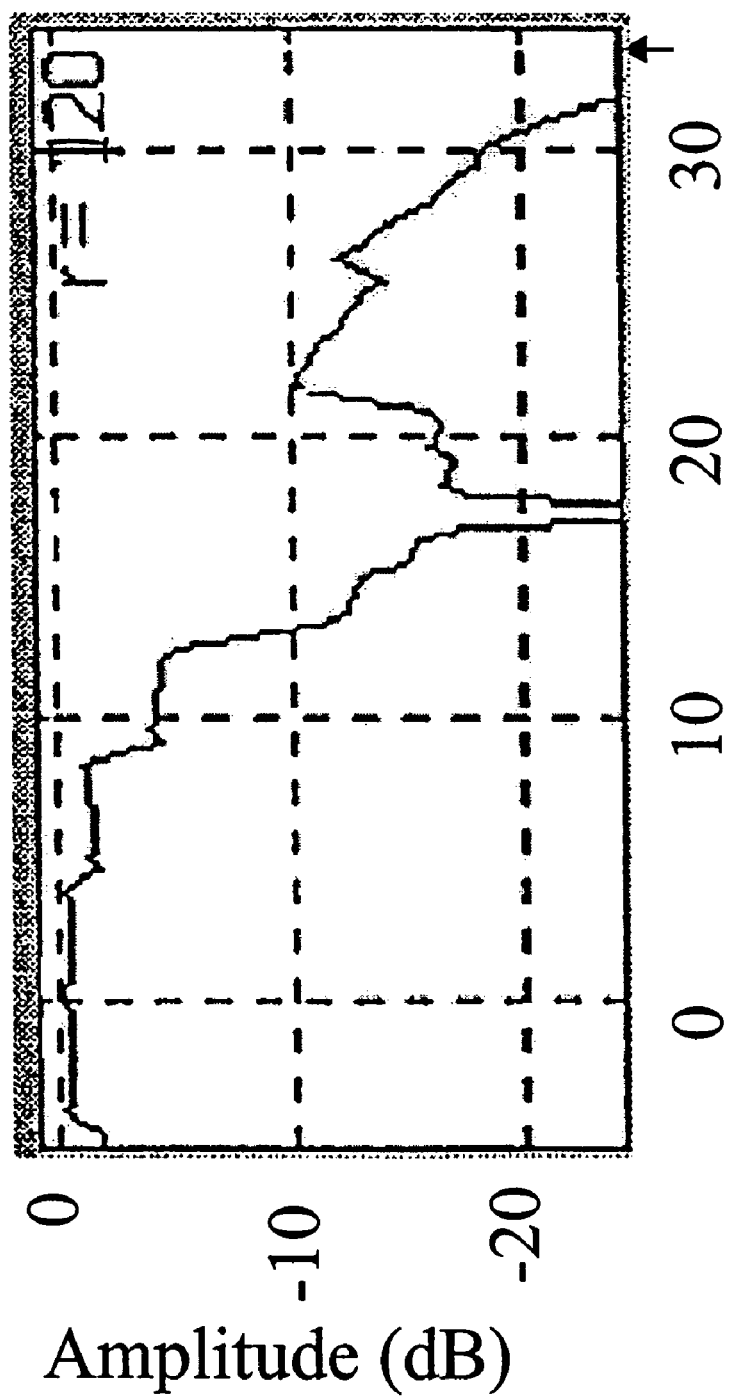
Figure 27A:
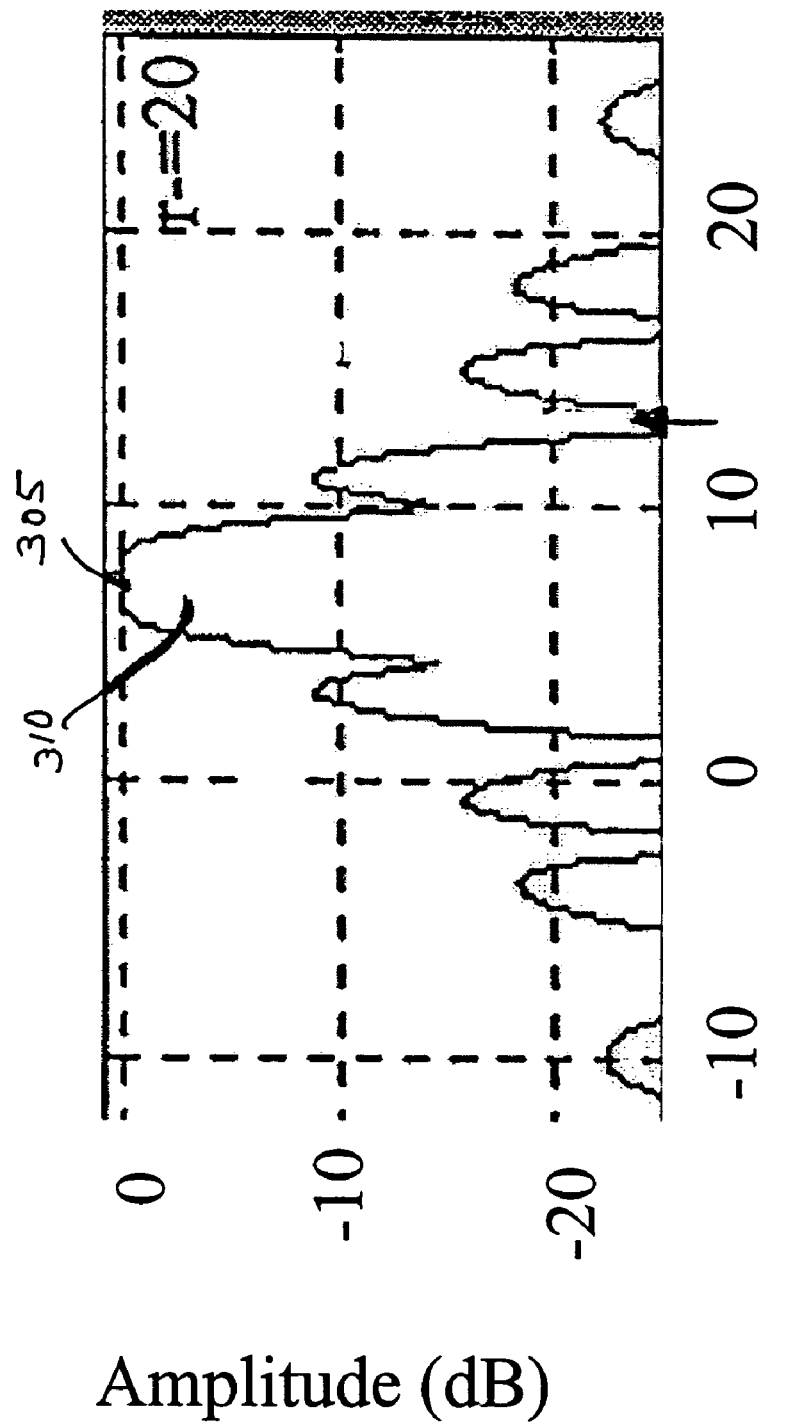
FIGS. 27(a-f) shows Matlab simulations of transmitter patterns according to the invention, when continuous waves are utilized for purposes of simplification of illustration.
Figure 27B:
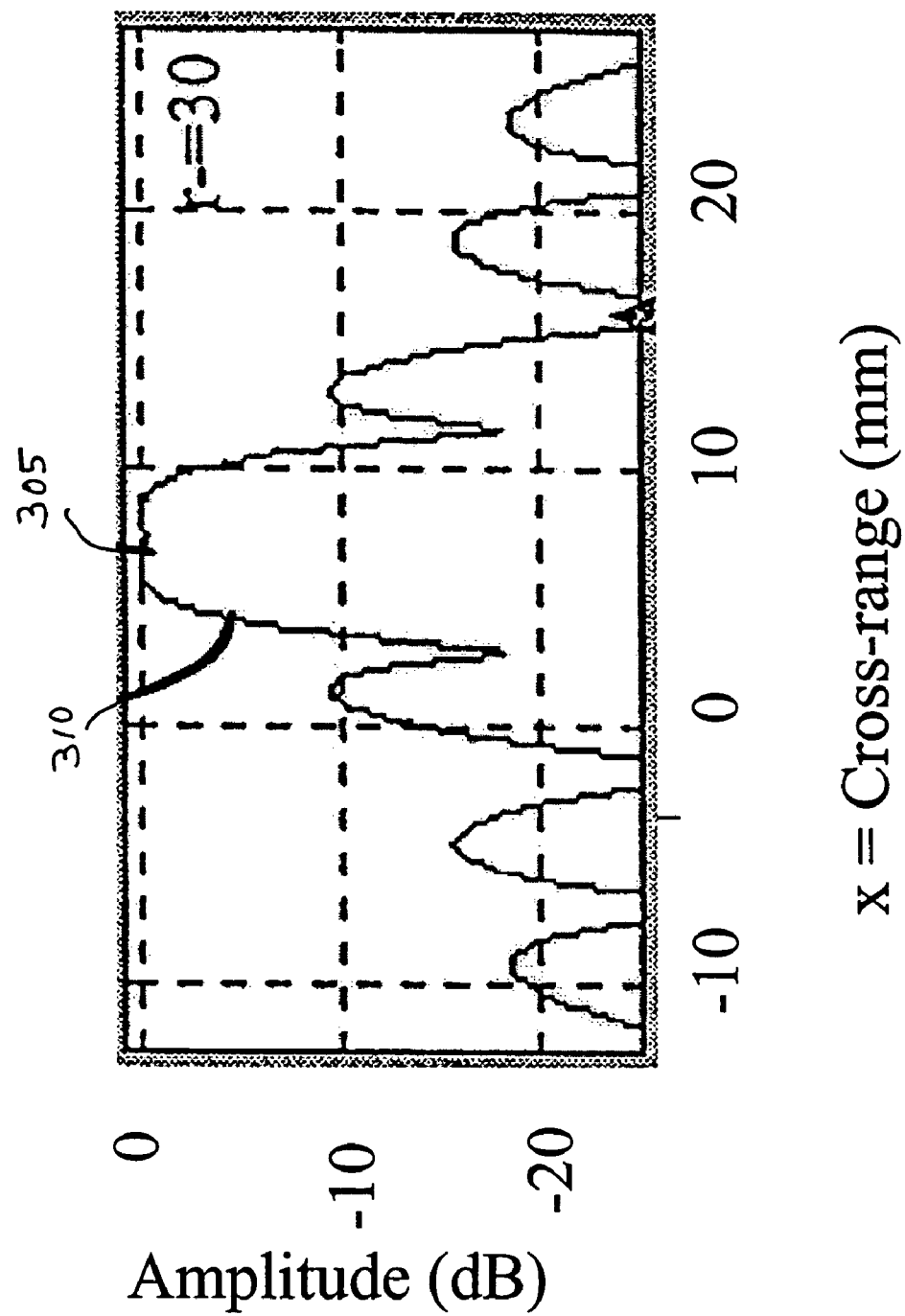
Figure 27C:
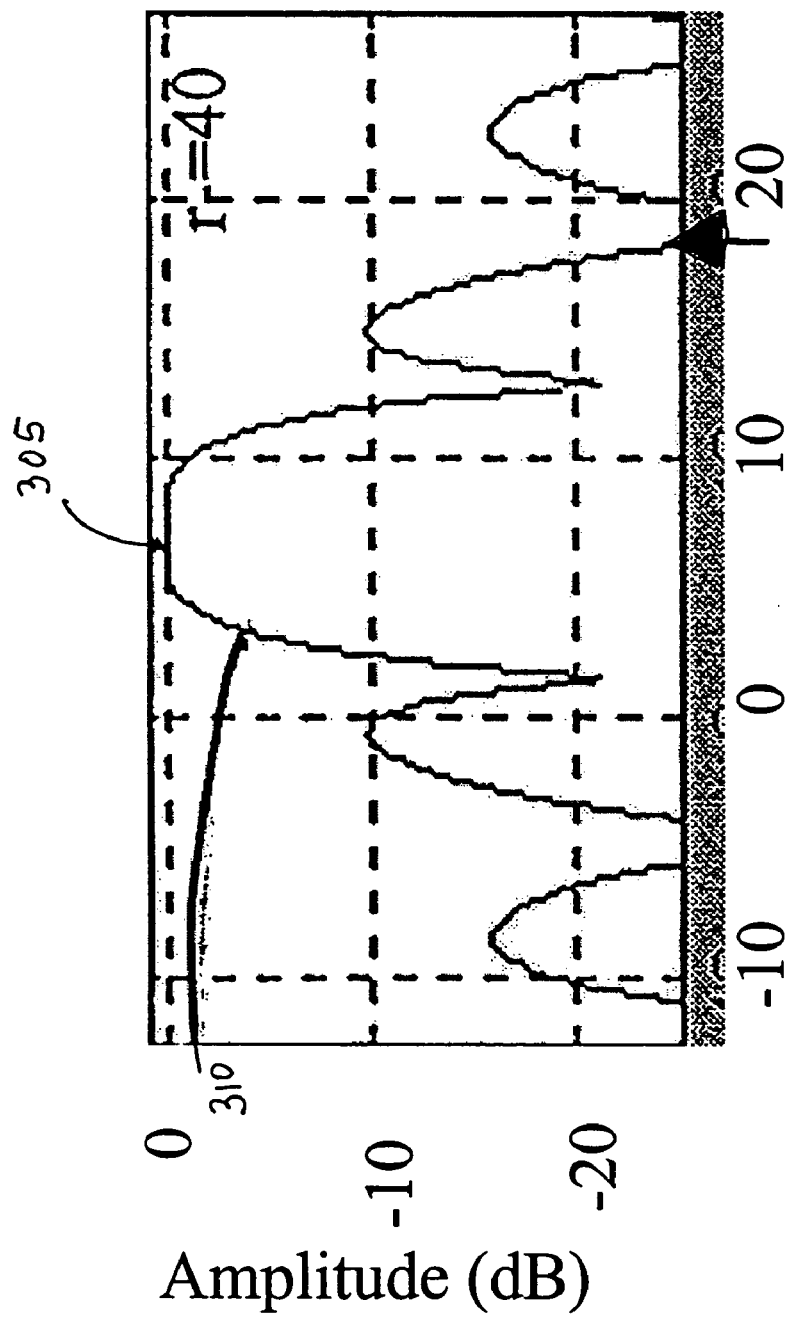
Figure 27D:
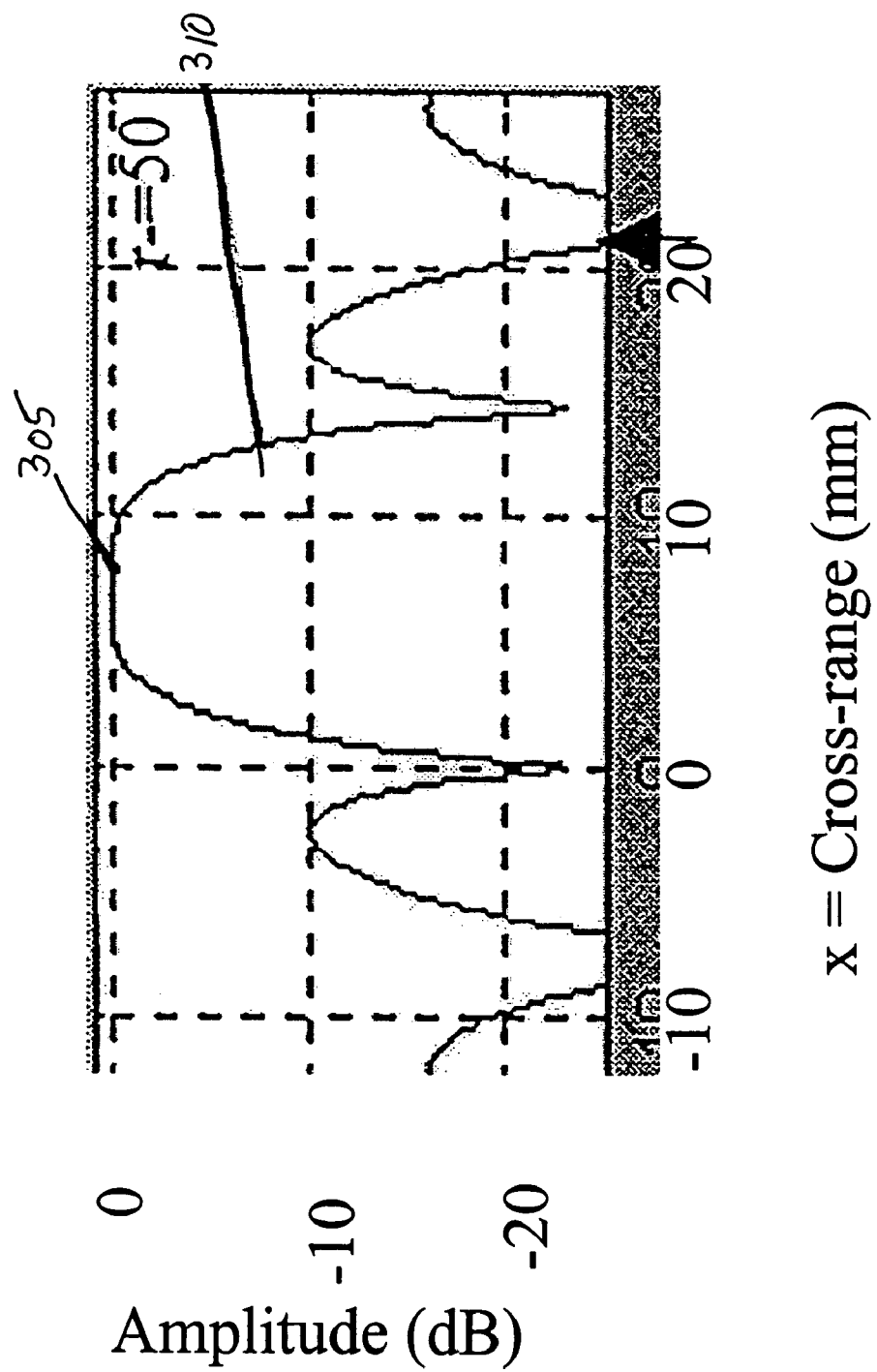
Figure 27E:
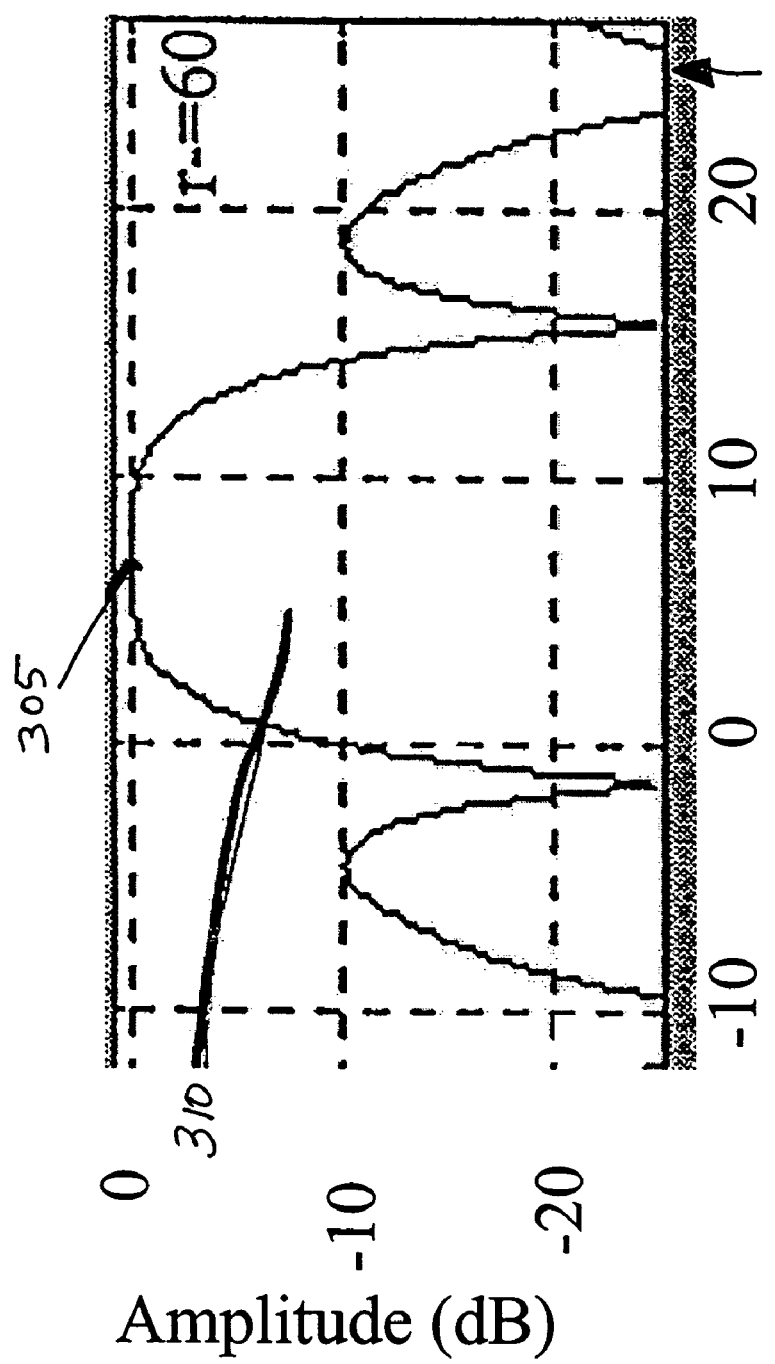
Figure 27F:
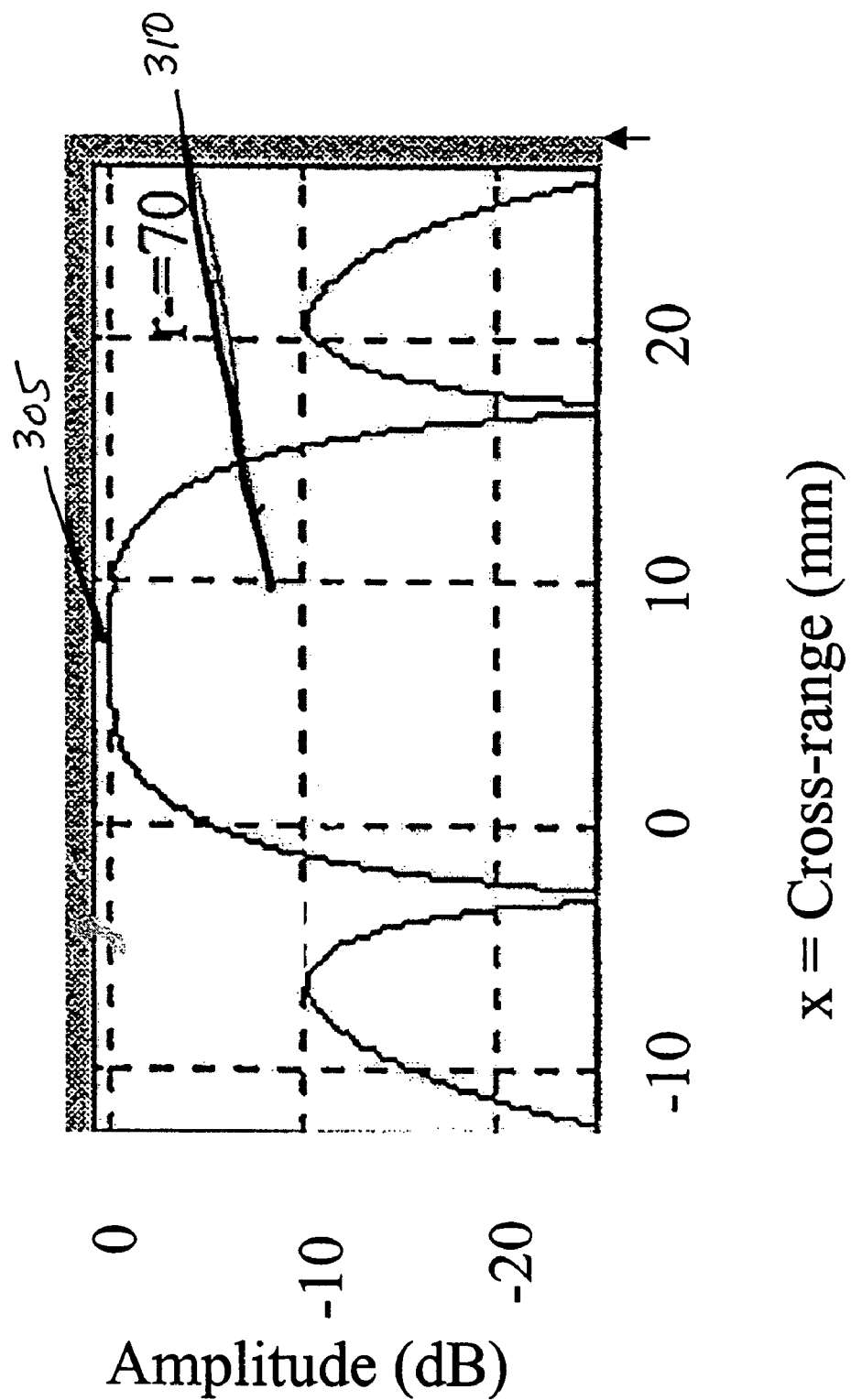

In imaging blood vessels, it is desirable to obtain a measure of blood volume flow in real time. Therefore, the problem of forming $N^3$ voxels in real time while dwelling long enough to measure blood velocity arises. According to an embodiment of the invention, a solution to this problem is provided by "anti-focusing" the transmitting array. FIG. 24 illustrates the concept of antifocusing. For purposes of this specification, antifocusing refers to configuring an array 5 to transmit a broad transmit beam 6 such that a large region of interest 8, for example a blood vessel of the human body, is insonated simultaneously. One method of accomplishing antifocusing the array according to an embodiment of the invention, is by introducing time delays that correspond to a diverging wavefront. Alternative embodiments of the invention rely on phase shifting to achieve the antifocusing effect. In any case, one embodiment of the invention employs the concept of antifocusing a transmitter array. An antifocused transmitter pattern is a pattern that simultaneously illuminates or ensonifies a plurality of receiver beams. In one embodiment of the invention, antifocusing is accomplished by employing time delays to the transmitter elements. The transmitter delays increase with the distance of the array element from the center of the array. These delays provide a wavefront that appears to propagate from the array as if it came from a point source behind the array. The location of this fictitious point source is the antifocal point 9 and its distance from the array center is the antifocal distance.

Reducing Grating Lobes

A significant disadvantage of known phased arrays is the unwanted presence of grating lobes and other unpredictable secondary intensity maxima which can potentially lead to ambiguities in the received signal. The need to reduce side lobes and grating lobes is common to all arrays reported to date. Several techniques including apodization, broad banding and the use of subsets of elements have been investigated to reduce the effect of side lobes. No effective technique has yet been developed to satisfactorily address the problem of grating lobes. U.S. application Ser. No. 09/926,666 of which this application is a continuation in part, addresses the problem of grating lobes. This phenomenon arises, in part due to the spacing between the elements of a transducer array. It is especially desirable in thinned arrays to reduce the effects of grating lobes. According to an embodiment of the invention, transmitter patterns are generated that have nulls where receiver grating lobes could lead to ambiguities in the received signal. In order to provide such nulls, transmit signal amplitudes are selected to maintain low transmit sidelobes in the regions of receiver grating lobes, thereby reducing the effects of the grating lobes.

Simplifying Processing

Figure 28:
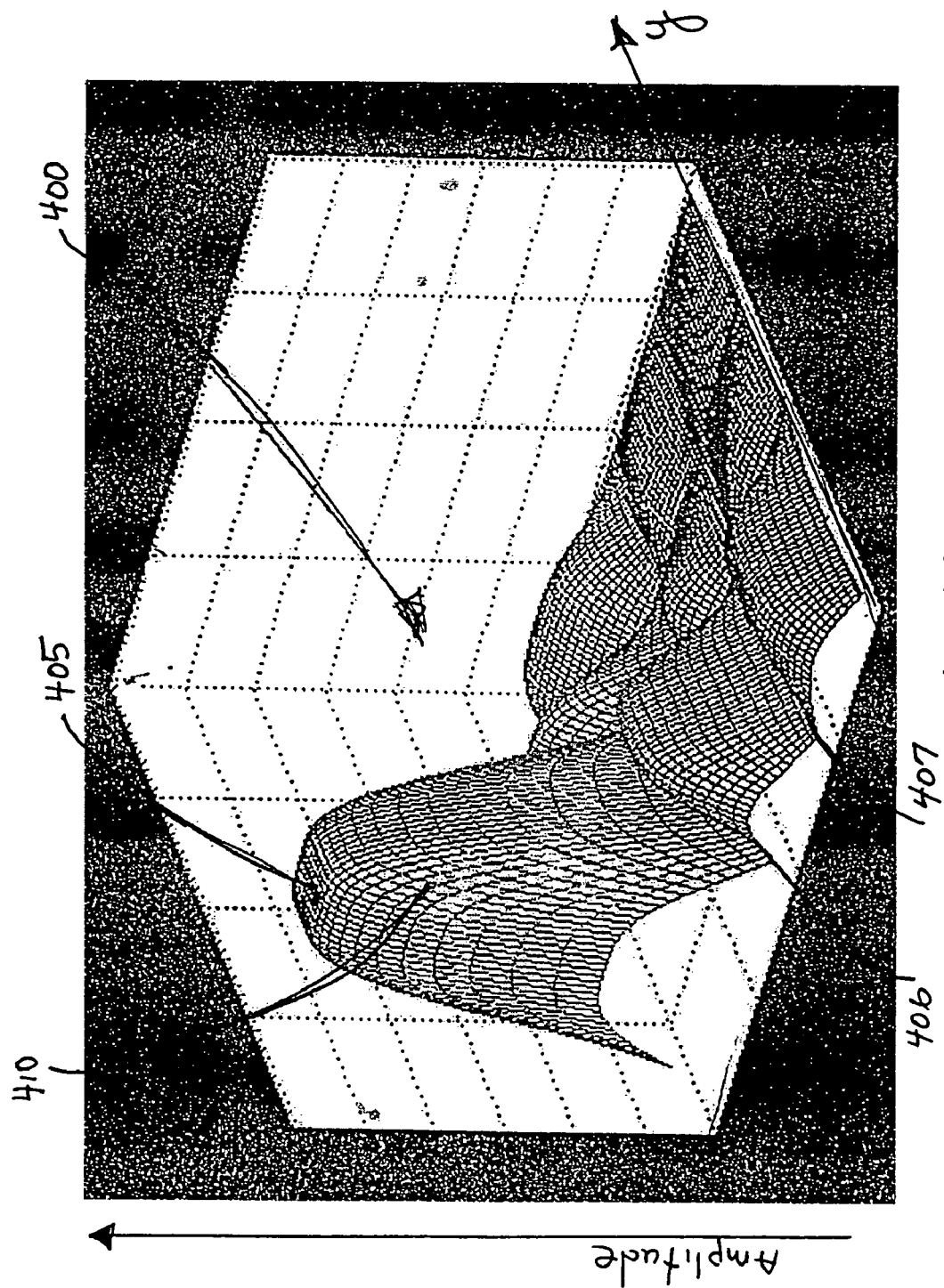
FIG. 28 is a 3-D illustration of the transmitter pattern illustrated in FIG. 27(e).

It is desirable to simplify the processing of received signals and to maintain the ratio of the received signal to noise and other types of interference, including grating lobes. An embodiment of the invention provides a transmitter pattern having a nearly constant amplitude over a broader angular region than would be obtained by transmitting a typical lobed pattern. Accordingly, received energy from that region remains relatively constant as the illumination of that area remains constant. This simplifies processing of the receive beam information. According to an embodiment of the invention, in order to simplify the processing of received beams, a transmit beam is formed which causes multiple receive array elements to receive equal reflected energy. FIG. 28 illustrates the general shape of the transmit beam according to an embodiment of the invention wherein the nearly constant amplitude portion of the transmit pattern is indicated at 405.

The transmitter pattern illustrated in FIG. 28 is formed by adjusting the amplitudes of the transmit array elements in addition to the providing the delays (or phase shifts) that result in antifocuing the beam. This amplitude adjustment permits the transmit beam to have a relatively flat pattern at the top as well as having nulls in the region of grating lobes.

The example shown if FIG. 28 is a wide transmit beam pattern characterized by an almost-constant amplitude almost up to the first dip 406, and with a deep null (the second dip 407) occurring at the angle of the grating lobes of a center-focused (un-steered) receiver pattern. One embodiment of the invention is implemented using a thinned array.

Combination

In one embodiment of the invention, a wide transmit beam pattern is characterized by an almost-constant amplitude almost up to the first dip, and with a deep null (the second dip) occurring at the angle of the grating lobes of a center-focused (un-steered) receiver pattern using a thinned array. By providing a transmit pattern that has been optimized to provide at substantially all ranges (including the near field), a flat, broad, mainbeam with low sidelobes and a null at the grating lobe location, multiple receiver elements can be simultaneously ensonated.

FIGS. 25(a-f) are two dimensional (2-D) Matlab representations of a pulsed, digitally processed, sampled and quantized transmitter beam pattern according to an embodiment of the invention. In FIG. 25 range is denoted by the letter "r". The x axis of each figure indicates cross range in millimeters. The y axis in each figure indicates transmitter output amplitude in decibels (db). The location of a would be receiver grating lobe corresponding to the cross range direction of the transmitted energy is indicated by an arrow in each figure. The pattern is illustrated at six different ranges (also referred to herein as depths): 15 mm, 20 mm, 30 mm, 40 mm, 60 mm and 120 mm respectively. The example shown represents a demodulated signal for a pulse comprising a plurality of cycles of a 6 Mhz carrier. As can be seen from the drawing, the waveform is characterized by having nulls (indicated by arrows) in positions corresponding to receiver grating lobes.

FIGS. 26(a-f) are Matlab pulsed simulations of patterns of a 16 element linear receive array. The simulations plot amplitude as a function of acoustic scatter cross range location, according to an embodiment of the invention. The figures compare the center focused array patterns (a-c) to the patterns (d-f) of an array steered 3 elements to the left of center. In FIGS. 26(a-c) the pattern is center focused at $x_1$, $z_1$=(0 mm, 60 mm) with a resolution of 1.2 mm. FIG. 26a illustrates the amplitude of the combined transmit/receive pattern in the x, z plane. FIG. 26b is a 2-D linear representation of the combined transmit/receive signal illustrated in FIG. 2a plotting amplitude as a function of cross range position in mm. In FIG. 26b cross range is indicated in mm along the x-axis. And amplitude is indicated along the y-axis. In FIGS. 26a, b, d and e amplitude is plotted linearly, e.g., volts. In figures FIGS. 26c and f, amplitude is plotted logarithmically in db. FIGS. 26b and c illustrate sidelobes at 211 and 220 and main lobe at 210. FIG. 26c is a 2-D logarithmic representation of the receiver and transmitter patterns illustrated in FIG. 26b. FIG. 26c illustrates sidelobes 220 and 225 of 33 db on either side of main lobe 210.

FIG. 26d illustrates the amplitude of the combined transmit/receive pattern in the x, z plane of the same array shown in 26a, moved three elements to the left, i.e., $(x_1, z_1)$=(−2.7 mm, 60 mm). FIGS. 26e and 26F show in 2-D the corresponding linear and logarithmic representations of the receiver gain pattern as a function of acoustic scatter cross range location at resolution 1.3 mm. As shown in FIG. 26f, a −25 db grating lobe 230 appears at approximate cross range 22 mm. Grating lobe 230 can also be seen in FIG. 26e at 230.

FIGS. 27(a-f) represent a simplified 2-D continuous wave (CW) simulation of a transmitter pattern according to an embodiment of the invention. Transmitter amplitude (in db) at ranges of 20 mm, 30 mm, 40 mm, 50 mm, 60 mm and 70 mm respectively are illustrated.

The pattern is characterized by a main lobe 310 having a generally flat top shape. This shape allows multiple receive beams to be received at the same relative amplitudes, thereby simplifying processing of the received information. The shape also allows the ratio of Signal to (Noise+Interference) to be maintained independently of receive beam direction.

FIG. 28 illustrates the 3-D pattern 400 of a 2-D array according to the embodiment of the invention illustrated in FIGS. 27(a-d). The transmitter array is anti-focused and amplitude weighted as described herein to produce a pattern 400 characterized by having a main lobe 410 with a generally flat top portion 405 such that an N×N array of receive beams will be illuminated with equal amplitude. Pattern 400 is further characterized by having nulls 407 in the region where grating lobes of the receive beams would normally appear.

The beam shapes illustrated in FIG. 27 is described by the relationship $h(u)=c$ for $|u|<u_1$ and $h(u)=0$ for $|u|>u_2$, where $u=\sin \theta$. In this manner, several receive elements can be ensonified within the transmitter pattern while grating lobes are attenuated. At short range (in the near field), the transmitted beam shape is approximately the same as the received illumination function. In this case very few transmit elements are entirely on. At long range (far field) the receive element illumination function $g(x)$ or $g(y)$ and the transmitted pattern, $h(u)$ are a Fourier transform pair. Thus, one embodiment of the invention uses a sinc function (sin x/x) for illumination. The desired illumination function is found by performing a Fast Fourier Transform (an FFT) on a sequence consisting of several constant positive values centered about zero (with zeros elsewhere), and then ignoring every second term of the FFT. For example, using the centered odd FFT outputs as weighting factors to be applied to array elements provides the four-element linear array weights,

[−0.2, 1.0 1.0, −0.2]

Wherein the array weight numbers represent amplitudes of the energy applied to the transmit elements.

This example weighting factor set produces desired patterns according to the invention at long ranges and at short ranges. In one embodiment of the invention, in addition to the weighting factors given above, delays are applied to the inner elements corresponding to focusing the array at about 20 mm (delay =[0, 3, 3, 0] in tics of a 96 MHz clock). As will be recognized by those of ordinary skill in the art, other combinations of weights and delays can also be used to produce the pattern of the invention.

One embodiment of the invention, employing time delay steering, provides a 180-degree phase shift for the outside elements by either delaying or advancing the outer elements by half a cycle. This corresponds, respectively, to either anti-focusing the array, or focusing it at an extremely short range. In this embodiment, the delay that corresponds to a 180 degree phase shift for a 6 MHz carrier, is 8 ticks of the 96 MHz clock. Accordingly, the element weights become

[0.2, 1.0, 1.0, 0.2]

and the antifocusing delays become [5, 0, 0, 5] (this is obtained by subtracting 3 from [8, 3, 3, 8] (measured in tics of the 96 MHz clock) ([8, 3, 3, 8] is obtained by adding 8 to the outside elements of the [0, 3, 3, 0] delay described above. In one embodiment of the invention good overall performance, using non-negative weights, was obtained with the weights above and delays of [6, 0, 0, 6] at 96 MHz. These delays correspond to focusing about 9 mm behind the array (in other words, anti-focusing).

Figure 29:
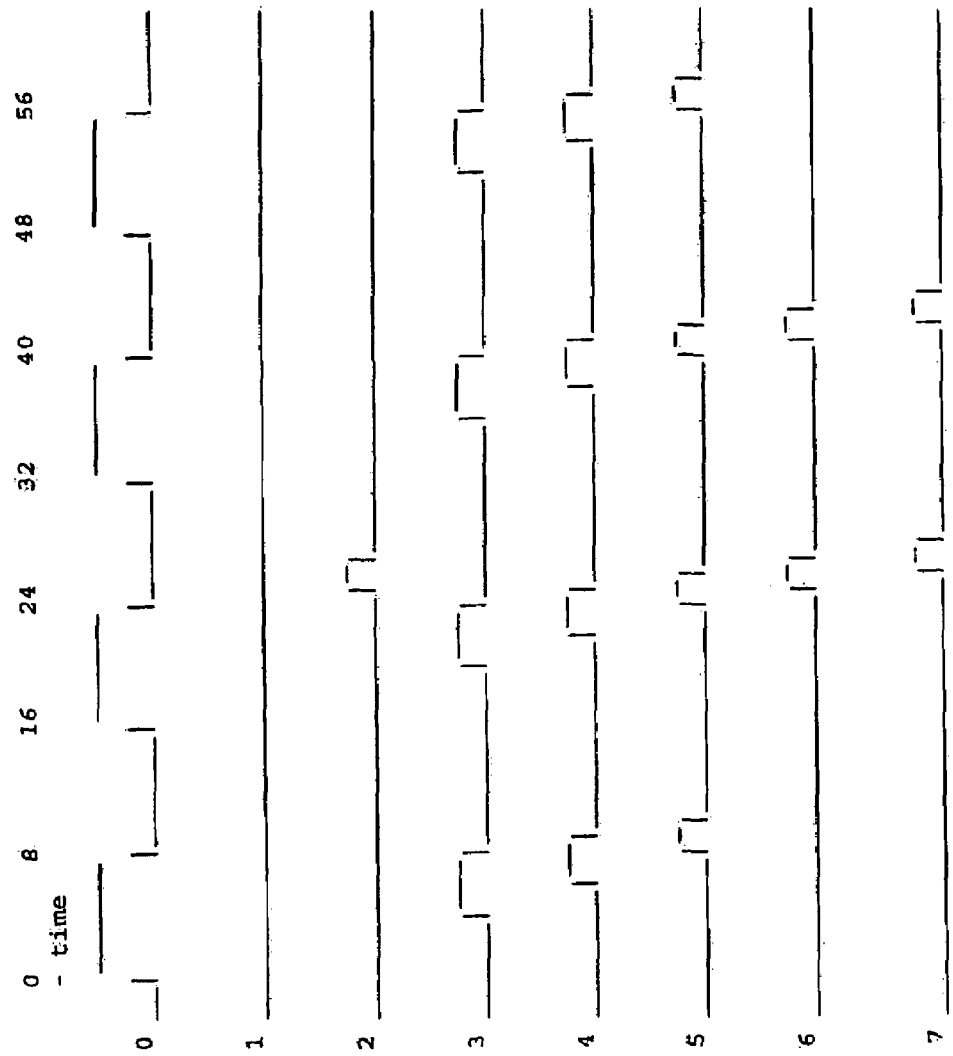
FIG. 29 is a timing diagram illustrating the sequencing of transmitter beam transmission according to an embodiment of the invention.

In the [5, 0, 0, 5] embodiment anti-focuses of −10 mm instead of −9 mm also produced the waveform of the invention. By adding 8 to [−8, 3, 3, −8] delays of [0, 11, 11, 0] are obtained. This corresponds to focusing at a very short range. At ranges of interest, the result is the same as antifocusing FIG. 29 is a waveform diagram representing one of many implementations of the waveforms used to create the transmitter beam profiles of the invention. Various embodiments of the invention will use more or less elements to create the transmitted beam. The example shown employs an 8×8 array. The numbers appearing from left to right across the top of FIG. 29 represent increments of time units. The waveforms (0-7) enable energy transmission from a corresponding element when high and disable energy transmission from a corresponding element when low. In the example shown time starts with 0, so waveform 0 has a delay of zero.

Waveform 2 has a delay of 25 and so forth. Transmitter elements using waveform 1 are always disabled. Each waveform 1-7 transmits a corresponding number of pulses. For example, waveform 0 transmits 4 pulses, waveform 2 transmits 1 cycle and so on. The relative widths of the pulses high indicate the duty cycle of the transmitter. For example, waveform 1 represents a 50% duty cycle, and waveform 5 represents a 12.5% duty cycle. The initial positive going edge of each waveform relative to time zero indicates the delay. For example, waveform 0 has a delay of 0 time units and waveform5 has a delay of 8 time units. The variation in duty cycle and number of pulses are used in lieu of amplitude variation.

Table 1 illustrates the waveform assignments for an 8×8 array of elements according to one embodiment of the invention.

TABLE 1

1 1 1 1 1 1 1 1
1 1 7 5 5 7 1 1
1 7 4 3 3 4 7 1
1 5 3 0 0 3 5 1
1 5 3 0 0 3 5 1
1 7 4 3 3 4 7 1
1 1 7 5 5 7 1 1
1 1 1 1 1 1 1 1

Table 2 illustrates the contents of a Read only memory storing the waveform

| Sel | ROM | cycles | High | Low | Delay | Start |
|-----|-----------|--------|------|-----|-------|-------|
| 0 | waveform0 | 4 | 8 | 8 | 0 | 0X3B |
| 1 | waveform1 | — | — | — | — | — |
| 2 | waveform2 | 1 | 2 | 14 | 25 | 0X54 |
| 3 | waveform3 | 4 | 4 | 12 | 4 | 0X3F |
| 4 | waveform4 | 4 | 3 | 13 | 6 | 0X41 |
| 5 | waveform5 | 4 | 2 | 14 | 8 | 0X43 |
| 6 | waveform6 | 2 | 2 | 14 | 25 | 0X54 |
| 7 | waveform7 | 2 | 2 | 14 | 26 | 0X55 |

Many other variations and modifications of the invention will be apparent to those skilled in the art without departing from the spirit and scope of the invention. The above-described embodiments are, therefore, intended to be merely exemplary, and all such variations and modifications are included within the scope of the invention as defined in the appended claims.

Various publications are cited herein, the disclosures of which are incorporated by reference in their entirety.

What is claimed is:

1. A method of configuring an ultrasound array to transmit a beam pattern sufficient to insonate a region of interest at an internal site of a subject, said method comprising the steps of:
   a) providing an array of ultrasound transducer elements;
   b) outputting a beam pattern from said array of ultrasound transducer elements to insonate a region of interest at an internal site in a body that is sufficiently large that the beam output pattern comprises a multi-beam pattern, insonating multiple receiver elements over a substantially simultaneous period by directing energy produced by said array of ultrasound transducer elements into said region of interest in said body, and adjusting an amplitude of energy output by said array of transducers to cause the beam pattern output to have a generally flat upper pattern and nulls in a grating lobe region; and
   c) introducing a propagation time delay of the beam pattern output from said array of ultrasound transducer elements, wherein the propagation delay increases as a distance increases from a central output area of said array of ultrasound transducer elements.

2. The method according to claim 1, wherein the transmission of said array of transducer elements is configured in step b) such that the beam pattern output by said array of transducer elements appears to propagate from a point source having a focal distance located behind said array of transducer elements when viewed from said region of interest.

3. The method according to claim 1, wherein step b) further includes adjusting a duty cycle of one or more pulses output by at least one transducer element of said array of transducer elements.

4. The method according to claim 1, wherein step b) includes adjusting a quantity of pulses output by at least one transducer element of said array of transducer elements.

5. The method according to claim 2, wherein step b) also includes adjusting a quantity of pulses output by said at least one transducer element of said array of transducer elements.

6. The method according to claim 1, wherein said array of transducer elements comprises an 8×8 array.

7. A method of configuring an ultrasound array to transmit a beam pattern sufficient to insonate a region of interest at an internal site of a subject, said method comprising the steps of:
   a) providing an array of ultrasound transducer elements;
   b) outputting a beam pattern from said array of ultrasound transducer elements to insonate a region of interest at an internal site in a body sufficiently large that the beam pattern comprises a multi-beam pattern, insonating multiple receiver elements over a substantially simultaneous period by directing energy produced by said array of ultrasound transducer elements into said region of interest in said body, and adjusting an amplitude of energy output by said array of transducers to cause the beam pattern output to have a generally flat upper pattern and nulls in a grating lobe region; and
   c) introducing a phase shift of the beam pattern output from said array of ultrasound transducer elements, wherein a degree of phase shift increases as a distance increases from a central output area of said array of ultrasound transducer elements.

8. The method according to claim 7, wherein the transmission of said array of transducer elements is configured in step b) such that the beam pattern output by said array of transducer elements appears to propagate from a point source having a focal distance located behind said array of transducer elements when viewed from said region of interest.

9. The method according to claim 7, wherein step b) further includes adjusting a duty cycle of one or more pulses output by at least one transducer element of said array of transducer elements.

10. The method according to claim 7, wherein step b) includes adjusting a quantity of pulses output by at least one transducer element of said array of transducer elements.

11. The method according to claim 7, wherein said array of transducer elements comprises an 8×8 array.

12. A device for transmitting a multibeam pattern from an array of ultrasound transducer elements sufficient to insonate a region of interest at an internal site in a subject, said device comprising:
   a) an array of ultrasound transducer elements;
   b) means for outputting a multi-beam pattern from said array of ultrasound transducer elements to insonate a region of interest in a body encompassing multiple receiver elements over a substantially simultaneous period by directing energy produced by said array of ultrasound transducer elements into said region of interest in said body and adjusting an amplitude of energy output by said array of transducers to cause the beam pattern output to have a generally flat upper pattern and nulls in a grating lobe region; and
   c) means for introducing a propagation time delay of the beam pattern output from said array of ultrasound transducer elements, wherein the propagation delay increases as a distance increases from a central output area of said array of ultrasound transducer elements.

13. A device for transmitting a multibeam pattern from an array of ultrasound transducer elements sufficient to insonate a region of interest at an internal site in a subject, said device comprising:
   a) an array of ultrasound transducer elements;
   b) means for outputting a multi-beam pattern from said array of ultrasound transducer elements to insonate a region of interest in a body encompassing multiple receiver elements over a substantially simultaneous period by directing energy produced by said array of ultrasound transducer elements into said region of interest in said body and adjusting an amplitude of energy output by said array of transducers to cause the beam pattern output to have a generally flat upper pattern and nulls in a grating lobe region; and
   c) means for introducing a phase shift of the beam pattern output from said array of ultrasound transducer elements, wherein a degree of phase shift increases as a distance increases from a central output area of said array of ultrasound transducer elements.

14. A method for operating an array of ultrasound transducer elements, wherein the element spacing in the array is greater than, equal to or less than a half wavelength of the ultrasound energy produced by the elements, and wherein the array is used differently in transmit and receive modes, comprising:
   forming a transmit beam from a position external to a region of interest encompassing a plurality of receive beams and initially acquiring a signal by insonating a target region comprising multiple receive beam positions over a substantially simultaneous period; receiving data from the multiple receive beam positions of the array; combining the received data in a processor; locking onto the receive beam and the point(s) producing a peak signal; and correcting for motions in the target region by periodically forming multiple receive beams and re-acquiring the peak signal.

15. A method of claim 14, additionally comprising forming a transmit beam using a subarray of the array.

16. A method of claim 14, wherein the large target region is a 3-D spatial region.

17. A method of claim 14, wherein the transmit beam uniformly insonates over a 2-D transmitter sub-aperture.

18. A method of claim 14, wherein the transmit beam has a fixed focus.

19. A method of claim 14, additionally comprising simultaneously and digitally forming multiple receive beams for receiving data.

20. A method of claim 14, additionally comprising Doppler processing the received data.

21. A method of claim 14, wherein the array is a monostatic array, and additionally comprising transmitting from the full aperture and scanning the transmitted beam over the region being examined.

22. A method of claim 14, additionally comprising using a transmitter diversity technique to spread temporal intensity over the face of the array.

23. A method of claim 22, comprising using a different transmit sub-aperture for different coherent burst of pulses.

24. A method of claim 14, additionally comprising steering the receive beams to a point or points that produce a peak signal.

25. A method of claim 24, wherein the peak signal is a maximum amplitude at high Doppler frequencies.

26. A method of claim 14, additionally comprising steering the receive beams using a phase steering or time-delay steering technique.

27. A method of claim 14, additionally comprising providing the array of ultrasound transducer elements on a low-profile easily-attached transducer pad.

28. A method of claim 14, additionally comprising determining spatial coordinates of received data.

29. A method of claim 28, additionally comprising forming and displaying a 3D map based on the spatial coordinates of received data.

30. An ultrasound device comprising an array of ultrasound transducer elements, wherein the element spacing in the array is greater than, equal to or less than a half wavelength of the ultrasound energy produced by the elements, and additionally comprising means for operating the array differently in transmit and receive modes, and forming a transmit beam encompassing a plurality of receive beams for initially acquiring a signal by insonating a target region comprising multiple receive beam positions simultaneously, receiving data from the multiple receive beam positions of the array, processing the received data to lock onto the receive beam and the point(s) producing a peak signal, and correcting for motions in the target region by periodically forming multiple receive beams and re-acquiring the peak signal.

31. A device of claim 30, wherein the transmit beam uniformly insonates over a 2-D transmitter sub-aperture.

32. A device of claim 30, wherein the transmit beam has a fixed focus.

33. A device of claim 30, additionally comprising means for simultaneously and digitally forming multiple receive beams for receiving data.

34. A device of claim 30, additionally comprising means for Doppler processing the received data.

35. A device of claim 30, additionally comprising means for steering the receive beams to a point or points that produce a peak signal.

36. A device of claim 35, wherein the peak signal is a maximum amplitude at high Doppler frequencies.

37. A device of claim 35, additionally comprising means for steering the receive beams using a phase steering or time-delay steering technique.

38. A device of claim 30, wherein the array of ultrasound transducer elements is provided on a low-profile easily-attached transducer pad.

39. A device of claim 30, additionally comprising means for determining spatial coordinates of received data.

40. A device of claim 39, additionally comprising a display device, and means for forming and displaying a 3D map based on the spatial coordinates of received data.

* * * * *